United States Patent [19]

Keana et al.

[11] Patent Number: 5,574,070
[45] Date of Patent: Nov. 12, 1996

[54] SUBSTITUTED GUANIDINES HAVING HIGH BINDING TO THE SIGMA RECEPTOR AND THE USE THEREOF

[75] Inventors: John F. W. Keana, Eugene, Oreg.; Eckard Weber, Laguna Beach, Calif.

[73] Assignees: State of Oregon, acting by and through the Oregon State Board of Higher Education, acting for and on behalf of the Oregon Health Sciences University; The University of Oregon, both of Eugene, Oreg.

[21] Appl. No.: 952,849

[22] PCT Filed: May 22, 1991

[86] PCT No.: PCT/US91/03594

§ 371 Date: Jan. 22, 1993

§ 102(e) Date: Jan. 22, 1993

[87] PCT Pub. No.: WO91/18868

PCT Pub. Date: Dec. 12, 1991

Related U.S. Application Data

[63] Continuation-in-part of Ser. No. 657,759, Feb. 21, 1991, abandoned, and a continuation-in-part of Ser. No. 528,216, May 25, 1990, abandoned.

[51] Int. Cl.⁶ ................................................. A61K 31/155
[52] U.S. Cl. .............................................................. 514/634
[58] Field of Search .............................. 514/634; 564/238

[56] References Cited

U.S. PATENT DOCUMENTS

| | | | |
|---|---|---|---|
| 1,422,506 | 7/1922 | Weiss | 564/238 |
| 1,597,233 | 8/1926 | Heuser et al. | 564/238 |
| 1,642,180 | 9/1927 | Scott | 564/238 |
| 1,672,431 | 6/1928 | Schotte | 514/634 |
| 1,756,315 | 4/1930 | Ter Horst | 564/238 |
| 1,795,738 | 3/1931 | Schotte | 514/634 |
| 1,850,682 | 3/1932 | Meiss | 564/238 |
| 1,915,922 | 6/1933 | Christman et al. | 514/634 |
| 2,145,214 | 1/1939 | Jayne, Jr. | 514/634 |
| 2,254,009 | 8/1941 | Hechenbleikner | 564/238 |
| 2,274,476 | 2/1942 | Hechenbleikner | 564/238 |
| 2,362,915 | 11/1944 | MacGregor | 564/238 |
| 2,633,474 | 3/1953 | Beaver | 564/238 |
| 3,140,231 | 7/1964 | Luskin et al. | 514/634 |
| 3,159,676 | 12/1964 | Spickett et al. | 564/238 |
| 3,228,975 | 1/1966 | Abraham et al. | 514/634 |
| 3,248,426 | 4/1966 | Dvornik | 514/634 |
| 3,270,054 | 8/1966 | Gagneux et al. | 564/238 |
| 3,283,003 | 11/1966 | Jack et al. | 514/634 |
| 3,301,755 | 1/1967 | Mull | 564/238 |
| 3,320,229 | 5/1967 | Szabo et al. | 564/238 |
| 3,409,669 | 11/1968 | Dyke | 564/238 |
| 3,479,437 | 11/1969 | Szabo et al. | 514/634 |
| 3,547,951 | 12/1970 | Hardie et al. | 514/634 |
| 3,639,477 | 2/1972 | L'Italien | 564/238 |
| 3,681,459 | 8/1972 | Hughes et al. | 564/238 |
| 3,769,427 | 10/1973 | Hughes et al. | 564/238 |
| 3,804,898 | 4/1974 | Panneman | 514/634 |
| 3,908,013 | 9/1975 | Hughes et al. | 564/238 |
| 3,968,243 | 7/1976 | Maxwell et al. | 514/634 |
| 3,976,643 | 8/1976 | Diamond et al. | 514/634 |
| 3,976,787 | 8/1976 | Hughes et al. | 564/238 |
| 4,007,181 | 2/1977 | DuCharme et al. | 564/238 |
| 4,014,934 | 3/1977 | Hughes et al. | 564/238 |
| 4,051,256 | 9/1977 | Swallow | 564/238 |
| 4,052,455 | 10/1977 | Matier et al. | 564/238 |
| 4,109,014 | 8/1978 | Liu et al. | 564/238 |
| 4,130,663 | 12/1978 | Matier et al. | 514/634 |
| 4,169,154 | 9/1979 | Cohen et al. | 514/634 |
| 4,284,642 | 8/1981 | Toldy et al. | 424/273 |
| 4,369,325 | 1/1983 | Toldy et al. | 548/315 |
| 4,400,383 | 8/1983 | Davidson et al. | 514/634 |
| 4,471,137 | 9/1984 | Barton et al. | 564/238 |
| 4,575,514 | 3/1986 | Carson | 564/238 |
| 4,709,094 | 11/1987 | Weber et al. | 514/634 |
| 4,780,466 | 10/1988 | Hrib et al. | 514/634 |
| 4,898,978 | 2/1990 | Bergfeld et al. | 514/634 |
| 4,906,779 | 3/1990 | Weber et al. | 564/238 |
| 5,093,525 | 3/1992 | Weber et al. | 564/238 |
| 5,190,976 | 3/1993 | Weber et al. | 514/634 |
| 5,312,840 | 5/1994 | Keana et al. | 514/634 |

FOREIGN PATENT DOCUMENTS

| | | |
|---|---|---|
| 0001500 | 4/1979 | European Pat. Off. . |
| 0035374 | 9/1981 | European Pat. Off. . |
| 0179642 | 4/1986 | European Pat. Off. . |
| 514248 | 9/1927 | Germany . |
| 2133056 | 1/1973 | Germany . |
| 2916140 | 10/1979 | Germany . |
| 223410 | 10/1924 | United Kingdom . |
| 258203 | 9/1926 | United Kingdom . |
| 478525 | 1/1938 | United Kingdom . |
| WO87/04433 | 7/1987 | WIPO . |
| WO88/00583 | 1/1988 | WIPO . |
| WO90/14067 | 11/1990 | WIPO . |

OTHER PUBLICATIONS

S. Siddiqui et al., *Pakistan Journal of Scientific and Industrial Research*, 30(3):163–181 (1987).

C. Chavkin et al., *Advances in the Biosciences*, 75:407–410 (1989).

J. Keana et al., *Proc. Natl. Acad. Sci. USA*, 86:5631–5635 (1989).

H. Wanzlick et al., *Chemische Berichte*, 98(10):3170–3177 (1965).

D. Lloyd et al., *Tetrahedron*, 33:1379–1389 (1977).

K. Akiba et al., *Bulletin of the Chem. Soc. of Japan*, 47(4):935–937 (1974).

E. Maida et al., *Wiener Klinische Wochenschrift*, 90(1):43–48 (1978).

(List continued on next page.)

*Primary Examiner*—Raymond Henley, III
*Attorney, Agent, or Firm*—David G. Conlin; Peter F. Corless; Ernest V. Linek

[57] ABSTRACT

The invention relates to a method for the treatment or prophylaxis of psychosis, depression, hypertension, or anxiety in an animal by administering an effective amount of an N,N'-disubstituted guanidine or 2-iminoimadazolidine having an affinity for the sigma receptor. The invention also relates to the novel guanidines of the invention as well as pharmaceutical compositions thereof.

19 Claims, 17 Drawing Sheets

OTHER PUBLICATIONS

H. Shimizu et al., *Chem. Abstracts*, 111(2), Abstr. No. 16337m (1989).
A. Heesing et al., *Chem. Abstracts*, 64(11), Abstr. No. 15776h (1966).
T. Tada et al., *Chem. Abstracts, 104(24), Abstr. No. 208252g (1986).*
L. Kiselev et al., *Chem. Abstracts*, 91(21), Abstr. No. 175291b (1979).
J. T. Adams et al., *Eur. J. Pharm.*, 142:61–71 (1987).
P. N. Bhargava et al., *Chemical Abstracts*, 86:598, 189787b (1977).
W. D. Bowen et al., *Eur. J. Pharm.*, 147:153–154 (1988).
B. G. Campbell et al., *J. Neurosci.*, 9(10):3380–3391 (1989).
I. V. Dranka et al., *Russian J. Inorg. Chem.*, 26(3):347–350 (1981).
G. J. Durant et al., *J. Med. Chem.*, 28:1414–1422 (1985).
S. E. File, *TINS*, 10:461–463 (1987).
H. W. Geluk et al., *J. Med. Chem.*, 12:712–715 (1969).
M. P. Kavanaugh et al., *Proc. Natl. Acad. Sci. USA*, 85:2844–2848 (1988).
C. A. Maryanoff et al., *J. Org. Chem.*, 51:1882–1884 (1986).
S. R. Safir et al., *J. Org. Chem.*, 13:924–932 (1948).
M. W. Scherz et al., *J. Med. Chem.*, 33:2421–2429 (1990).
M. S. Sonders et al., *TINS*, 11:37–40 (1988).
A. A. Stolyarchuk et al., *Chemical Abstracts*, 86:522–523, 121071h (1977).
B. Tester et al., *Society for Neuroscience, 19th Annual Meeting*, p. 983, 396.17 (1989).
T. J. R. Weakley et al., *Acta Cryst.*, 46:2234–2236 (1990).
E. Weber et al., *Proc. Natl. Acad. Sci. USA*, 83:8784–8788 (1986).
H. G. M. Westenberg et al., *Psychopharmacol. Bull.*, 23:145–149 (1987).
Supplementary Partial European Search Report for the corresponding European Application No. EP8790447 (1988).
International Search Report for International Application No. PCT/US90/02398, filed May 2, 1990.
J. Fischer et al., "High–Affinity Binding of [$^3$] Adamantyl–Tolyl Guanidines To The Sigma Receptor", abstract No. 159.13, vol. 16, Society for NeuroScience Abstracts (1990).
F. Monnet et al., "Multiple Sigma and PCP Receptor Ligands: Mechanism For Neuromodulation and Protection", (1991).
A. Wilson et al., *J. Nuclear. Medicine*, 31(5):747, abstract No. 376 (1990).
B. Campbell et al., *European Journal of Pharmacology*, 205:219–233 (1991).
T. Massamiri et al., *The Journal of Pharmacology and Experimental Therapeutics*, 259:(1)22–29 (1991).

ADTG GIVEN AT A DOSE OF 1mg/kg p.o. 40 MIN BEFORE TEST.

n=5. *p<0.05-P<0.001

DAG = di-adamantyl-guanidine
AIG = adamantyl-o-Iodo-phenyl-guanidine
BOTH COMPOUNDS WERE GIVEN AT A DOSE OF 1mg/kg p.o., 40 min BEFORE TEST.
n= 5  *P<0.01-P<0.001

FIG.9
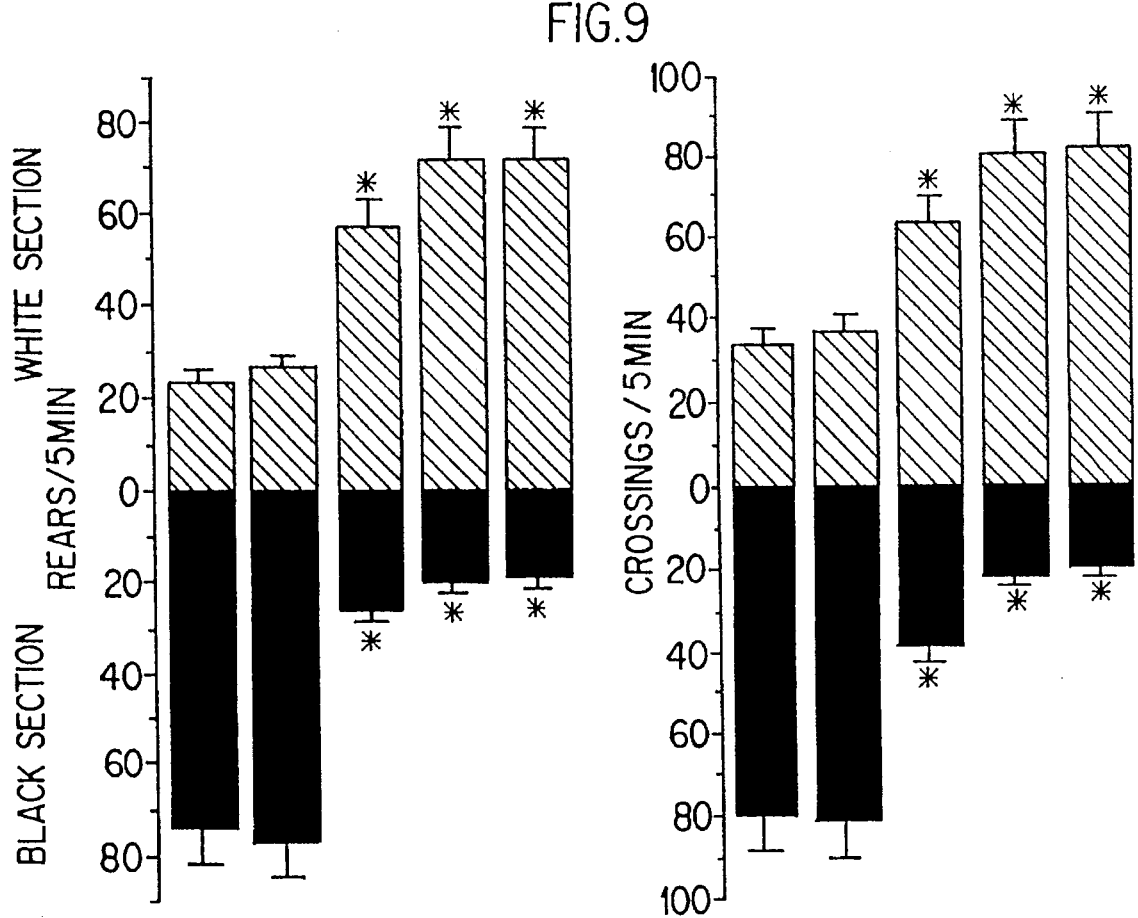
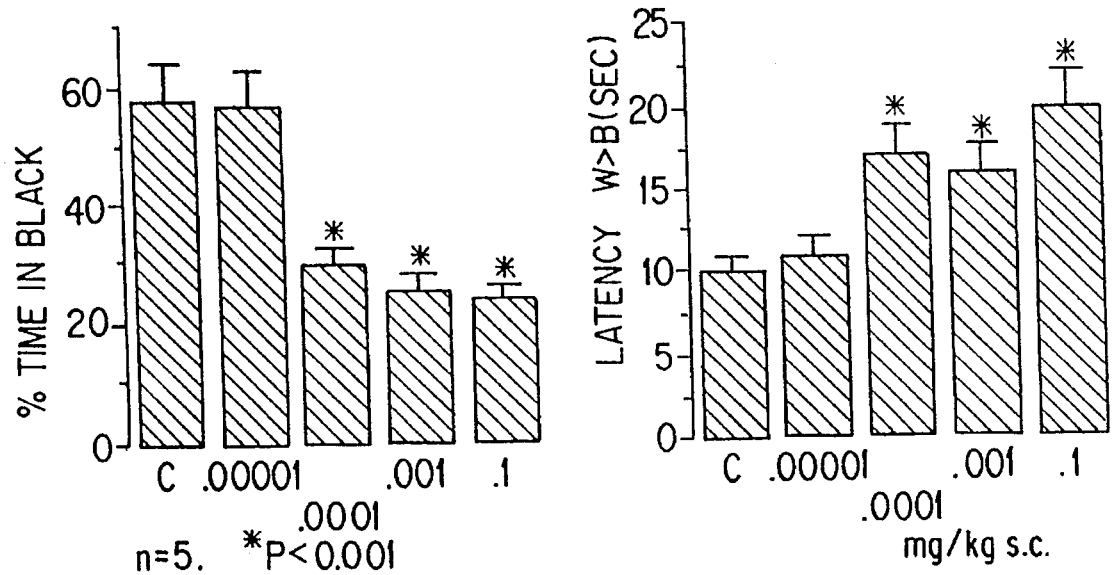

FIG. 11
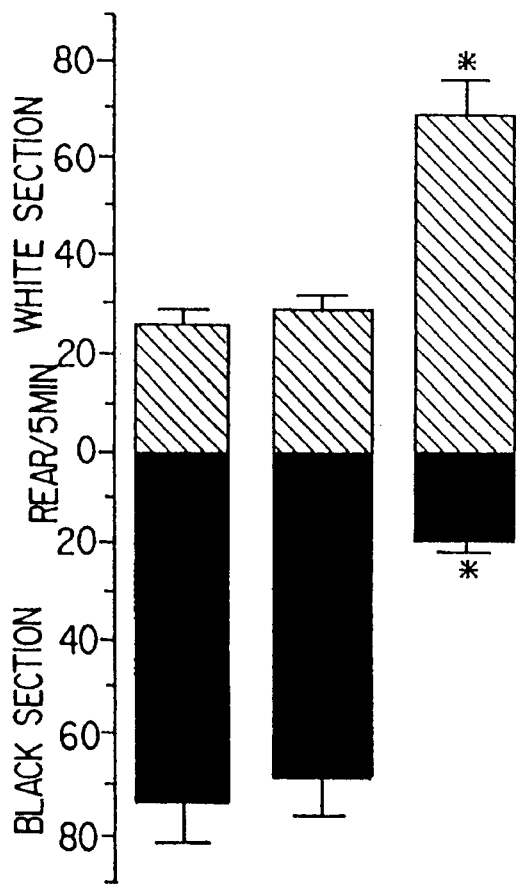
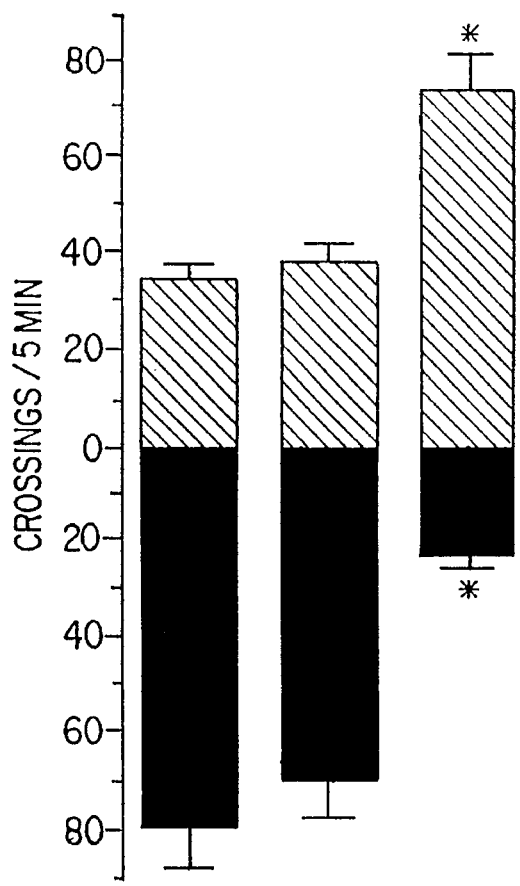
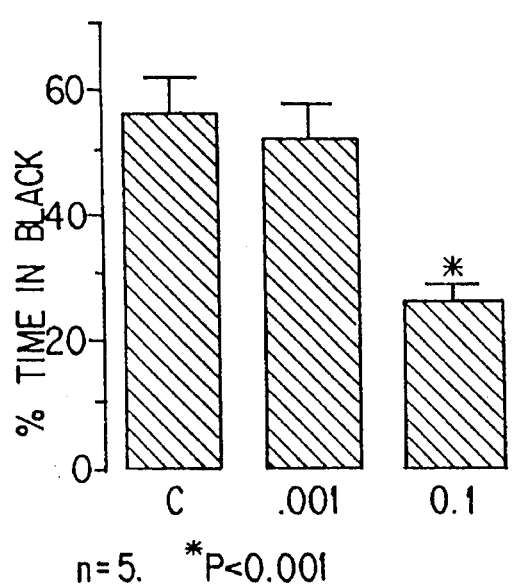
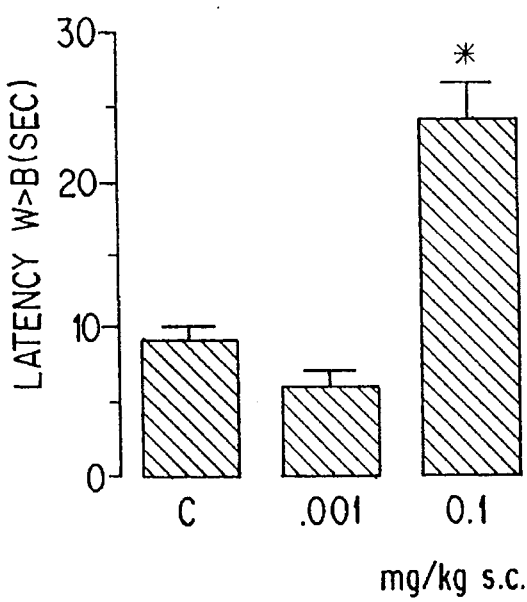
n=5.  *P<0.001
mg/kg s.c.

FIG. 13
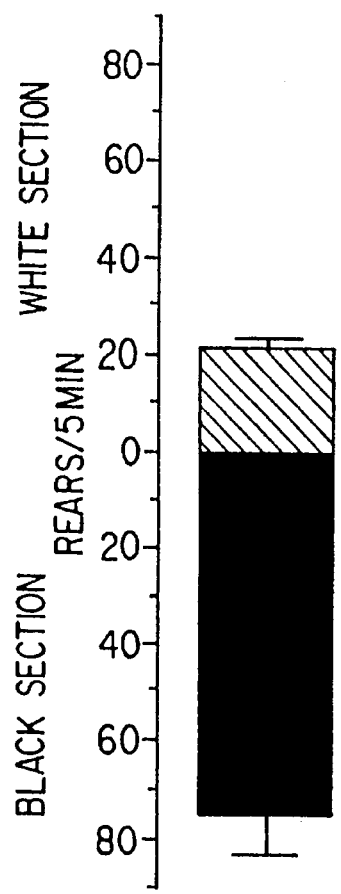
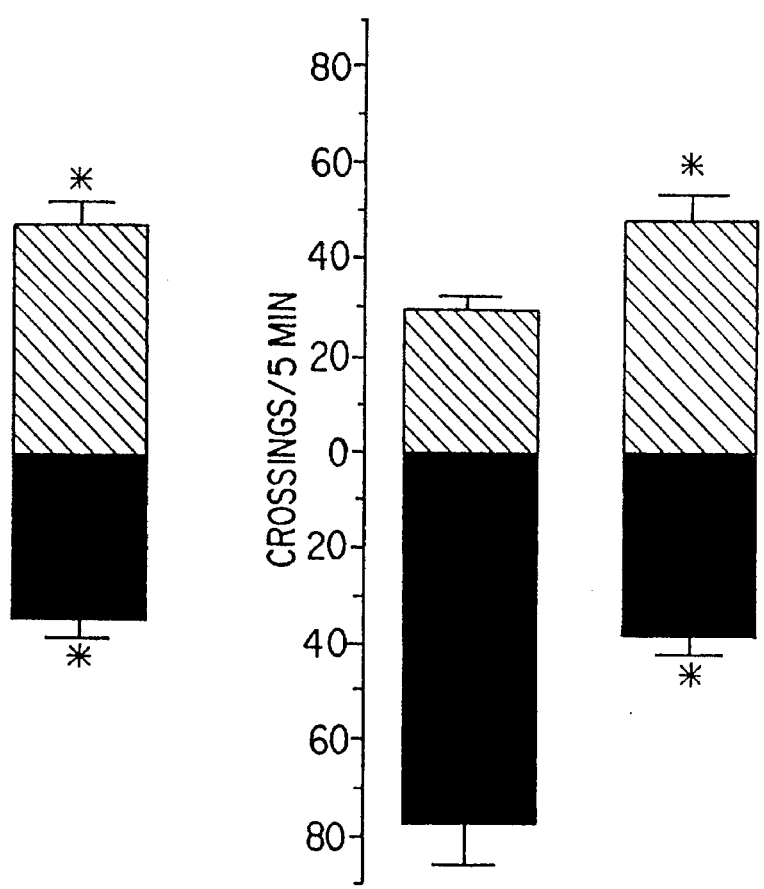
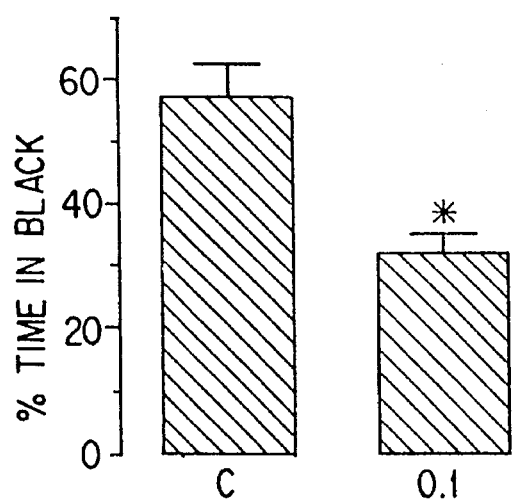
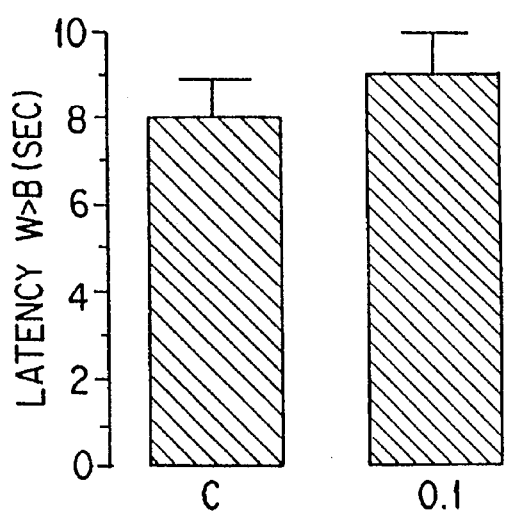
n=5. *P<0.01 – P<0.001
mg/kg p.o.

n = 5. †P<0.05 (ANXIOGENESIS).

SUBSTITUTED GUANIDINES HAVING HIGH BINDING TO THE SIGMA RECEPTOR AND THE USE THEREOF

CROSS REFERENCE TO RELATED APPLICATIONS

The present application is a continuation-in-part of U.S. application Ser. No. 07/657,759, filed Feb. 21, 1991, now abandoned, and a continuation-in-part of U.S. application Ser. No. 07/528,216, now abandoned, filed May 25, 1990, the disclosures of which are fully incorporated by reference.

FIELD OF THE INVENTION

The invention is in the field of medicinal chemistry. In particular, the invention relates to N,N'-disubstituted guanidines and N,N'-disubstituted 2-iminoimidazolidines which have high binding to the sigma receptor, pharmaceutical compositions thereof, and methods for treating or preventing psychotic mental illness, depression, hypertension, and anxiety in animals.

BACKGROUND OF THE INVENTION

Recently, the inventors have described a series of di-arylguanidines which are potent ligands for brain sigma receptors (Weber, et al., *PNAS* (*USA*) 83:8784–8788 (1986); Campbell et al., *J. Neurosci.* 9:3380–3391 (1989); U.S. Pat. No. 4,709,094). Brain sigma receptors bind many psychotropic drugs (Sonders et al., *Trends Neurosci.* 11:37–40 (1988)). The physiological function of sigma receptors in the nervous system is subject to intense investigations (Sonders et al., *Trends Neurosci.* 11:37–40 (1988)) because certain sigma receptor selective compounds have known antipsychotic activity suggesting that sigma receptor active compounds can be used for the treatment of schizophrenia (Largent et al., *Eur. J. Pharmacol.*, 11:345–347 (1988)).

A wide variety of substituted guanidines are disclosed in the patent literature. For example:

U.S. Pat. Nos. 1,411,731 and 1,422,506 discloses diphenylguanidine as a rubber accelerator;

U.S. Pat. No. 1,597,233 discloses N-o-tolyl-N'-phenyl-guanidine as a rubber accelerator;

U.S. Pat. No. 1,672,431 discloses N,N'-di-o-methoxyphenyl-guanidine as being useful for therapeutic purposes, especially in the form of water-soluble salts;

U.S. Pat. No. 1,730,338 discloses N-p-dimethyl-aminophenyl-N'-phenylguanidine as a rubber accelerator;

U.S. Pat. No. 1,795,738 discloses a process for the production of N,N'-dialkyl-di-substituted guanidines, including N-di-ethyl-N'-phenyl-guanidine, N-diethyl-N-isoamylguanidine, N-dimethyl-N'-isoamylguanidine and N-dimethyl-N'-ethylguanidine;

U.S. Pat. No. 1,850,682 discloses a process for the preparation of disubstituted guanidine rubber accelerators bearing an additional substituent on the imine nitrogen atom;

U.S. Pat. No. 2,145,214 discloses the use of disubstituted guanidines, e.g., diarylguanidines especially dixylylguanidine, as parasiticides;

U.S. Pat. No. 2,254,009 discloses sym-di-2-octyl-guanidine and U.S. Pat. Nos. 2,274,476 and 2,289,542 disclose sym-dicyclohexylguanidine as insecticides and moth larvae repellents;

U.S. Pat. No. 2,633,474 discloses 1,3-bis(o-ethylphenyl)guanidine and 1,3-bis(p-ethylphenyl)guanidine as rubber accelerators;

U.S. Pat. No. 3,117,994 discloses N,N',N"-trisubstituted guanidines and their salts as bacteriostatic compounds;

U.S. Pat. No. 3,140,231 discloses N-methyl- and N-ethyl-N'-octylguanidines and their salts as antihypertensive agents;

U.S. Pat. No. 3,248,246 describes (Example 5) a 1,3-disubstituted guanidine whose substituents are hydrophobic hydrocarbon groups, one of which is naphthylmethyl and the other is n-butyl;

U.S. Pat. No. 3,252,816 discloses various N-substituted and unsubstituted cinnamyl-guanidines and generically the corresponding N'- and N"-alkyl substituted compounds and their salts as antihypertensive agents;

U.S. Pat. No. 3,270,054 discloses N-2-adamant-1-yl- and N-2-homoadamant-1-yl-oxy-ethyl-thioethyl- and aminoethyl-guanidine derivatives bearing at most two lower alkyl groups on the N'- and/or N"-nitrogen atom as sympathicolytic and anti-viral agents;

U.S. Pat. No. 3,301,755 discloses N-ethylenically unsubstituted-alkyl-guanidines and the corresponding N'- and/or N"-lower alkyl compounds as hypoglycemic and antihypertensive agents;

U.S. Pat. No. 3,409,669 discloses N-cyclohexylamino-(3, 3-dialkyl-substituted-propyl)-guanidines and the corresponding N'-alkyl- and/or N"-alkyl-substituted compounds as hypotensive agents;

U.S. Pat. No. 3,547,951 discloses 1,3-dioxolan-4-yl-alkyl-substituted guanidines which have anti-hypertensive activity and discloses lower alkyl, including n-butyl, as a possible substituent on the other amino group;

U.S. Pat. No. 3,639,477 discloses propoxylguanidine compounds as having anorectic properties;

U.S. Pat. Nos. 3,681,459; 3,769,427; 3,803,324; 3,908, 013; 3,976,787; and 4,014,934 disclose aromatic substituted guanidine derivatives wherein the phenyl ring can contain hydroxy and/or halogen substituents for use in vasoconstrictive therapy;

U.S. Pat. No. 3,804,898 discloses N-benzylcyclobutenyl and N-benzylcyclo-butenyl-alkyl-guanidines and the corresponding N-alkyl and/or N"-alkyl-substituted compounds as hypotensive agents;

U.S. Pat. No. 3,968,243 discloses N-axalkyl substituted guanidines and the corresponding N'-alkyl-n"alkyl and N',N'-aralkyl compounds as being useful in the treatment of cardiac arrhythmias;

U.S. Pat. No. 3,795,533 discloses o-halo-benzylidene-amino-guanidines and their use as anti-depressants for overcoming psychic depression;

U.S. Pat. No. 4,007,181 discloses various N,N'-disubstituted guanidines substituted on the imine nitrogen atom by adamantyl as possessing antiarrhythmic and diuretic activities;

U.S. Pat. No. 4,051,256 discloses N-phenyl- and N-pyridyl-N'-cycloalkylguanidines as antiviral agents;

U.S. Pat. Nos. 4,052,455 and 4,130,663 disclose styrylamidines, as analgesics agents or for the prevention of blood platelet aggregation;

U.S. Pat. No. 4,109,014 discloses N-hydroxysubstituted guanidines and the corresponding N-methyl disubstituted guanidines as vasoconstrictor agents;

U.S. Pat. No. 4,169,154 discloses the use of guanidines in the treatment of depression;

U.S. Pat. No. 4,393,007 discloses N-substituted and unsubstituted, N-substituted methyl-N'-unsubstituted, monosubstituted and disubstituted-N"-unsubstituted and substituted guanidines as ganglionic blocking agents; and U.S. Pat. No. 4,471,137 discloses N,N,N'N"-tetraalkyl guanidines as being sterically hindered bases useful in chemical synthesis.

U.S. Pat. No. 4,709,094 discloses 1,3-disubstituted-guanidines, e.g., 1-3-dibutylguanidine and 1,3 di-o-tolyl-quinidine, as sigma brain receptor ligands.

For examples of other substituted guanidines, see, e.g., U.S. Pat. Nos. 1,422,506; 1,642,180; 1,756,315; 3,159,676; 3,228,975; 3,248,426; 3,283,003; 3,320,229; 3,479,437; 3,547,951; 3,639,477; 3,784,643; 3,949,089; 3,975,533; 4,060,640 and 4,161,541.

Geluk, H. W., et al., *J. Med. Chem.*, 12, 712 (1969) describe the synthesis of a variety of adamantyl disubstituted guanidines as possible antiviral agents, including N,N'-di-(adamantan-1-yl)-guanidine hydrochloride, N-(adamantan-1-yl)-N'-cyclohexyl-guanidine hydrochloride and N-(adamantan-1-yl)-N'-benzyl-guanidine hydrochloride.

U.S. Pat. No. 4,709,094 (1987), discloses N,N'-disubstituted guanidine derivatives which exhibit high binding activity with respect to the sigma receptor having the Formula (I):

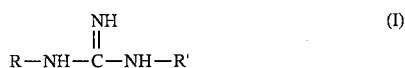

wherein R and R' are an alkyl group of at least 4 carbon atoms, a cycloalkyl group of 3–12 carbon atoms, or carbocyclic or aryl, of at least 6 carbon atoms.

Two of the novel N,N'-disubstituted guanidines disclosed therein are also claimed therein viz., 1,3-di-(4-halo-2-methylphenyl)-guanidine and 1,3-di-(4-$^3$H]-(2-methylphenyl)-guanidine.

Also claimed therein is a method of determining the relationship of abnormal psychotic-like behavior in a mammal displaying such behavior to sigma receptor system dysfunction, which comprises administering to the mammal displaying such behavior a water-soluble N,N'-disubstituted-guanidine which displaces in vitro N,N'-di-(4-[$^3$H]-2-methylphenyl)-guanidine bound to mammalian brain membrane, in an amount effective to alter the sigma brain receptor-modulated mental activity of the mammal; a method of treating a human being suffering from a psychotic mental illness associated with hallucinations, which comprises administering thereto a water-soluble N,N'-disubstituted guanidine which is an antagonist to the sigma receptor binding activity of a hallucinogenic benzomorphan, in an amount effective to ameliorate the hallucinations.

In U.S. Pat. No. 4,709,094 is further disclosed a method of determining the sigma brain receptor binding activity of an organic compound which comprises the steps of a) contacting in an aqueous medium a known mount of isolated mammalian brain membrane which has sigma receptor-like binding activity, with a mixture of (i) a tritium labeled N,N'-disubstituted guanidine which selectively binds sigma brain receptors, in a known mount capable of being bound to the sigma receptors of that brain membrane; and (ii) varying known amounts of a water soluble organic compound to be assayed for sigma receptor binding activity; b) separating the brain membrane from the tritium labeled compound which is not bound to the brain membrane in step a); and c) determining, from the molar relationship of the proportion of bound tritium-labeled compound which is separated in step b) to the molar amount of the organic compound employed in step a), the sigma receptor binding activity of that organic compound.

Certain benzomorphan opiates, such as N-allyl-normetazocine (SKF 10,047) and cyclazocine, in addition to analgesia, cause hallucinations, depersonalization, drunkenness and other psychotomimetic effects in man. In monkeys, dogs and rodents the psychotomimetic opiates cause behavioral and autonomic effects that are unlike those observed with administration of classical opiates such as morphine or the opioid peptides. Specific sigma "opioid" receptors in the brain are believed to mediate such atypical effects. Martin et al., *J. Pharmacol. Exp. Ther.* 197:517–532 (1976). It is believed that the sigma receptors also mediate some of the psychotomimetic effects of phencyclidine [PCP, angel dust], or alternatively, that psychotomimetic opiates act at specific PCP receptors. Zukin, R. S., et al., *Mol. Pharmacol.* 20:246–254 (1981); Shannon, H. E., *J. Pharmacol. Exp Ther.* 225:144–152 (1983); White, J. M., et al., *Psychopharmacology* 80:1–9 (1983); and Zukin et al., *J. Neurochem.* 46:1032–1041 (1986). PCP is a drug of abuse that causes a behavioral syndrome in man similar to that which is observed in schizophrenic psychosis. Aniline, O., et al., *CRC Critical Rev. Toxicol.* 10:145–177 (1982). Because of the potent psychotomimetic effects of sigma opiates and PCP, it is believed that sigma (and/or PCP) receptors play a role in mental illness, particularly schizophrenia.

A systematic investigation of the role of sigma receptors in normal and abnormal brain function has been hindered by a lack of specific sigma receptor binding assays and bioassays. Development of such specific assays requires well-characterized, highly selective and potent sigma receptor ligands. Recent studies have shown that brain membrane receptors can be labeled in vitro with (±)[$^3$H]SKF 10,047, Su, T. P., *J. Pharmacol. Exp. Ther.* 223:284–290 (1982); (+)[$^3$H]SKF 10,047, Tam, S. W., et al., *Proc. Natl. Acad. Sci. U.S.A.* 81:5618–5621 (1984); Martin et al., *J. Pharmacol. Exp. Ther.* 231:539–544 (1984); and Mickelson, M. M., et al., *Res. Commun. Chem. Pathol. Pharmacol.* 47:255–263 (1985), although not selectively, Gundlach et al., *Eur. J. Pharmacol.* 113:465–466 (1985); and Largent, B. L., et al., *J. Pharmacol. Exp. Ther.* 238:739–748 (1986), and with (+)[$^3$H]3-(3-hydroxyphenyl)-N-(1-propyl)-piperidine ((+)[$^3$H]3-PPP), Largent et al., *Proc. Natl. Acad. Sci. U.S.A.* 81:4983–4987 (1984), which is apparently more selective for sigma receptors than the others.

After the initial in vitro studies by Martin et al., (1976) supra, Keats and Telford (Keats, A. S., et al., "Analgesics: Clinical Aspects." In *Molecular Modification in Drug Design*, R. F. Gould (ed.), Advances in Chemistry Series #45 Amer. Chem. Soc., Wash. D.C. (1964)), and Haertzen (Haertzen, C. A. Cyclazocine and Nalorphine on the Addiction Research Center Inventory (ARCI), *Psychopharmacologia* (Berl.) 18:355–377 (1970)), numerous investigators set out to biochemically characterize the different opiate receptors (mu receptors, kappa receptors and sigma receptors) in vitro.

The first evidence for the existence of a separate sigma receptor in test tube experiments was provided by Su (1982) supra in a paper describing an etorphine-inaccessible binding site in guinea pig brain membranes which was apparently selectively labeled by tritium-labeled SKF-10,047. To overcome the fact that SKF10,047 could label multiple opioid receptors in the brain, Su performed his receptor binding assay using tritium labeled SKF-10,047 in the presence of excess unlabeled etorphine. Etorphine is a very strong opiate agonist drug which is known to bind to delta receptors, mu receptors and kappa receptors with almost equal potency. Su used etorphine to saturate all mu, kappa and delta receptors in a brain membrane preparation and then added tritium labeled SKF-10,047. This enabled him to detect a sigma binding site that was apparently different from mu, kappa and delta receptors.

A major breakthrough in identifying the sigma receptor as a separate entity occurred when Tam et al. (1984), supra, demonstrated that the previous problems in selectively labeling the sigma receptor were caused by the fact that in all previous experiments a racemic SKF-10,047 preparation was used. Tam showed that using a tritium labeled (+)-SKF-10,047 isomer one could selectively label a sigma receptor that was different from the mu, delta and kappa opioid receptors. On the other hand, Tam showed that (−)-SKF-10, 047 apparently labeled the mu and kappa receptors but not the sigma receptors. Tam, S. W., *Eur. J. Pharm.* 109:33–41 (1985). This finding has now been confirmed. (Martin et al., 1984, supra). Moreover, there is evidence from behavioral experiments, Khazan et al., *Neuropharm.* 23:983–987 (1984); Brady et al., *Science* 215:178–180 (1981), that it is the (+)-SKF-10,047 isomer that is solely responsible for the psychotomimetic effects of SKF-10,047.

One of the most important findings of the biochemical characterization of the sigma receptor has been that this receptor binds all synthetic opiate drugs that are known to have hallucinogenic and psychotomimetic effects. Opiates that do not have psychotomimetic effects in vivo do not bind to this receptor. Most importantly, it has been shown that besides hallucinogenic opiate drugs, the sigma receptor also binds many antipsychotic drugs that are used clinically to treat hallucinations in schizophrenic patients. (Tam and Cook, 1984). The initial observations with regard to antipsychotic drug binding to the sigma receptor (Su, 1982) were subsequently extensively confirmed and extended by Tam et al. (1984), supra, also showed that when one used radioactively labeled haloperidol, one of the most potent antipsychotic drugs that is used clinically, about half of the binding sites in brain membrane preparations are actually sigma receptors whereas the other half of the binding sites are apparently dopamine receptors. It has long been known that most antipsychotic drugs are also dopamine receptor antagonists. Previously the beneficial actions of antipsychotic drugs in psychotic patients have been attributed to the dopamine receptor-blocking effect of these drugs. It is clear from the work by Tam, however, that numerous clinically used antipsychotic drugs also bind to the sigma site. All antipsychotic drugs that bind to the sigma receptor may in part cause the beneficial effect of alleviating hallucinations through the sigma receptor. Taken together all these observations suggest the sigma receptor as a prime candidate to be involved in the pathogenesis of mental illness, particularly schizophrenia in which hallucinations are a major clinical symptom.

Deutsch, S. I., et al. (*Clinical Neuropharmacology*, Vol. 11, No. 2, pp. 105–119 (1988)) provided a review of the literature which implicates the sigma receptor site in psychosis and anti-drug efficacy. According to Deutsch et al., certain benzomorphans which possess analgesic potency in humans are also associated with a high incidence of psychotomimetic effects. It has now been concluded that the analgesic action is associated with the levorotatory isomers of racemic mixtures of the benzomorphans, while the psychotomimetic effects are attributable to the dextrorotatory isomers in the racemic mixtures. See Haertzen, C. A., *Psychopharmacologia* 18:366–77 (1970), and Manallack, D. T., et al., *Pharmacol. Sci.* 7:448–51 (1986). Coupled with the fact that many of the in vivo effects of these dextrorotatory enantiomers and the binding of dextrorotatory tritiated SKF-10,047 are not antagonized by naloxone or naltrexone, these data strongly support the concept that the psychotomimetic effects of the dextrorotatory enantiomers are associated with the sigma receptor binding site.

Further, Su, T. P., et al. (*Life Sci.* 38:2199–210 (1986)), and Contreras, P. C., et al. (*Synapse* 1:57–61 (1987)), have established the existence of endogenous ligands for the sigma receptor, suggesting that the dysregulation of the synthesis, release, or degradation of these natural ligands may be a naturally occurring mechanism of psychosis. Accordingly, sigma receptor antagonism provides the potential for an effective antipsychotic therapeutic treatment. See Ferris, R. M., et al., *Life Sci.* 38:2329–37 (1986), and Su, T. P., *Neurosci. Let.* 71:224–8 (1986).

As further evidence of the role of the sigma receptor in psychosis, the substituted carbazole cis-9-[3-(3,5-dimethyl-1-piperazinyl)propyl]carbazole dihydrochloride (rimcazole) was identified as a potential antipsychotic agent based on its ability to antagonize apomorphine-induced mesolimbic behaviors selectively without altering the intensity of stereotypic behaviors. Further, the compound does not accelerate the rate of dopamine synthesis and does not affect dopamine-stimulated production of cAMP in homogenates of rat striatum and olfactory tubercle, thus establishing that rimcazole does not exert its action at the level of postsynaptic dopamine receptors in the mesolimbic area.

Rimcazole is able to competitively inhibit the specific binding of dextrorotatory tritiated SKF-10,047, the prototype sigma receptor agonist, suggesting that rimcazole acts at the sigma receptor site. Rimcazole, therefore, shows potential antipsychotic activity in humans, without extrapyramidal effects, pharmacological behavior which is consistent with its role as a competitive antagonist of the sigma-receptor.

Another compound, BMY 14802, has demonstrated many properties in preclinical behavioral tests which suggest its efficacy as a potential antipsychotic agent which is devoid of extrapyramidal side effects. The compound (1) did not cause catalepsy in rats; (2) does not inhibit the binding of [$^3$H] spiperone to the $D_2$ class of striatal dopamine receptors in rats; (3) did not increase the maximal density of the [$^3$H] spiperone-labeled $D_2$ site in striatum even following chronic administration (20 days) to rats; (4) does not appear to interact with the $D_1$ subclass of dopamine receptors; and (5) does not inhibit dopamine-stimulated cAMP production or the binding of [$^3$H]SCH 23390 in vitro. These data suggest that BMY 14802 has a low potential for production of tardive dyskinesia and further suggests that the antipsychotic effects would be mediated by a nondopaminergic site. Further, BMY 14802 binds with relatively high affinity to the sigma receptor, with the binding being stereoselective (the dextrorotatory enantiomer being 10 times more potent at inhibiting binding than the levorotatory enantiomer). BMY 14802 does not bind to the adrenergic, muscarinic, cholinergic, or histaminergic sites, suggesting that the compound would not be associated with unpleasant sedative and autonomic side effects.

Accordingly, compounds which bind selectively to the sigma receptor site and which antagonize this site may be expected to be useful antipsychotic drugs which are devoid of extrapyramidal effects.

The antipsychotic and anti-schizophrenia drugs that are currently in use have very strong side effects that are mainly due to their action on dopamine receptors. The side effects often involve irreversible damage to the extrapyramidal nervous system which controls movement functions of the brain. Patients under long term antischizophrenic drug treatment often develop a syndrome that involves permanent damage of their ability to control coordinated movement.

The foregoing studies have shown that the sigma binding site has the characteristics of 1) stereo-selectivity towards dextrorotatory benzomorphan opiates and insensitivity for naloxone; 2) high affinity for haloperidol and moderate to high affinity for phenothiazine antipsychotic drugs which are also known to be potent dopamine receptor blockers; and 3) insensitivity for dopamine and apomorphine. This intriguing drug selectivity profile calls for a thorough analysis of the role of sigma receptors in normal and abnormal brain function. In order to do so, it is essential that a spectrum of highly selective and potent sigma receptor active compounds be available. This invention provides such compounds and methods for identifying other drugs having such activity.

Fear, or apprehension, is characterized by the anticipation of a known danger or event. In contrast, neurotic anxiety is characterized by an apprehension with no known cause, or a maladaptive response to a trivial danger. In recent years, generalized anxiety disorder (GAD) has been characterized by psychiatrists as being chronic (continually present for at least 1 month) and exemplified by three of four psychomotor symptoms: motor tension, autonomic hyperactivity, apprehensive expectation, vigilance and scanning. Before this characterization was adopted, clinical trials of anxiolytic agents in the U.S. occurred in patients which were described variously as suffering from anxiety neurosis, anxiety with associated depression, and other such terms. Anxiety disorders affect 2–3% of the general population (the 67 million prescriptions written in 1977 for just two popular anxiolytics confirm this projected incidence). The popularity of anxiolytics attests to their ability to ameliorate the debilitating symptoms of the disease. Taylor, D. P., *FASEB J.* 2: 2445–2452 (1988).

Historically, anxiety has been treated by agents including alcohol opiates, and belladonna, which have a sedative component to their action. In the 20th century novel chemical entities were discovered which are safer for the treatment of anxiety including barbiturates, propanediol carbamates, and benzodiazepines. The pharmacological profiles of these drugs have suggested that their actions are mediated by receptors for γ-aminobutyric acid (GABA). Although the benzodiazepines present a safer alternative than meprobamate and phenobarbital, they also are sedatives. In addition, the benzodiazepines control convulsions and produce muscle relaxation, properties that are unneeded or undesirable in the treatment of anxiety. Furthermore, these drugs can interact with alcohol, with potentially disastrous consequences. Recently, it has been appreciated that the benzodiazepines produce habituation and possess a pronounced liability, for example, withdrawal symptoms after chronic use. The need for anxioselective drugs that are more selective, have fewer side effects, and present a profile consistent with safety during protracted treatment has resulted in a continuing search for such drugs. This search has led to the synthesis and evaluation of agents that possess no obvious homology with the benzodiazepines. Taylor et al., supra.

Buspirone (Buspar) was the first novel anxiolytic to be approved for clinical use in the U.S. since the benzodiazepines were introduced almost 30 years ago. The introduction of buspirone into clinical trials for the treatment of anxiety was a direct result of its efficacy in a predictive animal model for the disease—the taming of the aggressive response of rhesus monkeys to the introduction of foreign objects into their cages according to the protocol described by Tompkins, E. C. et al., *Res Commun. Psychol. Psychiatry Behav.* 5: 337–352 (1980). See Taylor et al., supra.

The preclinical screening of putative anxiolytics is dependent upon animal tests. Most of the laboratory data on new putative anxiolytics come from animal tests form two main classes. The first group of tests are based on conflict or conditioned fear. The second group of tests are based upon anxiety generated by novel situations. Although these tests differ in the way anxiety is produced, there has been surprising agreement amongst them in the classification of drugs as anxiolytic or anxiogenic. See File, S. E., *TINS* 10:461–463 (1987).

In two particular tests for anxiolytic activity, it is assumed that the anticipation of punishment causes a reduction in a response associated with the punishment. Conversely, anxiolytic agents that reduce anxiety result in an increased response rate. In the Geller-Seifter test, the rat receives food reward for pressing a lever, but also receives an electric footshock, which has the effect of suppressing the response. This punished schedule alternates with an unpunished schedule wherein electric footshocks are not administered. During this unpunished schedule, lever-pressing is still rewarded. In the Vogel test, a rat is allowed to drink water, but also receives an electric shock through the water spout or the bars of the floor. In both the Vogel and Geller-Seifter tests, a measure of unpunished response is obtained in order to allow assessment of any non-specific stimulant or sedative drug effects or any changes in food or water intake. In both of these tests, benzodiazepines enhance the response rate in the punished periods, without increasing the rate of response in the absence of shock. While these tests are valid tests of anxiety, the only means of assessing them has been pharmacological. Taylor et al., supra.

A less widely used test utilizes punished locomotion, wherein a measure of unpunished crossing is obtained according to the rate at which a mouse crosses from one metal plate to another, wherein footshocks are administered whenever the mouse crosses. Although less widely utilized to test anxiolytic agents, this test has been able to detect drug-induced increases and decreases in anxiety by manipulating the shock level. File, S. E., *J. Neurosci Methods* 2:219–238 (1980).

The social interaction test of anxiety (File, supra; Jones, B. J. et al., *Br. J. Pharmacol.* 93:985–993 (1988) exploits the uncertainty and anxiety generated by placing rats in an unfamiliar environment and in bright light. The dependent variable is the time that pairs of male rats spend in active social interaction (90% of the behaviors are investigatory in nature). Both the familiarity and the light level of the test arena may be manipulated. Undrugged rats show the highest level of social interaction when the test arena is familiar and is lit by low light. Social interaction declines if the arena is unfamiliar to the rats or is lit by bright light. Anxiolytic agents prevent this decline. The overall level of motor activity may also be measured to allow detection of drug effects specific to social behaviors.

The social interaction test of anxiety is one of the few animal tests of anxiety that has been validated behaviorally. Other behavioral measures indicative of anxiety and stress (e.g. defecation, self-grooming and displacement activities) were correlated with the reductions in social interaction; and other causes of response change (e.g. exploration of the environment, odor changes) were excluded. In order to validate the test physiologically, ACTH and corticosterone levels and changes in hypothalamic noradrenaline also were measured. File, *TINS* 10: 461–463 (1987).

Another test of anxiety that exploits the anxiety generated by a novel situation is the "elevated plus maze." In this test, the anxiety is generated by placing the animals on an elevated open arm. Height, rather than the light level, is responsible for generating behavioral and physiological changes. The apparatus is in the shape of a plus with two open and two enclosed arms. The rat has free access to all arms on the apparatus. Anxiolytic activity may be measured by the percentage increase in the time that the test animal spends on the open arms and the number of entries onto the open arms. This test has also been validated behaviorally and physiologically.

Agents which have been determined to have anxiolytic activity include the carbazole derivative 9-[3-(3,5-cis-dimethylpiperazino)propyl]carbazole having the Formula (II):

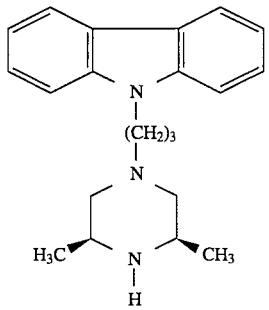

(II)

and pharmaceutical compositions thereof. See U.S. Pat. No. 4,400,383 (1983).

Serotonin receptor antagonists are also known to be useful for the treatment of anxiety. See Kahn, R. S. et al., *J. Affective Disord.* 8:197–200 (1987); Westenberg, H. G. M. et al., *Psychopharmacol. Bull.* 23:146–149 (1987).

SUMMARY OF THE INVENTION

The invention relates to novel N,N'-disubstituted guanidines which bind to sigma receptor sites, especially those which do so selectively.

The invention also relates to a novel class of N,N'-disubstituted guanidines which are radioactively tagged and which are useful for assaying in vitro the sigma receptor binding activity of organic compounds.

The invention also relates to pharmacological compositions comprising certain of the aforesaid N,N'-disubstituted guanidines having sigma receptor binding activity and the use thereof to treat or prevent psycosis, depression, hypertension or anxiety.

The invention also relates to a method for determining the sigma receptor binding activity of organic compounds.

The invention also relates to an in vitro screening method for assaying compounds having sigma receptor activity and utility as antipsychotic, antidepressant, antihypertensive and anxiolytic drugs.

The invention also relates to a method of determining the relationship of abnormal psychotic-like behavior in a mammal displaying such behavior to sigma receptor system dysfunction.

The substituted guanidines of the invention have the Formula (I):

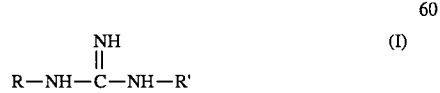

(I)

wherein R and R' are an alkyl group of at least 4 carbon atoms, a cycloalkyl group of at least 3 carbon atoms, a carbocyclic aryl group of at least 6 carbon atoms, alkaryl or aralkyl of at least 6 carbon atoms and containing 1–3 separate or fused rings, a heterocyclic ring or a heteroaryl group, and wherein each of R and R' may be substituted in 1–3 positions, or wherein R and R' together with the guanidine group to which they are attached form a saturated or unsaturated cyclic ring containing at least 2 carbon atoms exclusive of the guanidine carbon atom, and wherein said cyclic ring may be substituted with one or more alkyl groups of 1–6 carbon atoms, carbocyclic aryl groups of at least 6 carbon atoms, cycloalkyl groups of 3–12 carbon atoms, or 1–2 fused aromatic rings, and further wherein said N,N'-disubstituted guanidine exhibits a high affinity for the sigma receptor. Preferably, such N,N'-disubstituted guanidines also exhibit activity in one or more of the animal models disclosed herein.

In particular, the invention relates to N,N'-disubstituted guanidines of the Formula (I), above, wherein R and R' each are adamantyl, cyclohexyl, coumarinyl, norbornyl, isobornyl, or a monocyclic carbocyclic aryl of at least 6 carbon atoms.

The invention also relates to substituted guanidines having the Formula (III):

(III)

wherein

X and Y are independently a branched or straight chain $C_1$–$C_{12}$ alkylene or a branched or straight chain $C_2$–$C_{12}$ unsaturated alkylene or wherein one of X and Y is a single bond;

R and R' are independently hydrogen, a cycloalkyl group of at least 3 carbon atoms, a carbocyclic aryl group of at least 6 carbon atoms, aralkyl of at least 6 carbon atoms and containing 1–3 separate or fused rings, a heterocyclic ring or a heteroaryl group, and wherein each of R and R' may be substituted in 1–3 positions, or wherein R and R' together with the guanidine group to which they are attached form a saturated or unsaturated cyclic ring containing at least 2 carbon atoms exclusive of the guanidine carbon atom, and wherein said cyclic ring may be substituted with one or more alkyl groups of 1–6 carbon atoms, carbocyclic aryl groups of at least 6 carbon atoms, cycloalkyl groups of 3–12 carbon atoms, or 1–2 fused aromatic rings. Preferably, said N,N'-disubstituted guanidine exhibits a high affinity for the sigma receptor.

Preferably, X and Y are $C_1$–$C_4$ alkylene groups. Also contemplated for use in the claimed invention are the N,N'-disubstituted guanidines having Formulae (I) and (III), wherein one or two $C_1$–$C_6$ lower alkyl groups are substituted on N and/or N'.

The invention also relates to compounds having the Formula (IV):

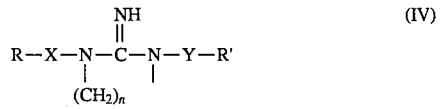

(IV)

wherein n is 2, 3, 4 or 5;

X and Y are independently a single bond, a branched or straight chain $C_1$–$C_{12}$ alkylene or a branched or straight chain $C_2$–$C_{12}$ alkylene;

R and R' are independently hydrogen, a cycloalkyl group of at least 3 carbon atoms, a carbocyclic aryl group of at least 6 carbon atoms, aralkyl of at least 6 carbon atoms and containing 1–3 separate or fused rings, a heterocyclic ring, and wherein each of R and R' may be substituted in 1–3 positions, or wherein R and R' together with the guanidine group to which they are attached form a saturated or unsaturated cyclic ring containing at least 2 carbon atoms exclusive of the guanidine carbon atom, and wherein said cyclic ring may be substituted with one or more alkyl groups of 1–5 carbon atoms, carbocyclic aryl groups of at least 6 carbon atoms, cycloalkyl groups of 3–12 carbon atoms, or 1–2 fused aromatic rings. Preferably, said compound exhibits a high affinity for the sigma receptor. Also preferable is where R and R' are m-ethylphenyl, X and Y are single bonds and n is 2, e.g., N,N'-di(m-ethylphenyl)-2-iminoimidazolidine.

The invention also relates to tritiated derivatives of the above-listed N,N'-disubstituted guanidines wherein at least one of the ring carbon atoms of R and R' bears at least one radioactive atom, preferably a tritium atom The invention also relates to a method of determining the sigma brain receptor binding activity of an organic compound which comprises the steps of:

a) contacting in an aqueous medium a known amount of isolated mammalian brain membrane which has sigma receptor-type binding activity, with a mixture of (i) a radio-labeled N,N'-disubstituted guanidine which selectively binds sigma brain receptors, in a known amount capable of being bound to the sigma receptors of that brain membrane; and (ii) varying known amounts of a water soluble organic compound to be assayed for sigma receptor binding activity;

b) separating the brain membrane from the radio-labeled compound which is not bound to the brain membrane in step a);

c) determining, from the molar relationship of the proportion of bound radio-labeled compound which is separated in step b) to the molar amount of the organic compound employed in step a), the sigma receptor binding activity of that organic compound.

The invention also relates to a method of determining the relationship of abnormal psychotic-like behavior in a mammal displaying such behavior to sigma receptor dysfunction, which comprises administering thereto a sigma brain receptor-modulating amount of a water-soluble N,N'-disubstituted guanidine which displaces in vitro N,N'-di-(4-[$^3$H]-2-methylphenyl)-guanidine bound to mammalian brain membrane, effective to alter the sigma brain receptor-modulated mental activity of that mammal.

By the present invention, there is provided a means for identifying compounds which bind competitively and selectively to the sigma receptor site. Accordingly, the invention provides compounds, pharmaceutical compositions, and the use of same for treatment of psychoses, depression, hypertension or anxiety. Selective sigma receptor binding is of particular value in reducing or eliminating undesirable extrapyramidal side effects associated with present antipsychotic medications.

It has been discovered further that certain N,N'-disubstituted guanidines are potent anxiolytics, and at the same time, are substantially non-sedative in an animal model. Therefore, these N,N'-disubstituted guanidines are useful for the treatment or prophylaxis of anxiety in animals, i.e., humans.

BRIEF DESCRIPTION OF THE DRAWINGS

FIG. 9 is a graphical representation of the data resulting from the in vivo s.c. administration of N-cyclohexyl-N'-(o-totyl)guanidine, in comparison to controls, on mouse behavior in the black:white test box.

FIG. 11 is a graphical representation of data resulting from the in vivo s.c. administration of N-(exo-2-norbornyl)-N'-(2-methylphenyl)guanidine, in comparison to controls, on mouse behavior in the black:white test box.

FIG. 13 is a graphical representation of the data resulting from the oral administration of N-cyclohexyl-N'-(2-methylphenyl)guanidine, in comparison with controls, on mouse behavior in the black:white test box.

DESCRIPTION OF THE PREFERRED EMBODIMENTS

Figure 1:
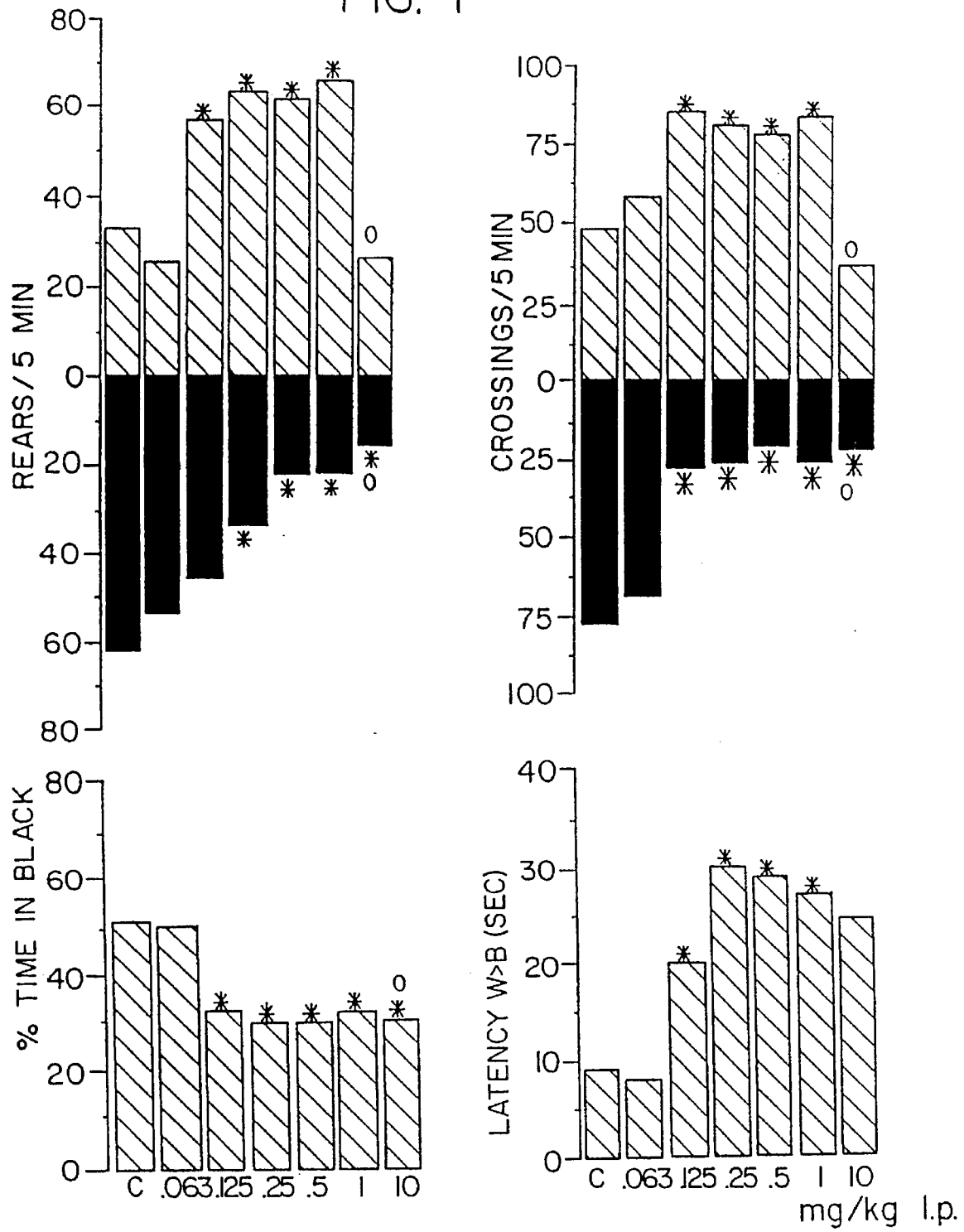
FIG. 1 is a graphical representation of the data resulting from the in vivo subcutaneous (s.c.) administration of diazepam on mouse behavior in the black:white test box.

We have discovered that the disubstituted guanidines of this invention have sigma receptor binding activity, as evidenced by their ability to displace from guinea pig membrane binding sites [$^3$H]-1,3-di-ortho-tolyl-guanidine(N,N'-di-(4-[$^3$H]-2-methylphenyl)-guanidine ([$^3$H]—DTG]) which has the Formula (IV):

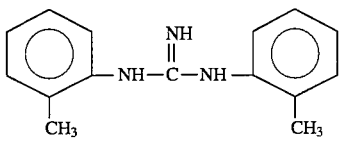

This compound binds reversibly, saturably, selectively and with high affinity to sigma receptor binding sites in guinea pig brain membrane homogenates and slide-mounted rat and guinea pig brain sections. We have established that (+)-[$^3$H] 3-PPP binds to the same sites. Availability of the selective sigma ligands of this invention facilitates characterization of sigma receptors in vivo and in vitro.

The preferred N,N'-disubstituted guanidines of this invention are those of the Formula (I):

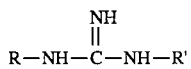

wherein R and R' each are an alkyl group of at least 4 carbon atoms or carbocyclic aryl groups of at least 6 carbon atoms, e.g., R and R', which can be the same or different, are alkyl of 4 or more carbon atoms, e.g., a 4 to 12, preferably a straight chain alkyl and more preferably a 4 to 8 carbon atom alkyl group, for example, butyl, isobutyl, tert-butyl, amyl, hexyl, octyl, nonyl and decyl; cycloalkyl of 3 to 12 carbon atoms, e.g., cyclopropyl, cyclobutyl, cyclopentyl, cyclohexyl, cycloheptyl, 1,4-methylene-cyclohexanyl, adamantyl, norbornyl, isobornyl, cyclopentylmethyl, cyclohexylmethyl, 1- or 2-cyclohexylethyl and 1-, 2- or 3-cyclohexylpropyl; carbocyclic aryl, alkaryl or aralkyl, e.g., of up to 18 carbon atoms and containing 1–3 separate or fused aromatic rings, e.g., phenyl, benzyl, 1- and 2-phenylethyl, 1-, 2-, or 3-phenylpropyl; o-, m- or p-tolyl, m,m'-dimethylphenyl, o-, m- or p-ethylphenyl, m,m'diethylphenyl, m-methyl-m'-ethylphenyl and o-propylphenyl, naphthyl, 2-naphthyl, biphenyl; and heterocyclic rings, e.g. 3-, 4-, 5-, 6-, 7-, and 8-coumarinyl; 2- and 4-pyridyl, pyrrolyl especially 2- and 3-N-methylpyrrolyl, pyrrolidinyl, 2- and 3-furanyl, 2- and 3-thiophenyl, 2- and 3-benzofuranyl, 2-benzoxazolyl, pyrazinyl, piperazinyl, pyrimidyl, 2-, 4- and 5- thiazolyl, 2-, 4- and 5- oxazolyl, 2-, 4- and 5-imidazolyl, 2- and 3-indolyl, and 2-4-benzothiazolyl, thienyl, benzofuranyl and morpholino.

Additionally, 1, 2, 3 or more substituents which do not adversely affect the activity of the N,N'-disubstituted guanidine moiety may be present on one or both of the R and R' hydrocarbon groups thereof, e.g., alkyl of 1–8 carbon atoms, e.g., methyl, ethyl; hydroxyalkyl of 1–8 carbon atoms; halo, e.g., chloro, bromo, iodo, fluoro; hydroxy; nitro; azido, cyano; isocyanato; amino; lower-alkylamino; di-lower-alkylamino; trifluoromethyl; alkoxy of 1–8 carbon atoms, e.g., methoxy, ethoxy and propoxy; acyloxy, e.g., alkanoyloxy of 1–8 carbon atoms, e.g., acetoxy and benzoxy; amido, e.g., acetamido, N-ethylcetamido; carbamido, e.g., carbamyl, N-methylcarbamyl, N,N'-dimethylcarbamyl; etc.

Especially preferred are compounds of Formula I wherein R and R' each are cyclohexyl, norbornyl, adamantan-1-yl, adamantan-2-yl, 8-coumarinyl, or phenyl groups. Such phenyl groups, which need not necessarily be identical, may be substituted with one or more of the foregoing substituents, for example, in the o-, m- or p- position or the 2,2-, 2,4- or 3,5-position, when the phenyl group is disubstituted or R is as herein defined and R' is adamantyl. Specific examples are those wherein R and R' both are phenyl or o-tolyl; R is o-tolyl and R' is p-bromo-o-tolyl, p-CF$_3$-o-tolyl, p-iodo-o-tolyl, o-iodo-phenyl, p-azido-o-tolyl, cyclohexyl or adamantyl; and R is phenyl and R' is p-bromo-o-tolyl, p-iodo-o-tolyl, m-nitro-phenyl or o-iodo-phenyl.

The highly active disubstituted guanidines of this invention have substantially the same stereoconfiguration as (+)3-PPP with phenyl axial and with SKF 10,047 with the piperidine ring in a skew-boat form and N-allyl axial. This similarity in spacial configuration, i.e., as demonstrated by computer modeling, of compounds having sigma receptor binding activity provides a screening technique for predicting the probable level of sigma receptor binding activity of other N,N'-disubstituted guanidines. Computer assisted molecular modifying can be used to determine the molecular similarity of the various species in three dimensions.

Examples of those compounds which have been isolated and/or prepared and found to possess the aforesaid in vitro [$^3$H]DTG displacement activity are N,N'-dibutylguanidine, N,N'-diphenylguanidine, N,N'-di-o-tolylguanidine, N,N'-di-(2-methyl-4-bromo-phenyl)guanidine, N,N'-di-(2-methyl-4-iodophenyl)guanidine, N-(2-methyl-azidophenyl)-N'-(2-methylphenyl)guanidine, N,N'-diadamantylguanidine, N-adamantyl-N'-(2-methylphenyl)guanidine, N-(2-iodophenyl)-N'-(2-methylphenyl)guanidine, N-(2-methyl-4-nitrophenyl)-N'-(2-methylphenyl)guanidine, N,N'-di-(2,6-dimethylphenyl)guanidine, N-(2,6-dimethylphenyl)-N'-(2-methylphenyl)guanidine, N-(adamantyl)-N'-(cyclohexyl)guanidine, N,N'-di(cyclohexyl)guanidine, N-(2-iodophenyl)-N'-(adamantyl)guanidine, N-(2-methylphenyl)-N'-cyclohexyl-guanidine, N-adamantyl-N'-phenylguanidine, N,N'-di-(m-n-propylphenyl)guanidine, N,N'-di-(1-tetralinyl)guanidine, N-(3,5-dimethyl-1-adamantanyl)-N'-(o-tolyl)guanidine, N-(3,5-dimethyl-1-adamantanyl)-N'-(o-iodophenyl)guanidine, N-(1-adamantyl)-N'-(o-nitrophenyl)guanidine, N,N'-di-((±)-endo-2-norbornyl)guanidine, N-(exo-2-isobornyl)-N'-(o-iodophenyl)guanidine, N,N'-di-(exo-2-norbornyl)guanidine, N-(exo-2-isobornyl)-N'-(o-tolyl)guanidine, N-(o-iodophenyl)-N'-(t-butyl)guanidine, N,N'-dibenzylguanidine, N-(adamant-1-yl)-N'-(o-isopropylphenyl)guanidine, N-(adamant-1-yl)-N'-(p-bromo-o-tolyl)guanidine, N-(cyclohexyl)-N'-(p-bromo-o-tolyl)guanidine, and N-(adamant-2-yl)-N'-(p-iodophenyl)guanidine.

Among the compounds tested to date, some of those having the highest sigma receptor binding activity are those of Formula I wherein one of R and R' is adamantyl and the other is also adamantyl or o-substituted phenyl. Therefore, the preferred compounds of this invention include those wherein R and R$^1$ have those values, i.e., wherein the other of R and R$^1$ is, e.g., o-lower alkyl phenyl, wherein alkyl is of 1–4 carbon atoms, e.g., CH$_3$, C$_2$H$_5$, i-C$_3$H$_7$, o-halophenyl wherein halo is Cl, Br, I or F, o-nitro-o-amino, o-carbo-lower alkoxy, e.g., COOCH$_3$, o-amino, e.g., —CONH$_2$, o-sulfato, o-carboxy, o-acyl, e.g., acetyl, o-CF$_3$, o-sulfamido and o-lower-alkoxy, e.g., o-methoxy, phenyl or another phenyl group ortho substituted by any other substituent of a molecular weight less than 150.

Especially preferred N,N'-disubstituted guanidine compounds which have high binding to the sigma receptor include N-(2 -iodophenyl)-N'-(adamant-1-yl)guanidine (AdIpG, IC$_{50}$=6.2 nM); N-(o-tolyl)-N'-(adamant-1-yl)guanidine (AdTG, IC$_{50}$=7.6 nM); N,N'-di-(adamant-1-yl)guanidine (DAG, IC$_{50}$=16.5 nM); N-cyclohexyl-N'-(2-methylphenyl)-guanidine (IC$_{50}$=13 nM); N-(adamant-1-yl)-N'-cyclohexylguanidine (IC$_{50}$=12.5 nM); N-(adamant-2-yl)-N'-(2-iodophenyl)guanidine (IC$_{50}$=3.5 nM); N-(adamant-2- yl)-N'-(2-methylphenyl)guanidine ($IC_{50}$=7.0 nM); N-(exo-2-norbornyl)-N'-(2-methylphenyl)guanidine ($IC_{50}$=7.0nM); N-((±)-endo-2-norbornyl)-N'-(2-methylphenyl)guanidine ($IC_{50}$=6.0 nM); N-(exo-2-norbornyl)-N'-(2-iodophenyl)guanidine ($IC_{50}$=4.0 nM); N-((±)-endo-2-norbornyl)-N'-(2-iodophenyl)guanidine ($IC_{50}$=5.0 nM); N,N'-di-(o-tolyl)guanidine ($IC_{50}$=32 nM); N-(o-tolyl)-N'-(o-iodophenyl)guanidine ($IC_{50}$=21 nM); N,N'-di-(p-bromo-o-methylphenyl)guanidine ($IC_{50}$=37 nM); N,N'-di-(m-n-propylphenyl)guanidine ($IC_{50}$=36 nM); N-(o-tolyl)-N'-(p-nitro-o-tolyl)guanidine ($IC_{50}$=37 nM); N,N'-di-(1-tetralinyl)guanidine ($IC_{50}$=58 nM); N-(o-tolyl)-N'-(o-xylyl)guanidine ($IC_{50}$=70 nM); N,N'-di-(o-xylyl)guanidine ($IC_{50}$=90 nM); N,N'-di-(cyclohexyl)guanidine ($IC_{50}$=71 nM); N-(3,5-dimethyladamantan-1-yl)-N'-(o-tolyl)guanidine ($IC_{50}$=15 nM); N-(3,5-dimethyl-1-adamantanyl)-N'-(o-iodophenyl)guanidine ($IC_{50}$=16 nM); N-(1-adamantyl)-N'-(o-nitrophenyl)guanidine ($IC_{50}$=30 nM); N,N'-di-((±)-endo-2-norbornyl)guanidine ($IC_{50}$=16 nM); N-(exo-2-isobornyl)-N'-(o-iodophenyl)guanidine ($IC_{50}$=18 nM); N,N'-di-(exo-2-norbornyl)guanidine ($IC_{50}$=22 nM); N-(exo-2-isobornyl)-N'-(o-tolyl)guanidine ($IC_{50}$=25 nM); N-(o-iodophenyl)-N'-(t-butyl)guanidine ($IC_{50}$=20 nM); N,N'-dibenzylguanidine ($IC_{50}$=90 nM); N-(adamant-1-yl)-N'-(o-isopropylphenyl)guanidine ($IC_{50}$=24 nM); N-(adamant-1-yl)-N'-(p-bromo-o-tolyl)guanidine ($IC_{50}$=2.7 nM); N-(cyclohexyl)-N'-(p-bromo-o-tolyl)guanidine ($IC_{50}$=5.5 nM); N-(4-azido-2-methylphenyl)-N'-(2-methylphenyl)guanidine ($IC_{50}$=20 nM); N-(2-methyl-4-nitro-5-bromophenyl)-N'-(2-methyl-4,5-dibromophenyl)guanidine; N,N'-di-(o -iodophenyl)guanidine ($IC_{50}$=13 nM); N,N'-di-(3-methylphenyl)guanidine ($IC_{50}$=43 nM); N,N'-di-(m-ethylphenyl)-2-imino-imidazolidine ($IC_{50}$=70 nM); N-(4-nitro-2-methylphenyl)-N'-(2-methylphenyl)guanidine ($IC_{50}$=37 nM); N-(1-naphthyl)-N'-(2-iodophenyl)guanidine ($IC_{50}$=40.1 nM); N,N'-di-(4-indanyl)guanidine ($IC_{50}$=28.5 nM); N-(adamantan-1-yl)-N'-(2-trifluoromethylphenyl)guanidine ($IC_{50}$=7.44 nM); N-(adamantan-1-yl)-N'-(2-methylphenyl)-N'-methylguanidine ($IC_{50}$=22.6 nM); N-(adamantan-1-yl)-N'-(6-coumarinyl)guanidine ($IC_{50}$=21.9 nM); N-(adamantan-1-yl)-N'-(2,4-difluorophenyl)guanidine ($IC_{50}$=8.92 nM); and N-(adamantan-1-yl)-N'-(2-trifluoromethyl-4-fluorophenyl)guanidine ($IC_{50}$=4 nM).

The level of sigma receptor activity of the disubstituted guanidines can also be determined in vivo in a discriminative stimulus property test employing rats trained to discriminate between intraperitoneal injections of cyclazocine (2.0 mg/kg) and saline in a discrete-trial avoidance paradigm with sessions of 20 trials each. For example, ditolylguanidine (DTG) and diphenylguanidine (DPG) were fully substitutable for cyclazocine at the same concentrations. (Holtzman, S. G., Emery University, Atlanta, Ga., private communication.)

Although the discussion hereinafter of the experiments below relates to certain of these selective sigma receptor ligands, viz., the N,N'-disubstituted guanidines of Table I below, the activity and utility of that compound apply comparably to the other disubstituted guanidines which compete with and displace in vitro N,N'-di-(4-[$^3$H]-2-methylphenyl)-guanidine bound in vitro to isolated guinea pig brain membrane.

In carrying out the sigma receptor binding activity measurement method of this invention, a known amount of a mammalian brain membrane, e.g., human or other primate, porcine, rodent, e.g., rat or guinea pig, which has SKF 10,047 and like psychotomimetic benzomorphan binding activity is contacted in a suitable aqueous vehicle, e.g., physiological saline solution, with a mixture, usually in a solution in a suitable aqueous vehicle of (i) a tritium-labeled N,N'-disubstituted guanidine of this invention having sigma receptor binding activity, in an mount capable of being fully bound to the above said amount of membrane and (ii) a water soluble organic compound whose sigma receptor activity is to be assayed, in known mounts, sufficiently varied to obtain a dose-response curve. The techniques for obtaining a dose-response curve are standard and well known to those skilled in the art. Typically, one could employ molar amounts varying as much as from $10^{-4}$ to $10^4$ of the molar amount of the tritium labeled compound present in the mixture, e.g., employing from 10 to 120 and preferably 30 to 90 such mixtures.

If the organic compound being assayed has sigma receptor binding activity, a portion of the tritium labeled compound which, in the absence of the organic compound would bind to the membrane remains unbound and is thus separable from the membrane. The amount which remains unbound is proportional to the sigma receptor binding activity of the organic compound and the molar ratio thereof in the mixture to the tritium labeled compound.

The two compounds can be employed at any convenient collective concentration, e.g., from $10^{-8}$ to $10^3$ nM.

In the next step, the membrane is separated from and washed until free of the solution in which step (a) is conducted. In the next step, the amount of tritium labeled compound which is thus separated from the membrane is determined, e.g., by measuring the collective radioactivity level of the separated solution and wash water and comparing that radioactivity to that obtained when the foregoing steps are conducted with the same amount of tritium-labeled N,N'-disubstituted guanidine in the absence of the organic compound.

In the next step of the method, the activity of sigma receptor binding activity of the organic compound is determined from the dose response curve thus obtained.

Although tritium radiolabels are preferred, any radiolabel which can be substituted on the N,N'-disubstituted guanidines of the invention may be employed, e.g., $^{11}C$, $^{14}C$, $^{18}F$, $^{125}I$, $^{131}I$, $^{15}N$, $^{35}S$, and $^{32}P$.

All of the foregoing steps are conventional and have been employed in the prior art with other types of $^3$H-labeled compounds having sigma receptor binding activity. The method of this invention is, however, unique in that the tritium-labeled N,N'-disubstituted guanidines of this invention are highly selective to binding by the sigma receptors and therefore will not compete with organic compounds which bind to other brain receptors.

In carrying out the method of treatment aspect of this invention, e.g., treating a human being suffering from a psychotic mental illness associated with hallucinations, or suffering from depression, hypertension or anxiety, there is administered thereto an effective amount of a water-soluble N,N'-disubstituted guanidine which has high binding to the sigma receptor. When treating psychosis, the compound is an antagonist to the sigma receptor binding activity of a hallucinogenic benzomorphan. Preferably, the guanidine is a compound of Formulae I, III or IV wherein R and R' each is an alkyl group of at least 4 carbon atoms, a cycloalkyl group of 3 to 12 carbon atoms or a carbocyclic aryl group of at least 6 carbon atoms. In preferred aspect, the human being is schizophrenic; in another preferred aspect, the compound is N,N'-di-(2-methylphenyl)-guanidine, N-(adamantyl)-N'-(cyclohexyl)guanidine, N-adamantyl-N'-(2-methylphenyl)guanidine, N-(1-adamantyl)-N'-(o-iodophenyl)guanidine, N-(2-adamantyl)-N'-(o-iodophenyl)guanidine, N-cyclohexyl-N'-(2-methylphenyl)guanidine, N,N'-di-(cyclohexyl)guanidine, N,N'-di-(2-adamantyl)guanidine, N,N'-di-(m-n-propylphenyl)guanidine, N-(o-tolyl)-N'-(p-nitro-o-tolyl)guanidine, N,N'-di-(1-tetralinyl)guanidine, N-(o-tolyl)-N'-(o-xylyl)guanidine, N,N'-di-(o-xylyl)guanidine, N-(3,5-dimethyladmantan-1yl)-N'-(o-tolyl)guanidine, N-(3,5-dimethyladamantan-1-yl)-N'-(o-iodophenyl)guanidine, N-(1-adamantyl)-N'-(o-nitrophenyl)guanidine, (+) and (−)N-(exo-2-norbornyl)-N'-(2-iodophenyl)guanidine, (+) and (−)N-(endonorbornyl)-N'-(o-tolyl)guanidine, (+) and (−)N-(exonorbornyl)-N'-(o-tolyl)guanidine, (+) and (−)N,N'-di(endonorbornyl)guanidine, (+) and (−)N-(exoisobornyl)-N'-(o-iodophenyl)guanidine, (+) and (−)N,N'-di-(exonorbornyl)guanidine, N-(o-iodophenyl)-N'-(t-butyl)guanidine, N,N'-dibenzylguanidine, N-(adamant-1-yl)-N'-(o-isopropylphenyl)guanidine, N-(adamant-1-yl)-N'-(p-bromo-o-tolyl)guanidine, N-cyclohexyl-N'-(p-bromo-o-tolyl)guanidine, N-(adamant-2-yl)-N'-(p-iodophenyl)guanidine, N,N'-di(o-methylbenzyl)guanidine, N,N'-di(1-adamantanemethyl)guanidine, N-(adamantan-1-yl)-N'-(2-trifluoromethylphenyl)-guanidine, N-(adamantan-1-yl)-N'-(2,4-difluoromethylphenyl)guanidine, and N-(adamantan-1-yl)-N'-(2-trifluoromethyl-4-fluorophenyl)guanidine; or a corresponding compound bearing 1, 2, 3 or more additional or other substituents on one or both hydrocarbon groups, e.g., alkyl of 1–8 carbon atoms, e.g., methyl-, ethyl; halo, e.g., chloro, bromo, iodo, fluoro; nitro; azido; cyano; isocyanato; amino; lower-alkylamino; di-lower-alkylamino; trifluoromethyl; alkoxy of 1–8 carbon atoms, e.g., methoxy, ethoxy and propoxy; acyloxy, e.g., alkanoyloxy of 1–8 carbon atoms, e.g., acetoxy and benzoyl; amido, e.g., acetamido, N-ethylacetamido; carbamido, e.g., carbamyl, N-methylcarbamyl, N,N'-dimethyl carbamyl; etc.

N,N'-disubstituted guanidines, e.g., of Formulae I, III and IV, can act in an agonistic, antagonistic or inverse agonistic manner in relation to the prototypical sigma benzomorphans. Those which act as antagonists can therefore be expected to affect pupil size, heart rate and mentation in a direction opposite that caused by benzomorphans which can be determined by standard tests in laboratory animals. The type and level of activity for a given dosage of each compound can be conventionally determined by routine experimentation using well known pharmacological protocols for each of the activities; the corresponding indications treatable at that dosage will be well known to skilled workers based on the pharmacological results. The compounds of this invention are particularly noteworthy for their antipsychotic activity to treat psychotic conditions, e.g., schizophrenia, by analogy to the known agents prolixin and haloperidol and for diagnosing sigma receptor intoxicated conditions.

The invention is also related to the discovery that N,N'-disubstituted guanidines having a high affinity for the sigma receptor are anxiolytic, and at the same time, are substantially non-sedative in an animal model. The term "high affinity to sigma receptor" means the compound exhibits an $IC_{50}$ of less than 100 nM in a sigma receptor binding assay, preferably against $^3$H—DTG as disclosed in the examples, below. Alternatively, the compounds may be tested against (+)-[$^3$H]3-PPP as described by Largent, B. L., et al., *Mol. Pharmacol.* 32:772–784 (1987); Largent B. L., et al., *Eur. J. Pharmacol.* 155:345–347 (1988); and Wikstrom, H., et al., *J. Med. Chem.* 30:2169–2174 (1987). The values of $IC_{50}$ obtained by screening against $^3$H—DTG and (+)-[$^3$H]3-PPP are well correlated. See Weber, E. et al., *Proc. Natl. Acad. Sci. USA* 83: 8784–8788 (1986).

These N,N'-disubstituted guanidines exhibit anxiolytic activities of generally 100–1000 times greater than that of benzodiazepines. However, unlike benzodiazepines, the N,N'-disubstituted guanidines employed in this invention are non-sedative. Therefore, these N,N'-disubstituted guanidines are particularly useful for the treatment or prevention of anxiety in animals.

Recent work by the inventors has shown that sigma receptor active drugs including the diaryl-guanidines can block acetylcholine release induced by serotonin acting at $5HT_3$ receptors in the guinea pig ileum myenteric plexus (Campbell et al., *J. Neurosci.* 9:3380–3391 (1989)). The sigma receptor active drugs act in a non-competitive manner to block acetylcholine release stimulated by $5HT_3$ receptor activation. Work by others has shown that compounds acting as competitive antagonists at $5HT_3$ receptors have anxiolytic activity (Jones et al., *Br. J. Pharmacol.* 93:985–993 (1988)). Therefore, the inventors reasoned that non-competitive antagonists of $5HT_3$ receptor-induced acetylcholine release might also be anxiolytic. This invention shows that certain sigma receptor active N,N'-disubstituted guanidines indeed have potent anxiolytic activity.

Disubstituted guanidines are the subject of U.S. Pat. No. 4,709,094, whose disclosure is incorporated herein by reference. As a class, these compounds are described in this patent as exhibiting a highly selective binding activity to the sigma brain receptor.

Certain specific members of this class of disubstituted guanidines, i.e., those demonstrating a high affinity for the sigma receptor, are useful for the treatment or prophylaxis of anxiety in an individual susceptible to anxiety. Individuals susceptible to anxiety are those who have experienced a plurality of prior episodes of GAD.

The anxiolytic activity of any particular N,N'-disubstituted guanidine may be determined by use of any of the recognized animal models for anxiety. A preferred model is described by Jones, B. J. et al., *Br. J. Pharmacol.* 93:985–993 (1988). This model involves administering the compound in question to mice which have a high basal level of anxiety. The test is based on the finding that such mice find it aversive when taken from a dark home environment in a dark testing room and placed in an area which is painted white and brightly it. The test box has two compartments, one white and brightly illuminated and one black and non-illuminated. The mouse has access to both compartments via an opening at floor level in the divider between the two compartments. The mice are placed in the center of the brightly illuminated area. After locating the opening to the dark area, the mice are free to pass back and forth between the two compartments. Control mice tend to spend a larger proportion of time in the dark compartment. When given an anxiolytic agent, the mice spend more time exploring the more novel brightly lit compartment and exhibit a delayed latency to move to the dark compartment. Moreover, the mice treated with the anxiolytic agent exhibit more behavior in the white compartment, as measured by exploratory rearings and line crossings. Since the mice can habituate to the test situation, naive mice should always be used in the test. Five parameters may be measured: the latency to entry into the dark compartment, the time spent in each area, the number of transitions between compartments, the number of lines crossed in each compartment, and the number of rears in each compartment. As disclosed more fully below in the examples, the administration of several N,N'-disubstituted guanidines has been found to result in the mice spending more time in the larger, brightly lit area of the test chamber. Unlike diazepam, the N,N'-disubstituted guanidines did not cause significant decreases in the numbers of line crossings and rears. Thus, these N,N'-disubstituted guanidines exhibit potent anxiolytic activity, and at the same time, are non-sedating.

In the light/dark exploration model, the anxiolytic activity of a putative agent can be identified by the increase of the numbers of line crossings and rears in the light compartment at the expense of the numbers of line crossings and rears in the dark compartment, in comparison with control mice.

A second preferred animal model is the rat social interaction test described by Jones, B. J. et al., supra, wherein the time that two mice spend in social interaction is quantified. The anxiolytic activity of a putative agent can be identified by the increase in the time that pairs of male rats spend in active social interaction (90% of the behaviors are investigatory in nature). Both the familiarity and the light level of the test arena may be manipulated. Undrugged rats show the highest level of social interaction when the test arena is familiar and is lit by low light. Social interaction declines if the arena is unfamiliar to the rats or is lit by bright light. Anxiolytic agents prevent this decline. The overall level of motor activity may also be measured to allow detection of drug effects specific to social behaviors.

As noted above, the compounds of this invention are useful as anti-hypertensive agents and can be used in the same manner as known antihypertensive agents, e.g., methyldopa, metoprolol tartrate and hydralazine hydrochloride.

Like guanidines generally and N,N'-diphenyl-guanidine specifically, the disubstituted guanidines of this invention, including those of Formulae I, III and IV, are accelerators for the vulcanization of rubbers, e.g., natural rubbers and epoxy group-containing acrylic rubber, and can be used for such purpose in the same manner as N,N'-diphenylguanidine. Thus [$^3$H]—DTG can be incorporated into a vulcanized rubber object, e.g., a tire tread, and rate of loss of rubber therefrom by water can be monitored by rate of loss of radioactivity.

The N,N'-disubstituted guanidines can readily be prepared by conventional chemical reactions, e.g., when R and R' are the same, by reaction of the corresponding amine with cyanogen bromide. Other methods which can be employed include the reaction of an amine or amine salt with a preformed alkyl or aryl cyanamide. See Safer, S. R., et al., *J. Org. Chem.* 13:924 (1948). This is the method of choice for producing N,N'-disubstituted guanidines in which the substituents are not identical. For a recent synthesis of unsymmetrical guanidines, see G. J. Durant et al., *J. Med. Chem.* 28:1414 (1985), and C. A. Maryanoff et al., *J. Org. Chem.* 51:1882 (1986).

Included as well in the present invention are the novel compounds disclosed herein as well as pharmaceutical compositions thereof comprising an effective mount of the N,N'-disubstituted guanidine in combination with a pharmaceutically acceptable carrier.

The N,N'-disubstituted guanidines and the pharmaceutical compositions of the present invention may be administered by any means that achieve their intended purpose. For example, administration may be by parenteral subcutaneous, intravenous, intramuscular, intra-peritoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

Compositions within the scope of this invention include all compositions wherein the N,N'-disubstituted guanidine is contained in an amount which is effective to achieve its intended purpose. While individual needs vary, determination of optimal ranges of effective mounts of each component is with the skill of the art. Typically, the compounds may be administered to mammals, e.g. humans, orally at a dose of 0.0025 to 15 mg/kg, or an equivalent amount of the pharmaceutically acceptable salt thereof, per day of the body weight of the mammal being treated for psychosis, depression, hypertension, or anxiety disorders, e.g., generalized anxiety disorder, phobic disorders, obsessional compulsive disorder, panic disorder, and post traumatic stress disorders. Preferably, about 0.01 to about 10 mg/kg is orally administered to treat or prevent such disorders. For intramuscular injection, the dose is generally about one-half of the oral dose. For example, for treatment or prevention of psychosis or anxiety, a suitable intramuscular dose would be about 0.0025 to about 15 mg/kg, and most preferably, from about 0.01 to about 10 mg/kg.

The unit oral dose may comprise from about 0.25 to about 400 mg, preferably about 0.25 to about 100 mg of the compound. The unit dose may be administered one or more times daily as one or more tablets each containing from about 0.10 to about 300, conveniently about 0.25 to 50 mg of the anxiolytic compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, steric acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

The characterization of sigma receptors in vitro has been difficult because of the lack of selective drug ligands. Most benzomorphan opiates cross-react with other (mu, delta, kappa), opioid receptors and are therefore of only limited value for characterizing and isolating receptors. Pasternak et al., *J. Pharmacol. Exp. Ther.* 219:192–198 (1981); Zukin, R. S., et al., *Mol. Pharm.* 20:246–254 (1981); and Tam, S. W., *Eur. J. Pharmacol.* 109:33–41 (1985). [$^3$H]DTG binds specifically and with high affinity to a single class of binding sites in guinea pig brain membranes. The binding characteristics and the drug specificity profile of these sites are concordant with those proposed for the sigma receptor, including 1) naloxone insensitivity and stereo-selectivity for dextrorotatory isomers of benzomorphan opiates such as (+)SKF 10,047, (+)cyclazocine and (+)pentazocine; 2) high affinity for haloperidol and certain phenothiazine antipsychotic drugs; 3) stereo-selectivity for (−)butaclamol; and 4) insensitivity to dopamine and apomorphine. [$^3$H]—DTG is one of only two known tritiated compounds that are selective for the sigma site. The other, (+)[$^3$H]3-PPP, originally proposed to be a dopamine autoreceptor agonist, has recently been shown to be selective for sigma sites in rat brain membrane binding assays. Largent et al. (1984), supra. Our experiments confirm these findings in the guinea pig and show that [$^3$H]DTG and (+)[$^3$H]3-PPP have virtually identical receptor binding characteristics and drug selectivity profiles. Previous studies have shown that sigma sites can also be labeled with (+)[$^3$H]SKF 10,047, (+)[$^3$H]-ethylketazocine and with (±)[$^3$H]SKF 10,047. However, these ligands are not selective for the sigma site and require the presence of appropriate drugs in the binding assays to mask cross-reacting non-sigma binding sites.

[$^3$H]DTG has a number of advantages as a sigma ligand. It is highly selective for the sigma site (unlike [$^3$H]SKF 10,047 and (+)[$^3$H]ethylketazocine), it has a high degree of specific binding (90–97% of total binding) and it has a relatively simple chemical structure that is not chiral (unlike (+)[$^3$H]3-PPP and the benzomorphan opiates). These characteristics make it a good starting compound for the synthesis of analogs for structure-activity studies and for the design of irreversible (after photolysis) sigma receptor ligands, e.g., compounds of Formulae I and II wherein at least one of R and R' is azido-substituted carbocyclic aryl.

The sigma site labeled with [$^3$H]DTG is clearly not related to conventional (mu, delta, kappa) opioid receptors as it is naloxone insensitive and shows stereoselectivity for dextrorotatory isomers of benzomorphan drugs. This is a reversed stereoselectivity compared to naloxone-sensitive opioid receptors which are selective for levorotatory isomers of opiates. Sigma receptors should therefore not be referred to as sigma "opioid" receptors. The drug selectivity of sigma sites for dextrorotatory isomers of psychotomimetic opiates does, however, correlate well with the pharmacological profile of dextrorotatory versus levorotatory opiates in animal tests designed to differentiate between conventional opioid receptor activity and sigma (behavioral) activity of benzomorphan drugs. Cowan, A., *Life Sci.* 28:1559–1570 (1981); Brady, K. T., et al., *Science* 215:178–180 (1982); and Khazan, N., et al., *Neuropharmacol.* 23:983–987 (1984).

Autoradiography studies using [$^3$H]DTG visualize the sigma site in slide-mounted rodent brain sections and confirm that sigma sites are different from mu, delta, and kappa opioid receptors as the distribution of [$^3$H]DTG binding is rather distinct from the distribution of mu, delta, kappa opioid receptors. The anatomical distribution of [$^3$H]DTG binding sites is, however, very similar if not identical to the distribution of [$^3$H]3-PPP binding sites, further confirming that the two radioligands label identical binding sites. The high affinity of the [$^3$H]DTG binding site for haloperidol and for certain phenothiazine antipsychotics (TABLE I) which are also dopamine $D_2$ receptor antagonists raises the question as to the relation of sigma receptors to dopamine $D_2$ receptors. The results presented show that the [$^3$H]DTG site is clearly distinct from dopamine $D_2$ receptors, because the autoradiographic distribution of dopamine receptor is dissimilar and because dopamine, apomorphine and many other dopamine receptor ligands do not interact with the [$^3$H]DTG binding site.

Furthermore the sigma site labeled with [$^3$H]DTG is stereoselective for (−)butaclamol which is a reversed stereoselectivity compared to the dopamine $D_2$ receptors which are stereoselective for (+)butaclamol.

The haloperidol-sensitive sigma site labeled with [$^3$H] DTG was found to have a moderate affinity for the potent hallucinogen PCP in competition experiments. This is in agreement with findings by others who use (+)[$^3$H]SKF 10,047, (±)[$^3$H]SKF 10,047 or (±)-[$^3$H]3-PPP to label sigma sites. In PCP receptor binding assays, however, [$^3$H]-PCP labeled predominantly (but not exclusively) a haloperidol-insensitive PCP binding site, termed PCP/sigma opiate receptor by Zukin and colleagues, Zukin et al. (1981, 1986), supra, which is separate from the haloperidol-sensitive sigma site labeled with [$^3$H]DTG or (+)[$^3$H]3-PPP. In contrast, [³H]DTG appears to label exclusively the haloperidol sensitive sigma site, since all specific binding is displaceable by haloperidol and the anatomical distribution of [³H]DTG binding is distinct from the distribution of PCP receptors. Furthermore, unlabeled DTG is virtually inactive in a [³H]-PCP binding assay (S. William Tam, E. 1. DuPont De Nemours & Co., Wilmington, Del., personal communication). There is some controversy as to which of the two binding sites is responsible for causing the behavioral effects of PCP and psychotomimetic benzomorphan opiates and would therefore correspond to the sigma receptor postulated by Martin et al. (1976), supra. Zukin and his collaborators have argued that the behavioral effects of both PCP and psychotomimetic benzomorphan opiates are mediated by the haloperidol-insensitive PCP site, to which benzomorphan opiates bind with moderate affinity. Largent et al. (1986), supra, cited circumstantial evidence suggesting that it is equally likely that the behavioral effects of both PCP and psychotomimetic opiates are mediated through the haloperidol sensitive sigma site. As [³H]DTG exclusively labels the haloperidol sensitive sigma site and does not interact significantly with the haloperidol-insensitive PCP site, behavioral studies using DTG or other substituted guanidines of this invention as prototypical sigma ligands, taking into account of whether they are agonists or antagonists (see below), should resolve this issue.

Perhaps the most important aspect of the findings on the drug specificity of sigma sites that have emerged from this and other studies is that they interact with certain very potent antipsychotic drugs (haloperidol, phenothiazines) that are used clinically to treat schizophrenia. This intriguing drug selectivity profile facilitates studies aimed at investigating the role of sigma receptors in antipsychotic drug action and abnormal brain function. The availability of DTG and like N,N'-disubstituted guanidines as a selective sigma ligand should serve to facilitate such studies.

The compounds of this invention have highly selective affinity for the sigma receptor. Consequently, they may have some of the activities of the benzomorphans, i.e., those produced by binding to the haloperidol-sensitive sigma receptor but not those produced by the binding of benzomorphans to other non-sigma receptors. For instance, benzomorphans may act at sigma receptors to cause mydriasis and tachycardia and pronounced psychotomimetic effects. DTG is therefore an effective tool to demonstrate the physiological effects mediated by the sigma receptor which, to date, have been obscured by cross-reactivity of benzomorphans with non-sigma receptors.

The compounds of this invention are particularly valuable in the treatment of humans afflicted with a psychotic disease, e.g., schizophrenia, or with chronic hypertension. In this regard, they can be employed in substantially the same manner as known antipsychotic agents and anti-hypertensive agents, respectively.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. The entire text of all applications, patents and publications, if any, cited above and below are hereby incorporated by reference.

EXAMPLES

In the foregoing and in the following examples, all temperatures are set forth uncorrected in degrees Celsius and unless otherwise indicated, all parts and percentages are by weight.

Preparations

General Procedures. Melting points are uncorrected. N M R spectra were recorded on a General Electric QE-300 spectrometer, operating at 300 MHz. Chemical shifts (δ) are given in ppm using the residual proton signal of the deuterated solvent as reference ($CHD_2OD$ δ3.300, $CHCl_3$ δ7.260, HDO δ4.80), or the $^{13}C$ signal of the solvent ($CD_3OD$ δ49.00, $CDCl_3$ δ77.00). All solvents were reagent grade quality. Where dry solvents were needed, these were distilled from $CaH_2$ or Na before use.

Adamantan-1-ylcyanamide was prepared from the amine with cyanogen bromide in $Et_2O$, as previously described by Geluk, N. W., et. al., *J. Med. Chem.* 12:712–716 (1969). (2-Methylphenyl)cyanamide was prepared similarly.

N,N'-Di-(adamantan-1-yl)guanidine hydrochloride was prepared according to the procedure of Geluk et al., supra.

Example 1

N,N'-Di-(4-bromo-2-methylphenyl)guanidine (4-Br—DTG)

To a stirred solution of cyanogen bromide (846 mg, 8.06 mmol) in distilled water (70 ml) was added in small portions 2.997 g (16.11 mmol) of 4-bromo-2-methylaniline (Aldrich, recrystallized from etherpentane). A white precipitate formed during the addition. The mixture was stirred at 80° C. for 4 h. Upon cooling at 0° C. for 12 h, a sticky yellow oil separated out and was discarded. The clear aqueous phase was concentrated to about 30 ml. The white precipitate which formed was redissolved by heating the mixture. This was then set aside at 4° C. for 12 h. Filtration gave 430 mg of white solid. A 200-mg portion was dissolved in 10 ml of hot water and treated with 5 ml of 10 KOH solution. The mixture was extracted with $CHCl_3$ and the extract was washed with brine and then dried ($MgSO_4$). Evaporation of the solvent gave 171 mg of a brown solid which was crystallized from $CHCl_3$, giving 120 mg (8%) 4-Br—DTG as small white needles: mp 209°–210°; NMR (300 MHz, $CD_3OD$, TMS) δ2.24 (s, 3), 7.12–7.25 (AB, 2, J=8 Hz), 7.35 (s, 1 ); IR (KBr) 3460, 3340, 1630 $cm^{-1}$. Analysis calculated for $C_{15}H_{15}N_3Br_2$: C, 45.37; H, 3.81; N, 10.58. Found: C, 45.34; H, 3.56; N, 10.50.

Example 2

[³H]-N,N'-di-ortho-tolyl-guanidine ([³H]DTG)

Twenty-five mg (0.1 mmol) of the thus-produced 4-Br—DTG were submitted to Amersham Corporation (Arlington Heights, Ill.) for catalytic reduction in the presence of 20 Ci of [³H]-gas. Two mCi portions of the crude, radioactive product in 0.2 ml/each of 25% ethanol were purified by reverse phase high performance liquid chromatography (RP-HPu) on a Vydac TP218 octadecasilica column using a $CH_3OH$ gradient (0–35% in 60 minutes) in 0.1% trifluoroacetic acid for elution. How rate was 1 ml/min. One minute fractions were collected. Aliquots of the fractions were diluted 100 fold and 10 ul aliquots of the diluted fractions corresponding to 0.1 ul of the original fractions were dissolved in 10 ml scintillation fluid and counted in a scintillation spectrometer. The equipment consisted of 2 Waters HPLC pumps, and automated electronic gradient controller and a Kratos variable wave length spectrophotometer. The radioactivity eluted as a major symmetrical peak coinciding with a major, symmetrical UV (220 nm) absorbing peak at 41 minutes. This is the same elution time at which authentic, unlabeled DTG emerges from the column in this RP HPLC system. The specific activity of [$^3$H]DTG was found to be 52 Ci/mmol based on the amount of DTG under the major UV absorbing peak as determined by quantitative UV-spectrophotometry and the amount of radioactivity associated with this peak as determined by quantitative liquid scintillation spectrometry.

Following this procedure, or one of another conventional labelling synthetic techniques well known in the art, the tritium labeled versions of other N,N'-disubstituted guanidines of this invention, e.g., those of Table I, can be produced. If only one of the N- and N'-groups employed as starting material bears a functional group convertible to an [$^3$H] bearing group, the resulting N,N'-disubstituted guanidine will be singly tagged. If both bear such a functional group, the resulting N,N'-disubstituted guanidine will be polytagged.

Example 3

N-(2-Methyl-4-isothiocyanatophenyl-N'-(2-methylphenyl)-guanidine
[Di-tolyl-Guanidine-Isothiocyanate (DIGIT)]

a. N-(2-Methyl-4-nitrophenyl)-N'-(2-methyl-phenyl)guanidine Hydrochloride and the corresponding free base A vigorously stirred mixture of 2-methylphenyl-cyanamide [1.107 g, 0.380 mmol, prepared from o-toluidine by the method of Safter et al. (1948)] and 2-methyl-4-nitroaniline hydrochloride in chlorobenzene (45 ml) was heated at 90° for 3 h and then allowed to cool to 25°. The resulting pale yellow precipitate was collected, washed with $CH_2Cl_2$, and dried, giving 2.284 g (91%) of the hydrochloride of the desired product (pure by NMR). A 681 mg sample was recrystallized twice from absolute EtOH to give 600 mg (88%) of the desired product as pale yellow microcrystals suitable for the next reaction: mp 196–200; ($CD_3OD$, 300 MHz) δ2.37 (s, 3), 2.47 (s, 3), 7.33–7.40 (m, 4), 7.59 (d, 1), 8.18 (dd, 1), 8.27 (d, 1). A 473 mg sample of the hydrochloride was dissolved in 50 ml of hot water, filtered, cooled to 25°, and treated with 5 ml of 5N NaOH. The resulting bright yellow precipitate of the title compound (free base) was dried (403 mg, 92%) and then recrystallized twice from 95% EtOH to give the analytical sample as yellow platelets: mp 177–179; ($DC_3OD$, 300 MHz) δ2.31 (s, 6), 7.01–7.35 (m, 5), 7.98 (dd, 1), 8.06 (d, 1). Analysis calculated for $C_{15}H_{16}N_4O_2$; C, 63.37; H, 5.67; N, 19.71. Found: C, 63.41; H, 5.42; N, 19.90.

b. N-(2-Methyl-4-aminophenyl)-N'-(2-methylphenyl)-guanidine hydrochloride

A Parr hydrogenation flask was charged with a solution of N-(2-methyl-4-nitrophenyl)-N'-2-(methylphenyl)-guanidine hydrochloride (478 mg) in 30 ml of absolute EtOH. 30% Pd on charcoal (71 mg) was added and then the mixture was hydrogenated at 60 psi at 25° C. for 12 h. All further operations were carried out under an atmosphere of Ar. The mixture was centrifuged, filtered through Celite and the filtrate was concentrated in vacuo to 2 ml. Ether (21 ml) was added and after 4 h at 20°, the white precipitate was collected and dried, giving 406 mg (78%) of the title compound (amine hydrochloride) suitable for the next reaction: mp 232.5°–234.5°, ($CD_3OD$, 300 MHz) δ2.22 (s, 3), 2.34 (s, 3), 6.60 (dd, 1), 6.66 (d, 1), 6.98 (d, 1), 7.26–7.38 (m, 4).

c. N-(2-Methyl-4-isothiocyanatophenyl)-N'-(2-methylphenyl)-guanidine Hydrochloride (DIGIT)

NaOAc (1.767 g, 21.5 mmol) and HOAc (0.839 g, 14.0 mmol) were dissolved in dry MeOH such that the final volume of the solution was 100 ml. A 12.7 ml aliquot of this solution was added to 199 mg (0.686 mmol) of N-(2-methyl-4-aminophenyl)-N'-(2-methylphenyl)guanidine hydrochloride under an Ar atmosphere. Thiophosgene (54.7 ul, 86.7 mg, 0.754 mmol, freshly distilled) was then injected into the stirred reaction mixture. The reaction was complete upon mixing as judged by silica gel TLC (500:100:1, $CHCl_3$—MeOH—HOAc). Water (20 ml) was added and the mixture was concentrated in vacuo to 19 ml.

The next steps were done in rapid succession in order to minimize the possible reaction of the isothiocyanate group with the guanidine free base grouping of another molecule. The above 19 ml concentrate was cooled to 0° and treated with ice-cold saturated $NaHCO_3$ (15 ml). The resulting mixture containing a white precipitate was extracted with $CHCl_3$ (4×15 ml). The combined extracts were washed with ice cold brine, dried ($MgSO_4$), filtered through Celite, and cooled to 0°. Next, excess HCl gas was bubbled through the colorless solution and then the solution was concentrated in vacuo to 25 ml and hexane (20 ml) was added. Four additional times the mixture was concentrated again and more hexane was added. Evaporation of the final mixture to dryness gave crude hydrochloride as a gummy white solid (263 mg, 115%). This was taken up in absolute ethanol (2 ml), and diluted with ether (80 ml) to give a cloudy white suspension from which small clusters of white needles formed on standing. The crystals were centrifuged, washed with ether (3×5 ml), and dried, giving 173 mg (76%) of the title compound: m.p. 195°–197° C. (preheated bath); ($CD_3OD$), 300 MHz) δ2.347 (s, 3), 2.351 (s, 3), 7.23 (d, 1), 7.31 (s, 1), 7.34 (d, 1), 7.26–7.40 (m, 4); IR (KBr) 3466, 3138, 2927, 2152, 2119, 1646, 1631 cm$^{-1}$. Analysis calculated for $C_{16}H_{17}ClN_4S$: C, 57.74; H, 5.15; N, 16.83. Found: C, 57.60; H, 5.20; N, 16.64.

A tri-tritiated version of DIGIT is prepared starting with tritiated N-(2-methyl-4-aminophenyl)-N'-(2-methylphenyl)-guanidine, which was prepared by catalytic tritiation (Amersham) of N-(2-methyl-4-nitro-6-bromophenyl)-N'-(2-methyl-4,6-dibromophenyl)-guanidine. The tri-tritiated amino compound was also used as the immediate precursor for the preparation of the tritritiated version of the 4-azido compound the preparation of which is described hereinafter and which was used in the solubilization of sigma receptors.

Example 4

N, Adamantan-1-yl-N'-cyclohexylguanidine HCl

Adamantan-1-ylcyanamide (514 mg, 2.92 mmol), and cyclohexylamine hydrochloride (398 mg, 2.93 mmol) were finely ground together, and heated at 200° C. for 10 min. The resultant glassy solid was pulverized, and extracted twice with 50 ml boiling 5% HCl. The insoluble material was filtered, and dried. 346 mg, mp 264°–270° (p.h.b. 240° C.). On cooling the combined aqueous extracts to 25°, a white ppt. formed, and was filtered off, 56 mg. Combined crude yield: 44%. Crystallization of a 50 mg sample of the crude product from EtOH/$Et_2O$ afforded white needles (25 mg, mp 269°–271° C. (p.h.b. 240°), lit. 268°–269° C.). $^1$H ($CD_3OD$) δ1.208–1.474 (m, 5H), 1.744 (s, 9H), 1.967 (s, 8H), 2.119

(5, 3H), 3.434 (m, 1H), $^{13}$C (CD$_3$OD) (broad band decoupled) 25.55, 26.26, 30.96, 33.74, 36.74, 42.73.

Example 5

N-Cyclohexyl-N'-(2-methylphenyl)guanidine

A suspension of cyclohexylamine hydrochloride (310 mg, 2.28 mmol) and (2-methylphenyl)cyanamide (365 mg, 2.76 mmol) in dry chlorobenzene was heated at 125°–135° for 4 hrs. The solvent was evaporated in vacuo with heating, and the residue partitioned between CH$_2$Cl$_2$ and 20×8 ml 10% HCl. The aqueous extracts were made alkaline to pH 9–9.5, and the white precipitate collected after standing at 4° C. overnight. Two recrystallizations from EtOH/H$_2$O gave 140 mg (22%) of white needles, mp 145°–146°, 1H (CD$_3$OD) δ1.149–2.054 (m, 10H), 2.164 (s, 3H), 3.50 (m, 1H), 6.875 (d, 1H, J=7.5 Hz), 6.968 (t, 1H, J=7.5 Hz), 7.118 (t, 1H, J=7.5 Hz), 7.177 (d, 1H, J=7.5 Hz). Anal. Calcd for C$_{14}$H$_{21}$N$_3$: C, 72.69; H, 9.15; N, 18.16. Found: C, 72.72; H, 9.24; N, 18.18.

Example 6

N-(Adamantan-1-yl)-N'-(2-methylphenyl)guanidine

A suspension of adamantan-1-ylcyanamide (151 mg, 0.857 mmol) and o-toluidine hydrochloride (186 mg, 0.857 mmol) in dry chlorobenzene was heated between 100°–130° C. for 4.5 hrs. The chlorobenzene was evaporated in vacuo with heating and the residue (285 mg) taken up in 18 ml of water. A gummy, insoluble material was discarded. On adjusting the aqueous extract to pH 9–9.5, a precipitate formed (194 mg, 71%). Two recrystallizations from EtOH/H$_2$O gave the analytical sample; mp 160°–161°, $^1$H (CD$_3$OD) δ1.742 (s, 6H), 2.050 (d, 6H, J=2.4 Hz), 2.029 (s, 3H), 6.956 (j, 1H, J=8.1 Hz), 7.056 (t, 1H, J=8.1 Hz), 7.168 (t, 1H, J=7.5 Hz), 7.213 (d, 1H, J=7.5 Hz). Anal. Calcd for C$_{18}$H$_{25}$N$_3$: C, 76.28; H, 8.89; N, 14.83. Found: C, 76.25; H, 8.86; N, 14.60.

Example 7

N-(Adamantan-1-yl)-N'-(2-iodophenyl)guanidine HCl

Adamantan-1-ylcyanamide (299 mg, 1.70 mmol) and o-iodoaniline hydrochloride (433 mg 1.70 mmol) were finely ground together and heated at 200° for 10 min. The resultant black glassy solid was pulverized, and recrystallized 5 times from EtOH/Et$_2$O. The resultant faintly blue needles (80 mg) were dissolved in 4 ml EtOH, and passed through a short (<1 cm) column packed from bottom to top with Celite, charcoal, activated alumina, and sand. The colorless eluate was then diluted with 5 ml Et$_2$O, and allowed to stand in an Et$_2$O diffusion chamber overnight. The white needles were collected by suction filtration, 40 mg, mp 274°–275° C. Addition of another 5 ml Et$_2$O yielded a second crop (31 mg) of identical material. Combined yield: 21%. $^1$H (CD$_3$OD) δ1.779 (s, 6H), 2.090 (s, 6H), 2.164 (s, 3H), 7.168 (t, 1H, J=8.1 Hz), 7.388 (d, 1H, J=9.1 Hz), 7.503 (t, 1H, J=7.8 Hz), 8.004 (d, 1H, J=7.8 Hz).

Example 8

N-(2-Methyl-4-azido-phenyl)-N'-(2-methylphenyl)guanidine

N-(2-Methylphenyl)-N'-(2-methyl-4-aminophenyl)guanidine dihydrochloride (112 mg, 0.341 mmol) were dissolved in 2 ml H$_2$O and 100 ul conc. HCl (1.2 mmol). The solution was cooled in an ice bath, and a solution of NaNO$_2$ (42 mg, 0.61 mmol) in 450 ul H$_2$O were added. The reaction mixture turned yellow, and was stirred for 45 min before solid NaN$_3$ (43 mg, 0.661 mmol) was added in a single portion. After N$_2$ evolution was caused, a foamy solid (11 mg) was removed and discarded. Solid NaOH (96 mg, 2.41 mmol) was added, and the bright yellow precipitate was extracted with Et$_2$O (3×5 ml). Evaporation of the combined Et$_2$O layers gave a yellow solid which was crystallized from EtOH/H$_2$O: NMR (CD$_3$OD) δ2.279 (s, 3H), 2.284 (s, 3H), 6.864 (dd, 1H, J=2.4 Hz, 8.4 Hz), 6.914 (d, 1H, J=2.1 Hz), 7.055 (td, 1H, J=1.8 Hz, 7.2 Hz), 7.136–7.229 (m, 4H).

Example 9

N-(2-Methyl-4-nitro-6-bromophenyl)-N'-(2-methyl-4,6-dibromophenyl)guanidine

N-(2-Methyl-4-nitrophenyl)-N'-(2-methylphenyl)guanidine, as the free base (281 mg, 0.987 mmol) was dissolved in 4 ml MeOH, and cooled in an ice-bath. N-bromosuccinimide (freshly recrystallized from H$_2$O) (531 mg, 2.98 mmol) was added in two portions over 15 min. After 1.5 hrs the brown sludgy reaction mixture was diluted with 4 ml MeOH, and allowed to warm to 25° C. A brown solid was filtered off (266 mg), and crystallized from acetone/H$_2$O, to afford brown needles (2.6 mg, 42%, mp 193°–195° C.). Sublimation of a 56 mg sample of these crystals at 0.01 mm Hg and 170° afforded the analytical sample as a bright yellow amorphous solid (38 mg, mp 210°–213° C.). NMR (CD$_3$OD) δ2.357 (s, 3H), 2.488 (s, 3H), 7.444 (d, 1H, J=1.5 Hz), 7.669 (d, 1H, J=1.8 Hz), 8.033 (d, 1H, 2.1 Hz), 8.267 (d, 1H, 2.4 Hz). Anal. Calcd for C$_{15}$N$_{13}$Br$_3$N$_4$O$_2$: C, 34.58; N, 2.52; N, 10.75. Found: C, 34.64; N, 2.41; N, 10.65.

Example 10

N,N'-Bis(2-iodophenyl)guanidine

A solution of cyanogen bromide (4.4042 g, 38.2 mmol) and 2-iodoaniline (4.138 g, 18.9 mmol) in H$_2$O (70 ml) was heated at 70°–80° C. for 5 h. The reaction mixture was decanted from an off-white solid (1.90 g) which was discarded, and the supernatant was heated at the same temperature an additional 16 h. On cooling to 25° C., the title compound precipitated from solution as its hydrobromide salt and was centrifuged off, and dried (500 mg, 10%). This white powder was dissolved in boiling H$_2$O (20 ml), and 5N NaOH (2 ml) was added to the clear solution. The resulting white precipitate (290 mg) was washed with H$_2$O (3×4 ml), and crystallized from 95% EtOH, to give the title compound (119 mg, 39% from the hydrobromide salt) as long white needles: mp 161°–162° C. One further crystallization provided the analytical sample: mp 161°–162° C. Anal. Calcd for C$_{13}$N$_{11}$N$_3$I$_2$: C, 33.72; N, 2.39; N, 9.07. Found: C, 33.80; N, 2.26; N, 8.78. $^1$N NMR: δ6.790 (t, J=7.8 Hz, 2H), 7.304 (t, 3=7.8 Hz, 2H), 7.506 (d, 3=7.8 Hz, 2H), 7.817 (d, 3=7.8 Hz, 2H). IR: 729, 753, 1467, 1502, 1572, 1613, 1647, 3056, 3387 cm$^{-1}$.

Example 11

N,N'-Bis(3-methylphenyl)guanidine

Cyanogen bromide (788 mg, 7.44 mmol) was placed in a 25 ml round bottom flask, and m-toluidine (1.89 g, 17.6 mmol) was added dropwise. After the exothermic reaction had subsided, the residue was taken up in $CH_2Cl_2$ (20 ml), and was extracted with 5% HCl (5×10 ml). The aqueous extracts were adjusted to pH 10 with 6N NaOH. The resulting precipitate (674 mg, 38%) was filtered off and crystallized from $EtOH/H_2O$ to give the title compound (240 mg, 14%) as white needles: mp 105°–106° C. $^1$H NMR: δ2.289 (s, 6H), 6.814 (d, 2H, J=7.5 Hz), 6.939 (d, 2H, J=7.5 Hz), 6.981 (s, 2H), 7.141 (t, 2H, J=7.5 Hz). Anal. Calcd for $C_{15}H_{17}N_3$: C, 75.28; H, 7.16; N, 17.56. Found: C, 75.42; H, 7.11; N, 17.43.

References

[1]Geluk, H. W., et al., *J. Med. Chem.* 12:712 (1969).

[2]Kazarinova, N. F., et al., *Zn. Anal. Khim.* 28:1853 (1973); *Chem. Abstr.* 80:97021 (1973).

Example 12

Synthesis of N,N'-Di(o-tolyl)-2-imino-imidazolidine a. Synthesis of N,N' Ditolyl oxalodiamide Oxalyl chloride (32 mmol) in methylene chloride (16 mL) was added dropwise to a solution of o-toluidine (67 mmol) in methylene chloride (4 mL) over a period of 10 min at 4° C. After the exotherm subsided, the solution was removed from the ice bath and stirred at ambient temperature for 2 h. A white precipitate had formed. The precipitate was filtered off, dried, and found to weigh 724.6 mg (90%). The amide and the hydrooxalate salts were partially dissolved in methylene chloride (20 mL) and extracted with 1N HCl (5×, 15 mL). The resultant white suspension was filtered to provide a white solid (61%, mp 103°–104° C.). $^1$H NMR ($CD_3CN$/DMSO): δ2.259 (6H, s), 7.128–7605 (8H, m). IR (KBr): 1298.7, 1642.9 (amide).

b. Synthesis of N,N' Bistolyl ethylene diamine

The following procedure was adapted from H. C. Brown, *J. Org. Chem.* 38:912 (1978). Diborane (5 mmol) in THF was added dropwise to a THF solution of N,N' Ditolyl oxalodiamide (443.0 mg, 1.65 mmol) over 10 min at 0° C. After 30 min, the reaction mixture was allowed to stir at ambient temperature for 6 h. Then the solution was refluxed for 3 h. The resulting yellowish solution was allowed to cool to 25° C. The solution was then acidified dropwise with 15% HCl (15 mL) via an additional funnel over 20 min. Gas evolution was noted and a white precipitate had formed. The THF was then distilled off from the water through rotoevaporation at 25° C. The water was then made basic with an excess of NaOH and then extracted with ether. The ether layer was washed with brine, then dried over anhydrous potassium carbonate. The ether layer was then concentrated to dryness to provide a tannish brown liquid. The liquid was immediately taken up again in dry ether. Following this procedure, the solution was made acidic by adding ethereal HCl (10 mL) dropwise. A white solid had formed. This solid was immediately filtered off and dissolved in ethanol (5 mL) and placed into an ether diffusion chamber. After 2 days, white prisms were found (158.1 mg, 30.6%), mp 268°–270° C.

IR (KBr): in comparison with IR of diamide the bands at 1643.8 and 1298.7 cm$^{-1}$ had disappeared.

c. Synthesis of N,N' Bistolyl-2-imino-imidazolidine

N,N' Bistolyl ethylene diamine (105.8 mg, 0.44 mmol) was taken up in EtOH (3 mL) to provide a light purple solution. This solution was then placed in a one-necked round-bottom flask (25 mL) equipped with magnetic stirbar and reflux condenser. To this solution, cyanogen bromide (50 mg, 0.47 mmol) in ethanol (2 mL) was added in a single portion. The resultant reaction mixture was stirred for 1 h. It was noted that the solution turned clear. The solution was then brought to reflux and maintained at that temperature for 16 h. The reflux condenser was then removed, allowing the solvent to evaporate. The reaction mixture was then fused at 150° C. for 30 min to provide a brown solid. This solid was immediately taken up in ethanol (4 mL) and placed into a centrifuge tube. To this solution 1N NaOH was added (8 mL) to provide a "whispy" tan precipitate. After several failed attempts to pellet the precipitate, the solution was simply extracted with chloroform (20 mL). The chloroform was concentrated to dryness to provide a clear oil (108.1 mg, 92.6%).

Example 13

Synthesis of N-Cyclohexyl-N'-(2-methyl-4-bromophenyl)guanidine

A solution of bromine (0.336 g, 2.1 mmol) in glacial acetic acid (1 ml) was added dropwise to a stirred solution of N-cyclohexyl-N'-(2-methylphenyl)guanidine (0.231 g, 1 mmol) in glacial acetic acid (2 ml) at room temperature. After the addition, the addition funnel was replaced by a reflux condenser and the red reaction solution was heated on a warm water bath at 70° C. for about an hour. The reaction mixture was allowed to cool to room temperature and then poured in cold ice water (30 ml) containing a 200 mg of sodium bisulfite. The mixture was then extracted with dichloromethane (3×15 ml) and the combined organic layers were dried over sodium sulfate, filtered and concentrated to give a colorless liquid (0.475 g). This liquid was purified on a flash silica gel column to give a bright foamy product (0.25 g), mp 89°–91° C.

$^1$H NMR (CDCl$_3$): δ7.4 (s, 1H, Ar-3-H); 7.32 (dd, 1H, J=8.29 and 1.52 Hz, Ar-5-H); 6.99 (d, 1H, J=8.34 Hz, Ar-6-H); 2.22 (s, 3H—Ar—CH3) and 1.95–1.11 (m, 11H, cyclohexyl).

Mass (CI): 310, 312 (M$^+$), 232 (M$^+$—Br).

Example 14

Synthesis of N-(Adamantan-1-yl)-N'-(2-trifluoromethyl-4-fluorophenyl)guanidine 1-Adamantylcyanamide—A 2 liter glass three neck round bottom flask equipped with a mechanical stirrer, thermometer and 250 ml pressure equalizing addition funnel was charged with 1-adamantanamine (72.25 g, 0.48 mol), anhydrous ethyl ether (1L) and the solution cooled in an ice bath (0°–5° C.). The addition funnel was charged with a solution of cyanogen bromide (327.0 g, 0.31 mol) in anhydrous ethyl ether (200 ml). The reaction apparatus was purged with N$_2$ and a N$_2$ atmosphere maintained throughout the reaction. The cyanogen bromide was added dropwise with stirring so as to maintain the temperature of the reaction mixture below 5° C. The addition required 35 minutes and upon completion the ice bath was removed and the reaction mixture allowed to reach room temperature. The reaction mixture was allowed to stir overnight. The reaction mixture was filtered (sintered glass funnel) to remove the adamantylamine hydrobromide and the filtrate concentrated in vacuo (Buchi Rotovap RE 111) at 10 torr (aspirator vacuum) to afford the crude product. The crude product was dissolved in hot ethanol (100 ml) and distilled water (200 ml, room temperature) was added or until the point where turbidity was observed. The flask and contents were placed in the refrigerator over night. The product crystals were collected by filtration and air dried briefly (15 min). The product was then dried in a large capacity Abderhalden drying pistol at room temperature at 0.1 mm for 48 h to afford 46.01 g of 1-adamantylcyanamide.

N-(Adamantan-1-yl)-N-(2-trifluoromethyl-4-fluorophenyl)guanidine Hydrochloride. A single neck 50 ml round bottom flask was charged with chlorobenzene (14 ml), 2-trifluoromethyl-4-fluoroaniline hydrochloride (L. M. Weinstock et al., Tet. Lett. 1419 (1978)) (1.0 g, 4.64 mmol) and 1-adamantylcyanamide (0.82 g, 4.64 mmol). The reaction apparatus was purged with $N_2$, and the reaction heated at reflux under $N_2$, whereupon a clear colorless solution resulted. Within minutes, a thick white precipitate had formed. After 4.5 hr, the heating mantle was removed and after cooling to room temperature diethyl ether (30 ml) was added and the white solid (1.3 g) was collected by filtration. A portion of this white solid (0.6 g) was crystallized from iso-propanol and the resulting white crystals were filtered and dried in vacuo at 100° C. to give the title product (0.35 g), mp 260°–61° C.

Anal. Calcd for $C_{18}H_{22}N_3ClF_4$ (391.83): C, 55.17; H, 5.66; N, 10.72. Found: C, 55.32; H, 5.58; N, 10.88.

Example 15

Synthesis of N-(Adamantan-1-yl)-N'-(2-trifluoromethylphenyl)guanidine)

A single neck glass 100 ml round bottom flask was charged with chlorobenzene (25 ml), o-(trifluoromethyl)-aniline hydrochloride (prepared from the free base, Aldrich, by dissolving in 5% HCl in MeOH and concentrating, 5.93 g, 30.0 mmol) and 1-adamantylcyanamide (5.29 g, 30.0 mmol).

The reaction apparatus was purged with $N_2$ and the reaction heated at reflux under $N_2$, whereupon a clear colorless solution resulted. Within minutes a thick white precipitate had formed and an additional 15 ml of chlorobenzene was added to facilitate more efficient stirring. After 3 h, the heating mantle was removed and after cooling to room temperature the white solid was collected by filtration. This material was dissolved in boiling EtOH, filtered to remove insolubles, and ether added to the filtrate until turbid. The white solid which crystallized on standing was collected by filtration and dried in vacuo at room temperature to give the title product mp 259°–260° C.

Anal. Calcd for $C_{18}H_{23}N_3ClF_3$ (373.83): C, 57.82; H, 6.20; N, 11.24. Found: C, 57.67; H, 6.20; N, 11.46.

Example 16

Synthesis of N-(Adamantan-1-yl)-N'-(2,4-difluorophenyl)guanidine

A single neck glass 100 ml round bottom flask was charged with chlorobenzene (20 ml), 2,4-difluoroaniline hydrochloride (prepared from the free base, Aldrich, by dissolving in 5% HCl in MeOH and concentrating, 2.0 g, 12 mmol) and 1-adamantylcyanamide (2.13 g, 12 mmol).

The reaction apparatus was purged with $N_2$, and the reaction heated at reflux under $N_2$, whereupon a clear colorless solution resulted. Within minutes a thick white precipitate had formed. After 2 h, the heating mantle was removed and after cooling to room temperature the white solid was collected by filtration. This material was recrystallized two times from ethanol and the resultant white solid dried in vacuo at room temperature to give the title compound mp 258°–260° C.

Anal. Calcd for $C_{17}H_{22}N_3ClF_2$ (341.82): C, 59.73; H, 6.49; N, 12.29. Found: C, 59.62; H, 6.44; N, 12.23.

Example 17

Synthesis of N,N'-Bis (3-ethylphenyl)-2-imino-imidazolidine

N,N'-di-(3-ethylphenyl)oxalodiamide Oxalyl chloride (19 mmol) in methylene chloride (16 ml) was added dropwise to a solution of 3-ethylaniline (40 mmol) in methylene chloride (4 ml) over a period of 10 minutes at 4° C. After the exotherm subsided, the solution was removed from the ice bath and stirred at 25° C. for 2 hours. The reaction mixture was diluted with another 40 ml of $CH_2Cl_2$. The methylene chloride solution was washed by aqueous HCl (1N, 40 ml×2), aqueous NaOH (3%, 30 ml×1), and brine (20 ml), dried, and concentrated. The crude product was washed with $CH_2Cl_2$ (10 ml) as well as aqueous HCl (1N, 5–8 ml), the the precipitate was collected by filtration and dried under vacuum to provide a white solid N,N'-di(3-ethylphenyl)-oxalodiamide in 55% yield. Mp 131° C.; $^1$H NMR (60 MHz, $CDCl_3$): δ1.2 (t, 6H), 2.6 (q, 4H), 6.8–7.6 (m, 8H). IR ($CH_2Cl_2$)=1690, 1520 $cm^{-1}$.

N,N'-Bis-(3-ethylphenyl)ethylene diamine Diborane (27.4 mmol, 27.4 ml, 1M) in THF was added dropwise to a THF solution of N,N'-di-(3-ethylphenyl)oxalodiamide (6.76 mmol, 2 g) over 10 minutes at 0° C. After 30 minutes, the reaction mixture was refluxed for 16 hours. The resulting yellowish solution was allowed to cool to 25° C. The solution was then acidified by adding aqueous HCl (15%, 15 ml) over 20 minutes; gas evolution was noted and a white precipitate had formed. The THF was then distilled off from the water through rotoevaporation at 25° C. The water was then made basic with excess of NaOH and then extracted with $CH_2Cl_2$. The $CH_2Cl_2$ layer was washed with brine, then dried over anhydrous potassium carbonate. The $CH_2Cl_2$ layer was then concentrated to dryness to provide an oil in 66% yield. $^1$H NMR (60 MHz,, $CDCl_3$): δ1.2 (t, 6H), 2.5 (q, 4H), 3.2 (s, 4H), 6.3–7.2 (m, 8H). IR ($CH_2Cl_2$)=1420, 1600 $cm^{-1}$.

N,N'-Bis (3-ethylphenyl)-2-imino-imidazolidine N,N'-Bis(3-ethylphenyl)-ethylene diamine (0.4 g, 1.49 mmol) in EtOH (2 ml) was placed in a one necked round bottom flask equipped with a magnetic stir bar and reflux condenser. To this solution, cyanogen bromide (174 mg, 1.64 mmol) was added in a single portion. The solution was then brought to reflux for 15 hours. After reaction, the mixture was concentrated and recrystallized in MeOH/ether to yield a white crystal in 54% yield. MP 155° C.; $^1$H NMR (300 MHz, $CDCl_3$): δ1.25 (t, J=7.6 Hz, 6H), 2.72 (q, J=7.6 Hz, 4H), 4.36 (s, 4H), 7.21–7.39 (m, 8H). $^{13}$C NMR (300 MHz, $CDCl_3$): 15.08, 28.47, 49.45, 122.40, 124.48, 128.62, 130.31, 134.91, 147.00, 154.39. IR ($CH_2Cl_2$)=1470, 1550 cm$^{-1}$. Elemental analysis. Calcd: C, 58.76; H, 6.49; N, 10.82. Found: C, 59.14; H, 6.83; N, 10.85.

Example 18

Characteristics of [$^3$H]DTG binding to guinea pig brain membranes

Synthesis [$^3$H]DTG resulted in a pure homogenous product of high specific radioactivity (52 Ci/mmol). [$^3$H]DTG bound specifically, saturably, reversibly, and with high affinity to guinea pig brain membrane. In a typical experiment with 0.9 nM [$^3$H]DTG (30,000 cpm, 50% counting efficiency) the total binding was 2700 cpm while the nonspecific binding in the presence of 10 uM DTG or 10 uM haloperidol was 50–150 cpm. Routinely, a specific binding to 90–97% of total binding was observed. At room temperature the binding of [$^3$H]DTG reached equilibrium after 60–90 minutes and it was fully reversible after addition of 10 uM unlabeled DTG. Specific binding was linear with tissue concentration between 2–40 mg tissue (original wet brain weight per assay tube). Binding of radioactivity to the glass fiber filters in the absence of membranes was 10–20 cpm. Boiling of membranes at 100° C. for 10 minutes prior to assay almost completely (90%) abolished specific [$^3$H]DTG binding as did treatment of the membranes with trypsin and pronase (0.01 mg/ml for 30 min at room temperature), indicating that protein components are important for the receptors binding ability.

To determine the equilibrium saturation binding of [$^3$H]DTG to guinea pig brain membranes, membranes prepared as described herein were incubated with [$^3$H]DTG at various concentrations from 0.3 nM to 90 nM in 1 ml 50 nM Tris/HCl buffer, pH 7.4, for 120 minutes at room temperature. Values obtained were the mean of quadruplicate determinations.

A Scatchard analysis of the saturation data shows a linear Scatchard plot with an apparent $K_D$ of 28 nM and a maximum number of binding sites (Bmax) of 85 pmol/g brain tissue (original wet weight). Analysis of the binding data with the curve fitting program LIGAND, Munson, P. J., et al., Anal. Biochem. 107:220–239 showed high compatibility with a one site binding model.

Example 19

Radioligand Binding Assays

Frozen guinea pig brains (Pel-Freeze, Rogers, Ariz.) were homogenized in 10 volumes (w/v) of 0.32M sucrose using a Polytron homogenizer. The homogenate was spun at 900×g for 10 minutes at 4° C. The supernatant was collected, and spun at 22,000×g for 20 minutes at 4° C. The pellet was resuspended in 10 volumes of 50 mM Tris/HCl buffer, pH 7.4, incubated at 37° C. for 30 minutes and spun again at 22,000×g for 20 minutes at 4° C. The pellet was then resuspended in 10 volumes of 50 mM Tris/HCl buffer, pH 7.4 and 10 ml aliquots of this membrane suspension were stored frozen at −70° C. until used in the binding assay. No effects of prolonged storage (>3 months) of the membranes at −70° C. on sigma receptor number or affinity for [$^3$H]DTG binding were observed.

For radioreceptor assays aliquots of the frozen membrane suspension were thawed and diluted tenfold with 50 nM Tris/HCl buffer, pH 7.4. To 12×75 mm polystyrene or glass test tubes were added 0.8 ml of membrane suspension, 0.1 ml [$^3$H]DTG or (+)[$^3$H]3-PPP for a final concentration of 0.9 nM, and 0.1 ml of unlabeled drugs or buffer. The protein concentration in the 1 ml final incubation volume was 800 ug, corresponding to 32 mg of brain tissue (original wet weight). Nonspecific binding was defined as that remaining in the presence of either 10 uM DTG or haloperidol for both the [$^3$H]DTG and the (+)[$^3$H]3-PPP binding. After incubation for 90 minutes at room temperature the membrane suspension was rapidly filtered under vacuum through Whatman GF/B glass fiber filters using a Brandel 48 well cell harvester (Brandel, Gaithersburg, Md.). The filters were washed with 3×5 ml ice-cold 50 nM Tris buffer (pH 7.4 at room temperature). The filters were dissolved in 10 ml each of Cytoscint (Westchem Products, San Diego, Calif.) and radioactivity was measured by liquid scintillation spectrometry at a counting efficiency of 35–50%. Saturation data were evaluated by Scatchard analysis using both the EBDA NcPherson, G. A., Computer Programs Biomed. 17:107–114 (1983), and LIGAND Munson, P. J., et al., Anal. Biochem. 107:220–239 (1980), data analysis programs on an IBM Personal Computer-AT. IC$_{50}$ values were determined by plotting displacement curves onto semilogarithmic graph paper followed by interpolation or by computerized non-linear least squares curve fitting (Fischer, J. B. et al., J. Biol. Chem. 263:2808–2816 (1988).

Utilizing the radioligand binding assay described above, the sigma receptor binding activity based on [$^3$H]DTG displacement activity (IC$_{50}$ value) for the sixteen (16) N,N′-disubstituted guanidine compounds listed in Table I below was determined. The IC$_{50}$ value for each compound is reported in Table I.

TABLE I

| Compound | IC$_{50}$ vs [$^3$H]DTG (nM) |
| --- | --- |
| N,N′-di-o-tolyl-guanidine | 32 ± 1 |
| N,N′-di-n-butyl-guanidine | 750 ± 33 |
| N,N′-diphenyl-guanidine | 397 ± 21 |
| N,N′-diadamantyl-guanidine | 17 ± 3 |
| N-adamantyl-N′-2-methylphenyl-guanidine | 3 ± 1 |
| N,N′-di(2-methyl-4-bromophenyl)guanidine | 37 ± 3 |
| N-(2-iodophenyl)-N′-(2-methylphenyl)-guanidine | 21 ± 1 |
| N-(2-methyl-4-nitrophenyl)-N′-(2-methylphenyl)-guanidine | 37 ± 5 |
| N,N′-di-(2,6-dimethylphenyl)guanidine | 90 ± 18 |
| N-(2,6-dimethylphenyl)-N′-(2-methylphenyl)-guanidine | 70 ± 3 |
| N-(adamantyl)-N′-(cyclohexyl)guanidine | 13 ± 2 |
| N,N′-di(cyclohexyl)guanidine | 71 ± 7 |
| N-(2-iodophenyl)-N′-(adamantyl)guanidine | 5 ± 1 |
| N-(2-methylphenyl)-N′-(cyclohexyl)guanidine | 17 ± 5 |
| N-(2-methyl-4-azidophenyl)-N′-(2-methylphenyl)-guanidine | 20 ± 1 |
| N-(2-methylphenyl)-N′-(4-amino-2-methylphenyl)-guanidine | 280 ± 14 |

Fourteen of these compounds were found to be potent ligands of sigma receptors as determined by their ability to displace [$^3$H]DTG from sigma receptors in guinea-pig brain homogenates, the most potent being N-(2-methylphenyl)-N′-(adamantan-1-yl)guanidine with an IC$_{50}$ of 2.6±0.6 nM (n=6).

In a second series of experiments, selected compounds were tested against [$^3$H]MK-801 and [$^3$H]DTG. The results depicted in Table II are as follows (nM):

TABLE II

| Chemical name | IC$_{50}$ vs* [$^3$H]DTG | [$^3$H]MK-801 |
|---|---|---|
| N-(1-Naphthyl)-N'-(2-iodophenyl)-guanidine | 40.1 ± 7.3 (4) | 209 ± 50 (4) |
| N-(Cyclohexyl)-N'-(4-bromo-2-methylphenyl)-guanidine | 4.67 ± 1.04 (4) | 23860 ± 8540 (5) |
| N,N'-Di-(4-indanyl)-guanidine | 28.5 ± 7.5 (3) | 506 ± 99 (2) |
| N-(Adamantan-1-yl)-N'-(2-trifluoromethyl-phenyl)-guanidine | 7.44 ± 0.50 (3) | 23100 ± 13100 (2) |
| N-(Adamantan-1-yl)-N'-(2-methylphenyl)-N'-methyl-guanidine | 22.6 ± 1.9 (4) | not done |
| N-(Adamantan-1-yl)-N'-(6-coumarinyl)-guanidine | 21.9 ± 0.7 (4) | >10,000 (2) |
| N-(Adamantan-1-yl)-N'-(8-coumarinyl)-guanidine | 43.9 ± 2.0 (4) | 6,700 (1) |
| N-(Adamantan-1-yl)-N'-(2,4-difluorophenyl)-guanidine | 8.92 ± 0.48 (4) | >10,000 (1) |
| N-(Adamantan-1-yl)-N'-(2-trifluoromethyl-4-fluoro-phenyl)-guanidine | 4.27 ± 0.45 (4) | 31,900 (1) |

*[s.e.m. (n)]

Example 20

Drug Specificity of [$^3$H]DTG Binding

Displacement experiments were performed with drugs that are considered typical sigma ligands, as well as with drugs considered to be prototypical ligands for other neurotransmitter, neuromodulator, and drug receptors. The IC$_{50}$ vs [$^3$H]DTG and vs. [$^3$H]3-PPP results are given in Table III below. These experiments showed that the [$^3$H]DTG binding site is stereoselective for dextrorotatory benzomorphan opiates and for (−)butaclamol; does not significantly interact with drugs that have high affinities for acetylcholine, benzodiazepine, GABA, nor with mu, delta, or kappa opioid receptors; has a high affinity for haloperidol and several drugs belonging to the phenothiazine class of antipsychotics (haloperidol had the highest displacement potency of all drugs tested); and has a moderate affinity for several other classes of psychoactive drugs, which included several tricyclic antidepressants, PCP, and the kappa opioid receptor ligand U50, 488H.

TABLE III

| Drug | IC$_{50}$ vs. [$^3$H]DTG (nM) (± SEM) | IC$_{50}$ vs. (+)[$^3$H]3-PPP (nM) (± SEM) |
|---|---|---|
| Haloperidol | 5 ± 0.3 | 17 ± 1 |
| DTG | 28 ± 1 | 53 ± 9 |
| Perphenazine | 42 ± 10 | 21 ± 3 |
| (+)Pentazocine | 43 ± 2 | 8 ± 3 |
| (−)Pentazocine | 135 ± 3 | 81 ± 1 |
| (±)Pentazocine | 69 ± 1 | ND |
| (+)3-PPP | 76 ± 4 | 33 ± 12 |
| (−)3-PPP | 280 ± 21 | 235 ± 60 |
| (+)Cyclazocine | 365 ± 25 | 47 ± 12 |
| (−)Cyclazocine | 2,600 ± 210 | 1,000 ± 0 |
| Spiperone | 690 ± 21 | ND |
| (−)Butaclamol | 530 ± 49 | 183 ± 5 |
| (+)Butaclamol | 2,150 ± 250 | 2,100 ± 71 |
| (+)SKF 10,047 | 625 ± 88 | 93 ± 5 |
| (−)SKF 10,047 | 4,000 ± 566 | 2,850 ± 390 |
| PCP | 1,050 ± 106 | 1,000 ± 71 |
| U50,488H | 1,350 ± 106 | ND |
| Trifluoperazine | 345 ± 4 | ND |
| Trifluopromazine | 605 ± 67 | ND |
| Chlorpromazine | 1,475 ± 265 | ND |
| Amitriptyline | 300 ± 7 | ND |
| Imipramine | 520 ± 14 | ND |
| Desipramine | 4,000 ± 566 | ND |
| Nortriptyline | 2,000 ± 640 | ND |
| Guanabenz | 4,600 ± 283 | ND |
| Clonidine | >10,000 | ND |
| Cocaine | >10,000 | ND |

*IC$_{50}$ is the molar concentration of the drug needed to produce half-maximal displacement of [$^3$H]DTG from sigma receptors. This is a direct measure of the sigma receptor binding potency of the drug. ND = not determined.

The above IC$_{50}$s represent the average from 2–4 separate experiments (in triplicate). The following compounds caused no significant displacement at a 10 uM concentration: scopolamine, 5-OH-tryptamine, diazepam, bicuculline, picrotoxin, hexamethonium, dopamine, apomorphine, GABA, gamma-guanidino butyric acid, morphine, DAGO, metorphamide, dynorphin A, [leu$^5$] enkephalin, beta-endorphin, naloxone, guanidino acetic acid, creatine, creatinine, 1,1-dimethyl-4-guanidine, methyl-guanidine, beta-guanidino propionic acid and cimetidine.

Example 21

Drug specificity of [$^3$H]DTG binding compared to (+)-[$^3$H]3-PPP binding

Comparing the drug specificity of [$^3$H]—DTG binding with that of (+)[$^3$H]3-PPP in the guinea pig, it was found that (+)[$^3$H]3-PPP bound specifically, saturably (linear Scatchard plot), reversely and with high affinity to guinea pig brain membranes (K$_D$=30 nm, Bmax=80 pmol/g fresh brain weight). The drug specificity profile of the (+)[$^3$H]3-PPP binding in the guinea pig (Table II) was found to be very similar to that reported in the rat. Largent et al. (1984), supra. Moreover, the drug specificity profiles of typical sigma receptor active drugs in the (+)[$^3$H]3-PPP and [$^3$H]—DTG binding assays were highly correlated (r=0.95; p≦0.00001) which is consistent with the two compounds labeling the same sites.

Example 22

Autoradiography Studies

Male Sprague Dawley rats (200–250 g) and NIH guinea pigs (300–350 g) were sacrificed, their brains rapidly removed and processed for receptor autoradiography according to the method of Herkenham et al. J. Neuroscience 2:1129–1149 (1982).

Fifteen um thick slide-mounted brain sections were incubated for 45 minutes in 50 nM Tris-HCl (pH 8.0, 22° C.) containing 1 mg/ml bovine serum albumin (BSA) and 2 nM [$^3$H]DTG. Adjacent sections were incubated with 10 uM haloperidol or 10 uM DTG to measure nonspecific binding. Incubations were terminated by 4×2 minute washes in 10 nM Tris-HCl (pH 7.4, 4° C.) with 1 mg/ml BSA, rapidly dried under a stream of cool air and placed in x-ray cassettes with $^3$H-sensitive film ($^3$H-ultrofilm, LKB). Films were developed 6–8 weeks later (D-19, Kodak).

Example 23

Autoradiographic visualization of [³H]DTG binding

Receptor autoradiography studies on guinea pig and rat brain sections using [³H]DTG showed a low density of specific binding diffusely distributed throughout the gray matter of the rat and guinea pig brain. Superimposed on this homogeneous binding patterns was a heterogeneous distribution of enriched binding in limbic and sensorimotor structures. The pattern of binding was more distinct in the guinea pig than rat. Similar observations for (+)[³H]3-PPP autoradiography have been reported. Largent et al. (1986), supra. Thus, description of [³H]DTG binding was drawn primarily from the guinea pig. In the forebrain, limbic structures moderately to densely labeled by [³H]DTG were the diagonal band of Broca, septum, hypothalamus (especially the paraventricular nucleus), anterodorsal thalamic nucleus and zona incerta. Sensorimotor thalamic nuclei moderately to densely labeled included the thalamic taste relay and reticular nuclei. Other thalamic nuclei labeled were the paraventricular and habenular nuclei. Very dense binding was seen in the choroid plexus. In the cortex dense [³H]DTG labeling occupied layer III/IV of retrospenial piriform, and entorhinal cortices. The rest of the cortex contained a low level of homogeneous binding. The hippocampal formation exhibited discrete binding in the pyramidal granular cell layers. Sensorimotor areas of the midbrain were selectively labeled by [³H]DTG. The oculomotor nucleus, and more caudally, the trochlear nucleus were very densely labeled, and the superior colliculus and red nucleus had moderate levels of binding. Other midbrain nuclei labeled were the dorsal raphe, interpeduncular nucleus, central gray, and the substantia nigra, para compacta. The selective labeling of the para compacta in the guinea pig contrasted with the low to moderate density of labeling present throughout the substantia nigra of the rat. In addition, very dense binding was found in the subcommissural organ. In the hindbrain the locus coeruleus was the most densely labeled nucleus. Sensorimotor nuclei enriched in [³H]DTG binding sites were the trigeminal motor nucleus, nucleus of the facial nerve, nucleus of the solitary tract, dorsal motor nucleus of the vagus, and the hypoglossal nucleus. Moderate to dense binding was also found throughout the gray matter of the cerebellum, and in the pontine reticular nuclei.

Example 24

Drug Specificity of [³H]AZ—DTG binding

The haloperidol-sensitive sigma receptor binds [³H](+)3-[3-hydroxyphenyl]-N-(1-propyl)piperidine([³H](+)-3-PPP) and [³H]1,3-di-o-tolylguanidine ([³H]DTG), with high affinity. In order to elucidate its structure, photoaffinity labeling of the sigma receptor from guinea pig brain was accomplished using a novel radioactive photolabile derivative of DTG, [³H]-m-azido-1,3-di-o-tolylguanidine ([H]AZ—DTG). In the dark, [³H]AZ—DTG binds reversibly to sigma sites in brain membranes with high affinity (kd=28 nM). The drug specificity profile of [³H]AZ—DTG binding to brain membranes is identical to that of the prototypical sigma ligands [³H]DTG and [³H](+)-3-PPP. For photoaffinity labeling, membrane suspensions containing protease inhibitors were preincubated in the dark with [³H]AZ—DTG, then filtered and washed over Whatman GF/B glass fiber filters. The filters were then irradiated with long-wavelength UV light for a 15 minute period. Filter-bound proteins were solubilized with 50 mM Tris pH 7.4, 0.1% sodium dodecyl sulfate. Solubilized proteins were subjected to SDS-polyacrylamide gel electrophoresis. Fluorography of the SDS-PAGE gels revealed that [³H]AZ—DTG was selectively incorporated into a 29 kD polypeptide. Labeling of this polypeptide was completely blocked by the sigma ligands DTG, (+)-3-PPP, (+)pentazocine, and haloperidol at a concentration of 10 uM, while labeling was unaffected by morphine, serotonin, dopamine, scopolamine, or GABA at the same concentration. These results represent the first estimate of the size of the binding subunit of the haloperidol-sensitive sigma receptor.

Example 25

Additional sigma receptor binding assays

Sigma receptor binding assays using guinea pig brain membrane homogenates and the radioligands [³H]DTG and (+)[³H]3-PPP were done as previously described (Weber et al., P.N.A.S. (USA) 83:8784–8788 (1986)). Briefly, frozen whole guinea-pig brains (Biotrol, Indianapolis, Ind.) were homogenized in 10 volumes (w/v) of ice-cold 320 mM sucrose using a Brinkman polytron. The homogenate was centrifuged at 1,000×g for 20 minutes at 4° C. The supernatant was centrifuged at 20,000×g for 20 minutes at 4° C. The resulting pellet was resuspended in 10 initial volumes of 50 mM Tris/HCl buffer at pH 7.4 and centrifuged at 20,000×g for 20 minutes at 4° C. The resulting pellet was resuspended in 5 initial volumes ice-cold 50 mM Tris/Hcl (pH 0.4), and the final volume was adjusted to yield a protein concentration of 3 mg/ml, as determined by dye-binding protein assay (Biorad) using BSA as the standard. Aliquots of 20-ml were stored at −70° C. until used, with no detectable loss of binding.

For [³H]DTG binding assays, 20-ml aliquots of the frozen membrane suspension were thawed and diluted 1:3 in 50 mM Tris/HCl (pH 7.4). To 12×75 mm polystyrene test tubes were added 0.8 ml of diluted membrane suspension, 0.1 ml of [³H]DTG (46 Ci/mmol; see Weber et al., P.N.A.S (USA) 83:8784–8788 (1986) or (+)[³H]3-PPP (NEN, 98 Ci/mmol) to yield a final concentration of 1.4 nM, and 0.1 ml of unlabelled drugs or buffer. The protein concentration in the 1-ml final incubation volume was 800 ug/ml, corresponding to 32 mg of brain tissue (original wet weight) and to a tissue concentration within the linear range for specific binding. Non-specific binding was defined as that remaining in the presence of 10 uM haloperidol. Specific binding constituted >90% of total [³H]DTG binding. Incubations were terminated after 90 minutes at room temperature by addition of 4 ml of ice-cold 50 mM Tris/HCl (pH 7.4) and rapid filtration of the membrane suspension through Whatman GF/B glass-fiber filters under vacuum, using a 48-well cell harvester (Brandel, Gaithersburg, Md.). The filters were washed 2 times with 4 ml of 50 mM Tris/HCl (pH 7.4). Total filtration and washing time was less than 20 seconds. Each filter was dissolved in 10 ml Cytoscint (Westchem, San Diego, Calif.), and radioactivity was measured by liquid scintillation spectrometry at a counting efficiency of approximately 50%. $IC_{50}$ values were determined by interpolation from displacement-curve plots on semilogarithmic graph paper.

The $IC_{50}$ binding values (nM) are as follows: N,N-di(o-tolyl)guanidine (DTG, 32); N-(2-iodophenyl)-N'-(adamant-1-yl)guanidine (AdIpG, 6.2±0.7); N-(o-tolyl)-N'-(adamant-1-yl)guanidine (AdTG, 7.6±0.3); N,N'-di(adamant-1-yl)guanidine (DAG, 11.8±3.4); N-(cyclohexyl)-N'-(adamant-1-yl)guanidine (AdChG, 12.5±2.2);

N-(o-tolyl)-N'-(cyclohexyl)guanidine (13.0±1.0); N,N'-di-(2,6-dimethylphenyl)guanidine (DXG, 90±18); N-(o-tolyl)-N'-(4-amino-2-methylphenyl)guanidine (NH$_2$—DTG, 280±20); N,N'-di(phenyl)guanidine (DPG, 397±21); N-(o-tolyl)-N'-(o-iodophenyl)guanidine (IC$_{50}$=21); N,N'-di-(p-bromo-o-methylphenyl)guanidine (IC$_{50}$=37); N,N'-di-(m-n-propylphenyl)guanidine (IC$_{50}$=36); N-(o-tolyl)-N'-(p-nitro-otolyl)guanidine (IC$_{50}$=37); N,N'-di-(1-tetralinyl)guanidine (IC$_{50}$=58); N-(o-tolyl)-N'-(o-xylyl)guanidine (IC$_{50}$=70); N,N'-di-(cyclohexyl)guanidine (IC$_{50}$=71); N-(3,5-dimethyl-1-adamantanyl)-N'-(o -tolyl)guanidine (IC$_{50}$=15); N-(3,5-dimethyl-1-adamantanyl)-N'-(oiodophenyl)guanidine (IC$_{50}$=16); N-(1-adamantyl)-N'-(o-nitrophenyl)guanidine (IC$_{50}$=30); N,N'-di-(endo-2-norbornyl)guanidine (IC$_{50}$=16); N-(exo-2-isobornyl)-N'-(o-iodophenyl)guanidine (IC$_{50}$=18); N,N'-di-(exo-2-norbornyl)guanidine (IC$_{50}$=22); N-(exo-2-isobornyl)-N'-(o-tolyl)guanidine (IC$_{50}$=25); N-(o-iodophenyl)-N'-(t-butyl)guanidine (IC$_{50}$=20); N,N'-dibenzylguanidine (IC$_{50}$=90); N-(adamant-1-yl)-N'-(o-isopropylphenyl)guanidine (IC$_{50}$=24); N-(adamant-2-yl)-N'-(p-iodophenyl)guanidine (IC$_{50}$=2.7); N-(cyclohexyl)-N'-(p-bromo-o-tolyl)guanidine (IC$_{50}$=5.5); N-(adamantan-2-yl)-N'-(o-iodophenyl)guanidine (IC$_{50}$=5.2); 2-imino-1,3H-dibenzo[d,f]-[1,3]-diazepine (Bridge-DPG, >10,000); N,N'-di(methyl)guanidine (DMG, >10,000); (+)-3-PPP (76±4); (−)-3-PPP (280±21); (+)-pentazocine (43±2); (−)-pentazocine (135±3); (−)-cyclazocine (2600±210); (−)-SKF10047 (4000±566); haloperidol (5±0.3); BMY 14802 (120±15); rimcazole (1400±100); tiospirone (233±52); perphenazine (42±10); chlorpromazine (1475±265); sulpiride (>10,000); TCP (1100±110); PCP (1050±106); and MK-801 (>10,000).

Example 26

Effect of Diazepam and N,N'-Disubstituted Guanidines on Light/Dark Exploration of Mice The inventors wish to thank Brenda Costall, University of Bradford, Bradford, BD7 1DP, England, for screening the sigma receptor ligands according to the procedure disclosed by her and others in Jones et al., *Br. J. Pharmacol.* 93:985–993 (1988). According to this procedure, male albino BKW mice, 25–30 g, were housed 10 to a cage and allowed free access to food and water. They were kept on reversed light cycle with the lights on between 22 h 00 min and 10 h 00 min.

The apparatus was an open-topped box, 45 cm long, 27 cm wide and 27 cm high, divided into a small (⅖) area and a large (⅗) area by a partition that extended 20 cm above the walls. There was a 7.5×7.5 opening in the partition at floor level. The small compartment was painted black and the large compartment white. The floor of each of the compartments was marked into 9 cm squares. The white compartment was illuminated by a 100 W tungsten bulb 17 cm above the box and the black compartment by a similarly placed 60 W red bulb. The laboratory was illuminated with red light.

All tests were performed between 13 h 00 min and 18 h 00 min. Each mouse was tested by placing it in the center of the white area and allowing it to explore the novel environment for 5 min. Its behavior was recorded on videotape and the behavioral analysis was performed subsequently from the recording. Five parameters were measured: the latency to entry into the dark compartment, the time spent in each area, the number of transitions between compartments, the number of lines crossed in each compartment and the number of rears in each compartment.

The N,N'-disubstituted guanidines, dissolved in distilled water, were administered subcutaneously 40 min before testing over the dosage range of 0.01 ug to 0.1 mg/kg (5 mice per dosage level). Diazepam (0.063–10 mg/kg) was dissolved in the minimum quantity of polyethylene glycol, diluted to the appropriate volume with distilled water and administered intraperitoneally to five mice for each dosage level. The results are shown in FIGS. 1–6 (The cross hatched area=light area; solid columns=dark area).

As shown in FIG. 1, diazepam dose-dependently increased the proportion of time the mice spent in the larger, lighted area of the test chamber. The numbers of line crossings and rears in the light compartment increased at the expense of those in the dark compartment. At the highest dose of diazepam (10 mg/kg), the numbers of rears and line crossings decreased significantly showing that the drug was markedly sedative. The latency to entering the dark compartment increased with a peak effect at 0.25 mg/kg (latency=30 sec) while controls showed a latency of 9 sec (S.E.M.s<12.1%, P<0.001).

Figure 2:
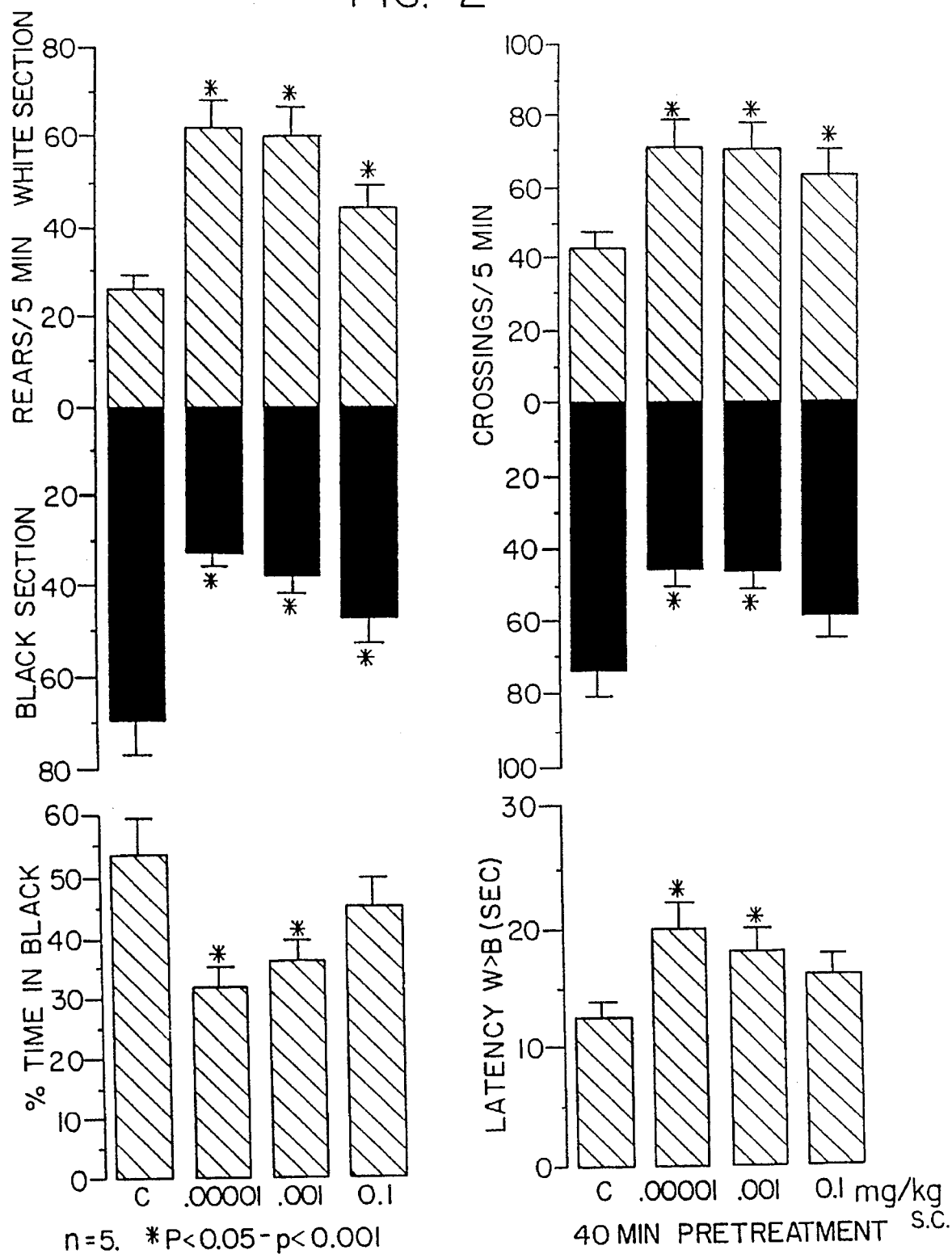
FIG. 2 is a graphical representation of the data resulting from the in vivo s.c. administration of N,N'-di(adamantan-1-yl)guanidine (DAG) on mouse behavior in the black:white test box.

As shown in FIG. 2, N,N'-di-(adamantan-1-yl)guanidine tended to increase the proportion of time the mice spent in the larger, lighted area of the test chamber, with a peak at 0.01 ug/kg. The numbers of line crossings and rears in the light compartment increased at the expense of those in the dark compartment. At the highest dose of N,N'-di-(adamantan-1-yl) guanidine (0.1 mg/kg), the numbers of rears and line crossings did not decrease significantly showing that the drug was not sedative at this level. The latency to entering the dark compartment increased with a peak effect at 0.01 ug/kg (latency=20 sec) while controls showed a latency of 12 sec (P<0.05<0.001).

Figure 3:
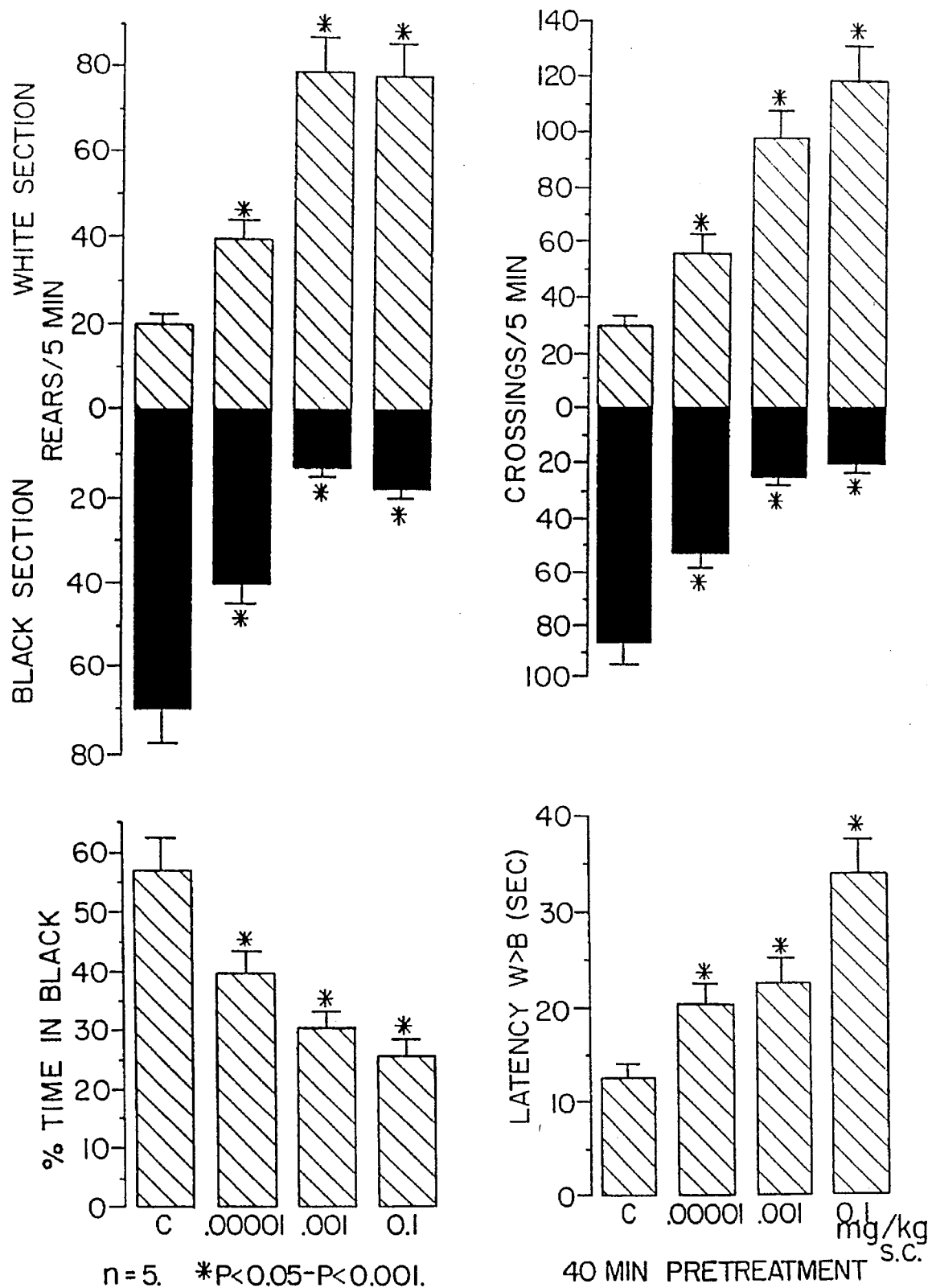
FIG. 3 is a graphical representation of the data resulting from the in vivo s.c. administration of N-(2-methylphenyl)-N'-(adamantan-1-yl)guanidine (AdTG) on mouse behavior in the black:white test box.

As shown in FIG. 3, N-(adamantan-1-yl)-N'-(2-methylphenyl)guanidine dose dependently increased the proportion of time the mice spent in the larger, lighted area of the test chamber. The numbers of line crossings and rears in the light compartment increased at the expense of those in the dark compartment. At the highest dose of N-(adamantan-1-yl)-N'-(2-methylphenyl)guanidine (0.1 mg/kg), the numbers of rears and line crossings did not decrease significantly showing that the drug was not sedative at this level. The latency to entering the dark compartment also increased in a dose-dependent manner.

Figure 5:
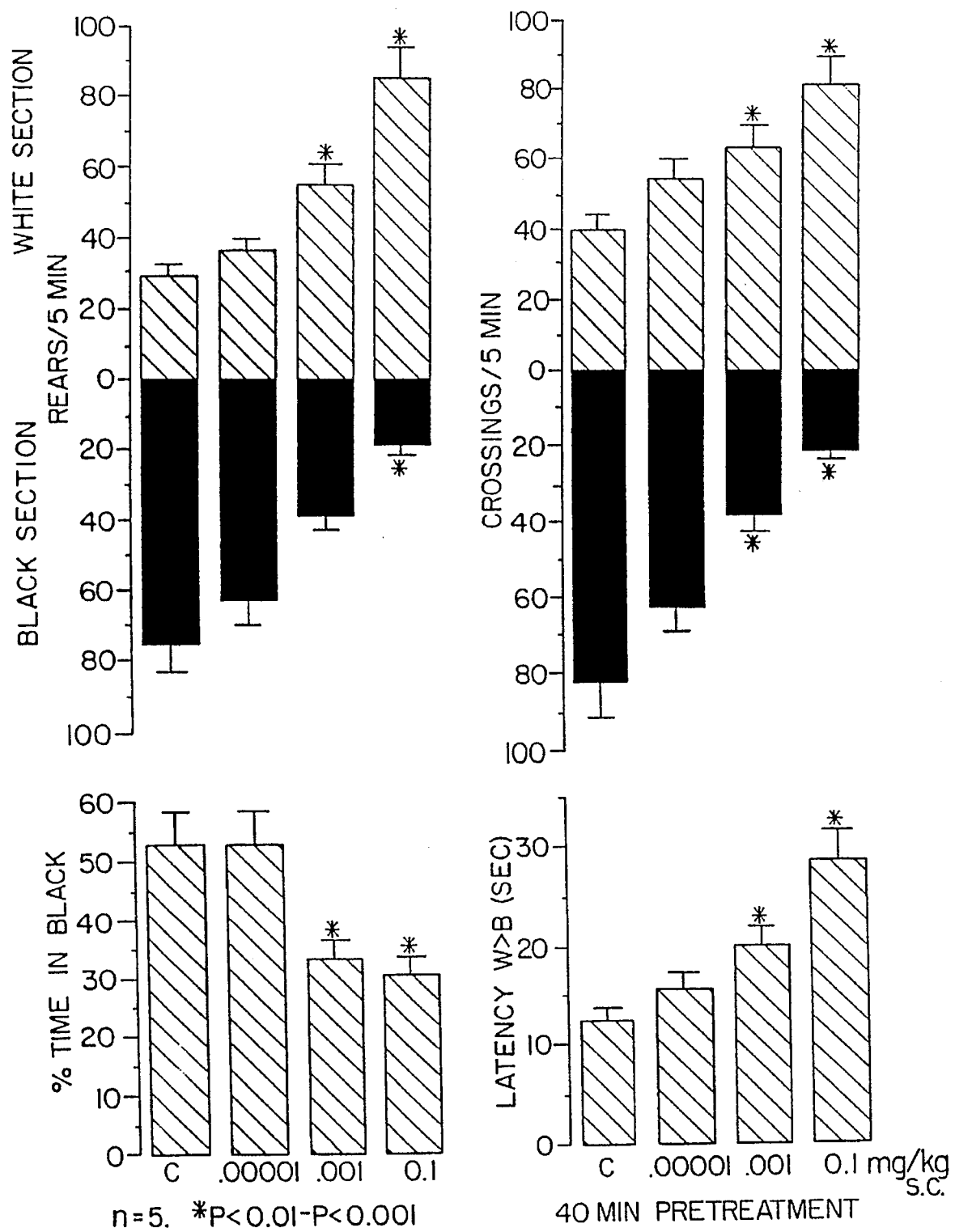
FIG. 5 is a graphical representation of the data resulting from the in vivo s.c. administration of N-(2-iodophenyl)-N'-(adamantan-1-yl)guanidine (AdIpG) on mouse behavior in the black:white test box.

As shown in FIG. 5, N-(adamantan-1-yl)-N'-o-iodophenyl-guanidine also increased, in a dose-dependent manner, the proportion of time the mice spent in the larger, lighted area of the test chamber. The numbers of line crossings and rears in the light compartment increased at the expense of those in the dark compartment. At the highest dose of N-(adamantan-1-yl)-N'-o-iodophenyl guanidine (0.1 mg/kg), the numbers of rears and line crossings did not decrease significantly showing that the drug was not sedative at this level. The latency to entering the dark compartment also increased in a dose-dependent manner.

Figure 6:
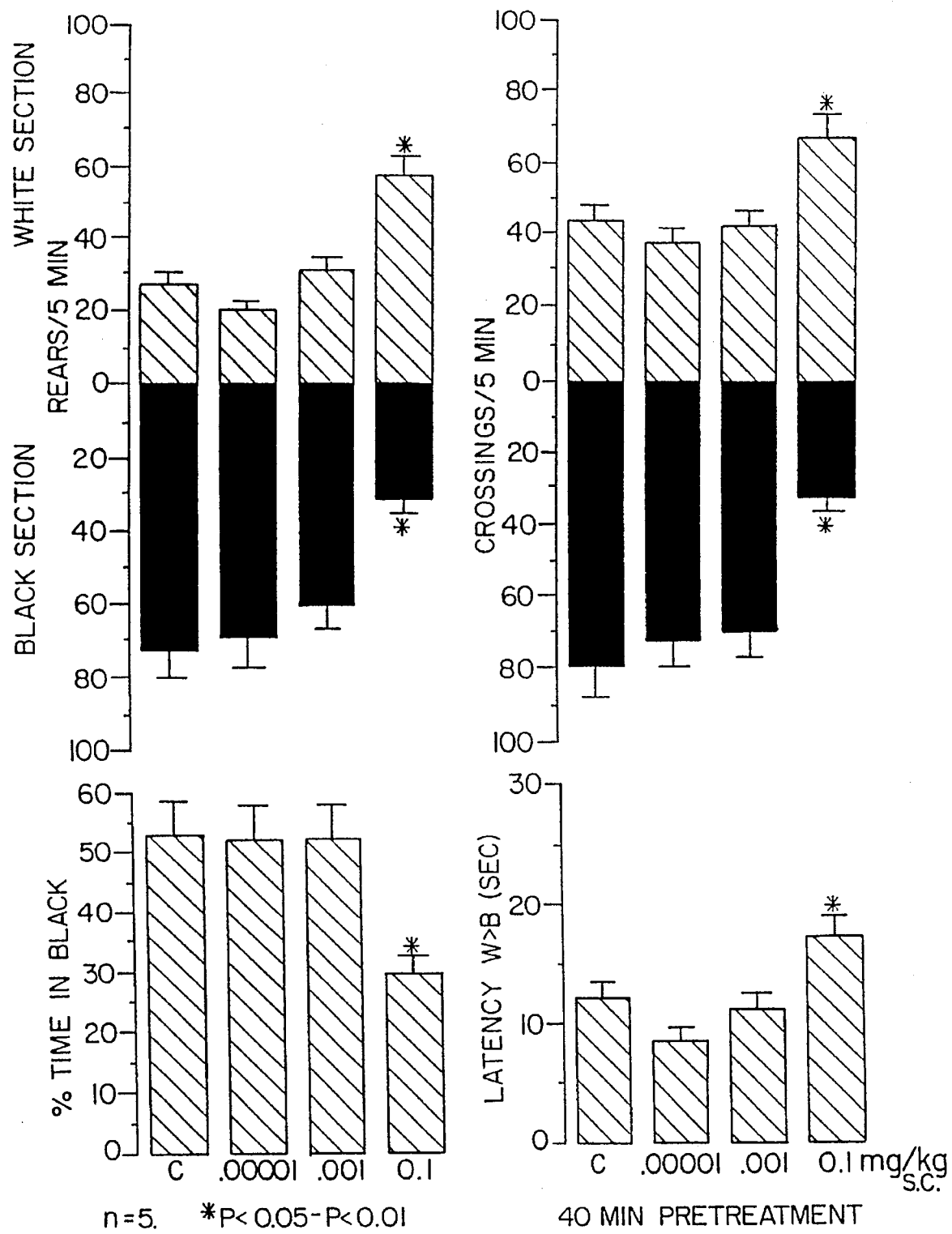
FIG. 6 is a graphical representation of the data resulting from the in vivo s.c. administration of N-(3,5-dimethyladamantan-1-yl)-N'-[(E)-2-phenylethenyl]phenylguanidine (F-114-B) on mouse behavior in the black:white test box.

For comparison, a compound with a relatively low sigma receptor affinity was tested for anxiolytic activity. As shown in FIG. 6, N-(3,5-dimethyladamantan-1-yl)-N'-{[(E)-2-phenylethenyl]phenyl}guanidine (IC$_{50}$=1,000 nM) generally did not increase the proportion of time the mice spent in the larger, lighted area of the test chamber. The numbers of line crossings and rears in the light compartment tended to remain the same except at the highest dosage. At the highest dose of N-(3,5-dimethyladamantan-1-yl)-N'-{[(E)-2-phenylethenyl]phenyl}guanidine (0.1 mg/kg), the numbers of rears and line crossings did not decrease significantly showing that the drug was not sedative at this level.

Figure 7:
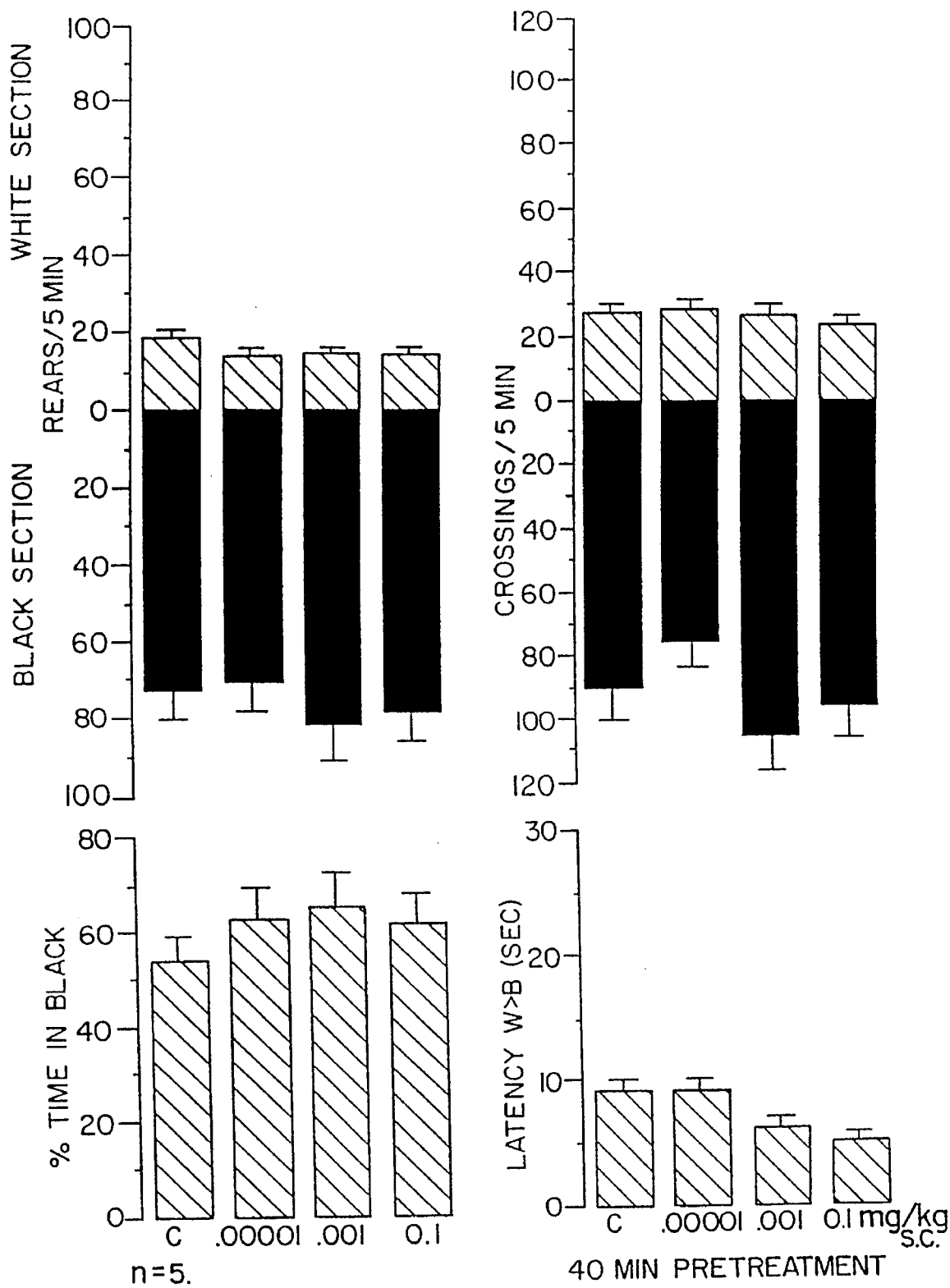
FIG. 7 is a graphical representation of the data resulting from the in vivo s.c. administration of DTG on mouse behavior in the black:white test box.

As shown in FIG. 7, N,N'-di-(2-methylphenyl)guanidine did not affect significantly the number of rears, crossings, or the % time in the black compartment at the concentrations tested. This result is surprising in light of the high sigma receptor binding of this compound ($IC_{50}=32.0\pm1$). Although the inventors do not wish to be bound by any particular theory, it would appear that DTG does not exhibit anxiolytic activity in the in vivo assay since it is quickly metabolized and thereby deactivated by the animal.

Figure 4:
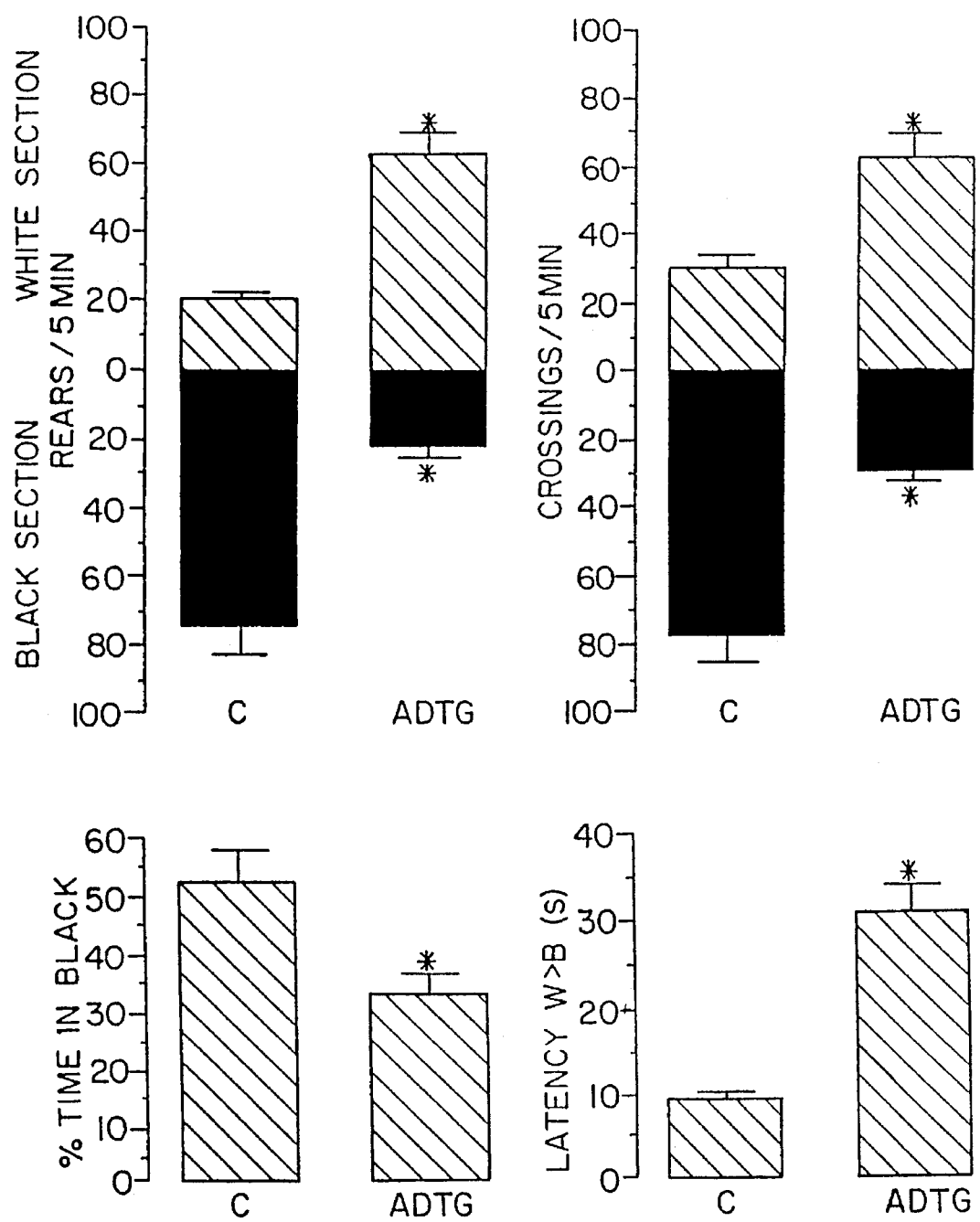
FIG. 4 is a graphical representation of the data resulting from the in vivo oral administration of AdTG on mouse behavior in the black:white test box.

Next, N-(adamantan-1-yl)-N'-(2-methylphenyl)guanidine, N,N'-di-(adamantan-1-yl)guanidine and N-(adamantan-1-yl)-N'-(o-iodophenyl)guanidine were orally administered to the mice at a dose of 1 mg/kg. As shown in FIG. 4, orally administered N-(adamantan-1-yl)-N'-(2-methylphenyl)guanidine increased significantly the proportion of time the mice spent in the larger, lighted area of the box. Moreover, the numbers of line crossings and rears in the light compartment increased at the expense of those in the dark compartment.

Figure 8:
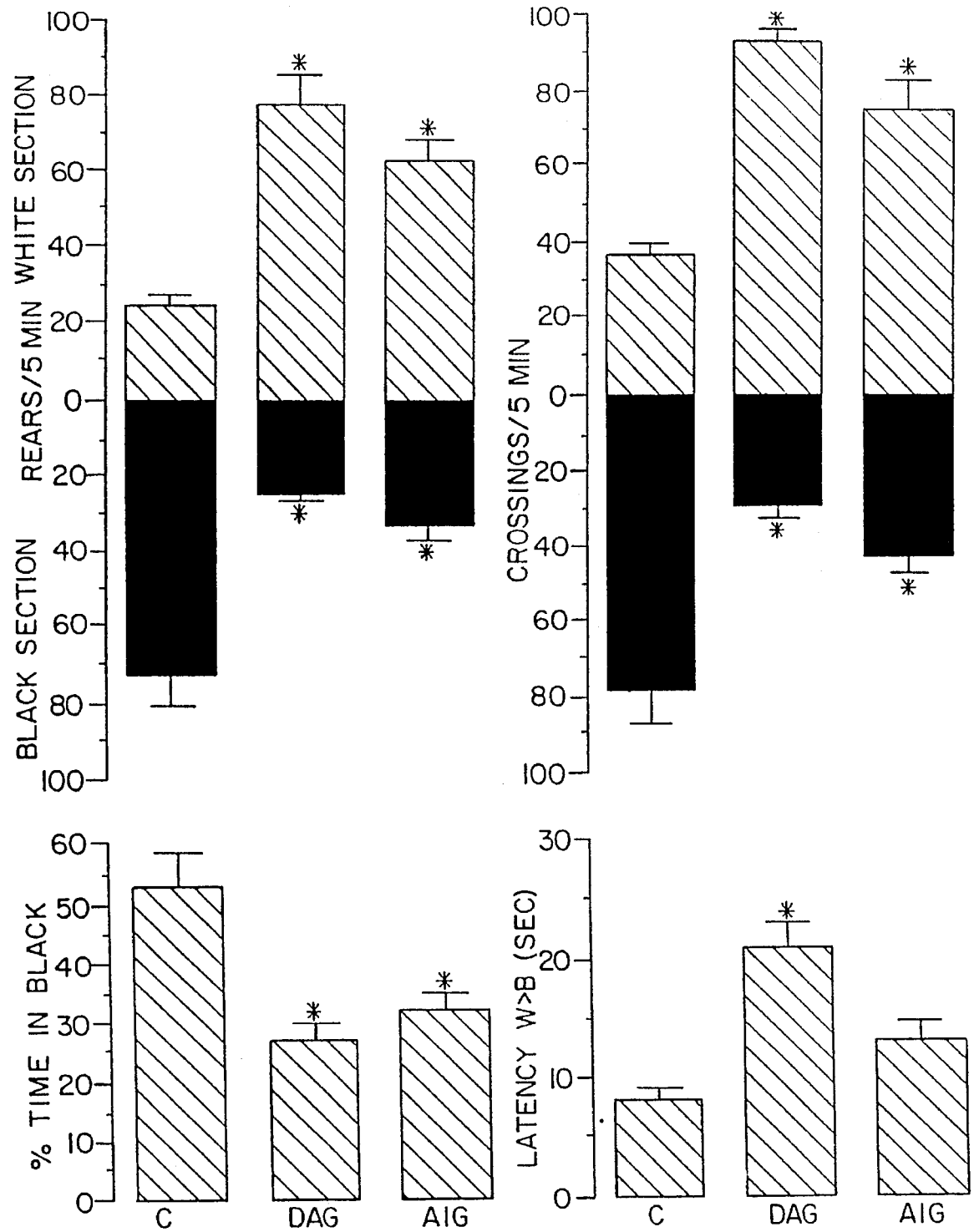
FIG. 8 is a graphical representation of the data resulting from the oral administration of N,N'-di-(adamantan-1-yl)guanidine and N-(adamantan-1-yl)-N'-(o-iodophenyl)guanidine, in comparison with controls, on mouse behavior in the black:white test box.

As shown in FIG. 8, N,N'-di-(adamantan-1-yl)guanidine and N-(adamantan-1-yl)-N'-(o-iodophenyl)guanidine caused an increase in the numbers of line crossings and rears in the light compartment at the expense of those in the dark compartment. Compared with controls, the numbers of rears and line crossings did not decrease significantly showing that the two drugs were not sedative at the dosage level administered. The two drugs also caused an increase in the latency to entering the dark compartment in comparison to controls. These experiments confirm that N-(adamantan-1-yl)-N'-(2-methylphenyl)guanidine, N,N'-di-(adamantan-1-yl)guanidine and N-(adamantan-1-yl)-N'-(o-iodophenyl)guanidine have anxiolytic activity when orally administered.

As shown in FIG. 9, N-cyclohexyl-N'-(2-methylphenyl)guanidine increases significantly the proportion of time the mice spent in the larger, lighted area of the box. Moreover, the numbers of line crossings and rears in the light compartment increased in a dose-dependent manner at the expense of those in the dark compartment. Compared with controls, the total number of rears and line crossings did not decrease significantly, showing that the drug was not sedative at the dosage levels administered. The drug also caused an increase in the latency to entering the dark compartment compared to controls.

Figure 10:
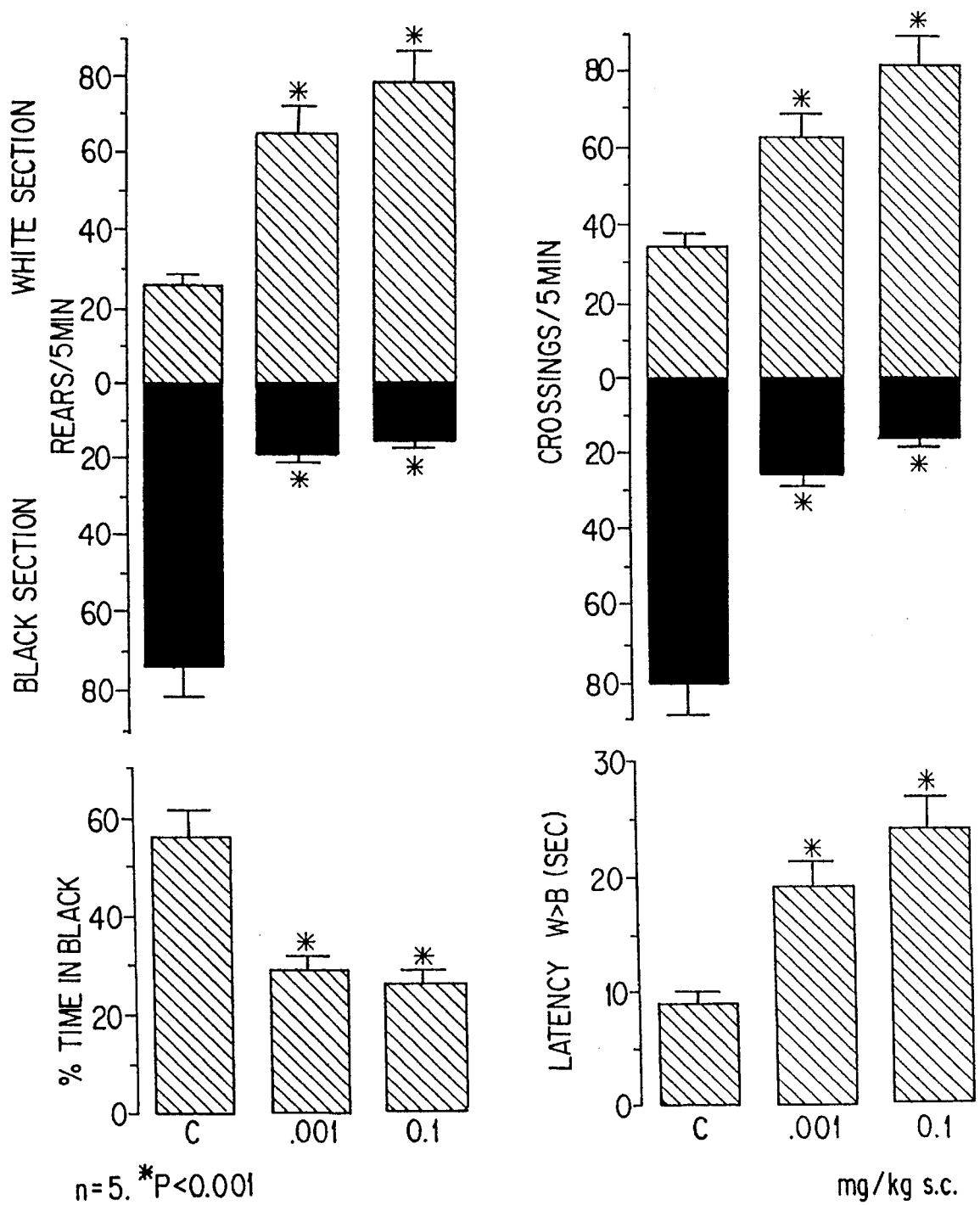
FIG. 10 is a graphical representation of the data resulting from the in vivo s.c. administration of N-(±)endo-2-norbornyl-N'-(2-iodophenyl)-guanidine, in comparison to controls, on mouse behavior in the black:white test box.

As shown in FIG. 10, N-((±)-endo-2-norbornyl)-N'-(2-iodophenyl)guanidine caused a significant dose-dependent increase in the number of rears in the light compartment at the expense of those in the dark compartment. Compared with controls, the total number of rears and line crossings did not decrease significantly, showing that the drug was not sedative at the dosage levels administered. The drug also caused a dose-dependent increase in the latency to entering the dark compartment compared to controls.

As shown in FIG. 11, N-(exo-2-norbornyl)-N'-(2-methylphenyl)guanidine caused an increase in the number of rears in the light compartment at the expense of those in the dark compartment. Compared with controls, the total number of rears and line crossings did not decrease significantly, showing that the drug was not sedative at the dosage level administered. The drug also caused an increase in the latency to entering the dark compartment when administered at 0.1 mg/kg in comparison to controls.

Figure 12:
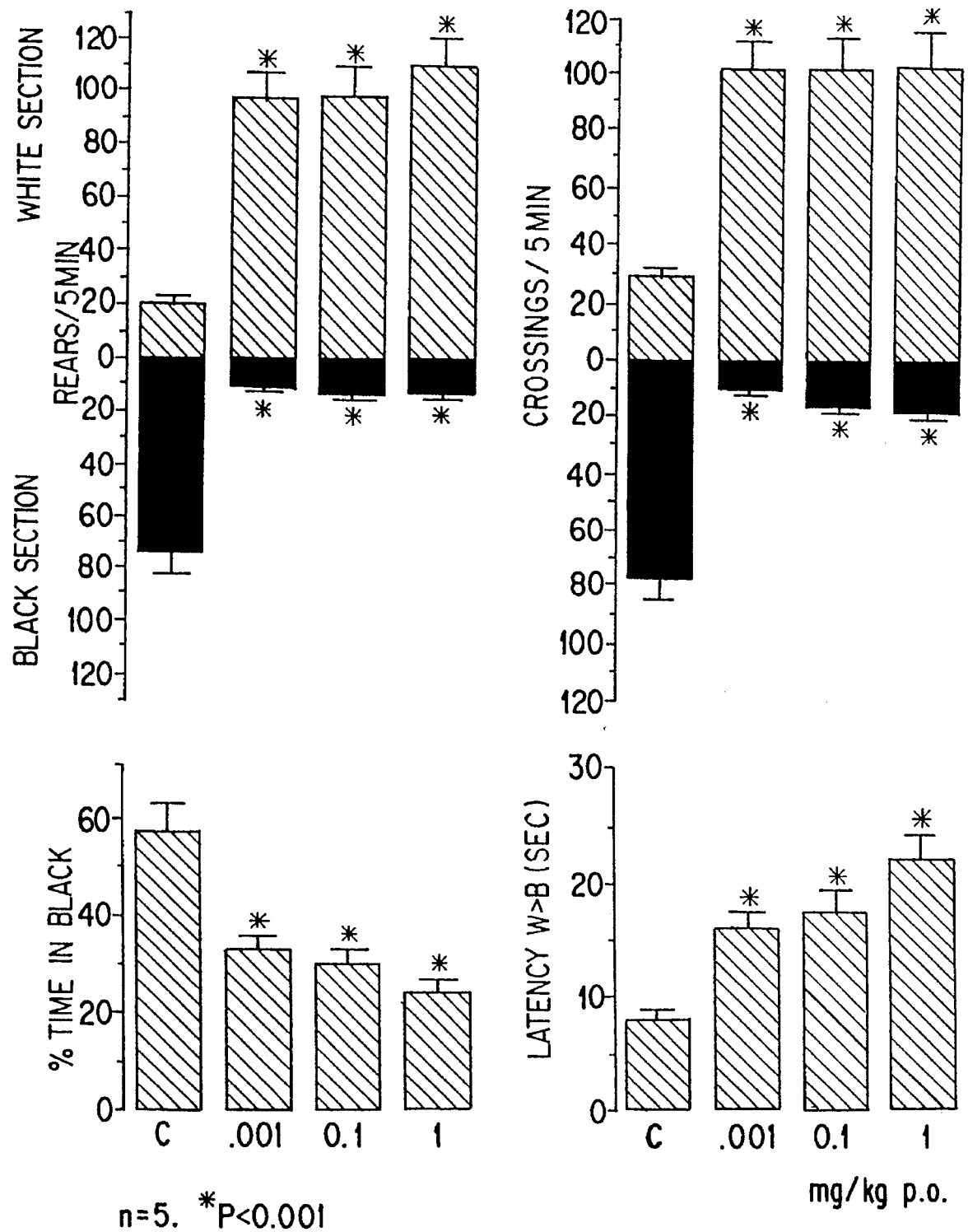
FIG. 12 is a graphical representation of data resulting from the in vivo s.c. administration of N-(adamantan-1-yl)-N'-cyclohexylguanidine, in comparison to controls, on mouse behavior in the black:white test box.

As shown in FIG. 12, N-(adamantan-1-yl)-N'-cyclohexylguanidine caused an increase in the number of rears in the light compartment at the expense of those in the dark compartment. Compared with controls, the total number of rears and line crossings did not change significantly, showing that the drug was not sedative at the dosage levels administered. The drug also caused a dose-dependent increase in the latency to entering the dark compartment in comparison to controls.

As shown in FIG. 13, N-(cyclohexyl)-N'-(2-methylphenyl) guanidine, when administered orally, caused an increase in the total numbers of rears in the light compartment at the expense of those in the dark compartment. Compared with controls, the number of rears and line crossings did not change significantly, showing that the compound was not sedative at the dosage level administered. The compound also caused a slight increase in the latency to entering the dark compartment in comparison to controls. However, a significant decrease in the percentage of time in the black compartment was observed.

Figure 14:
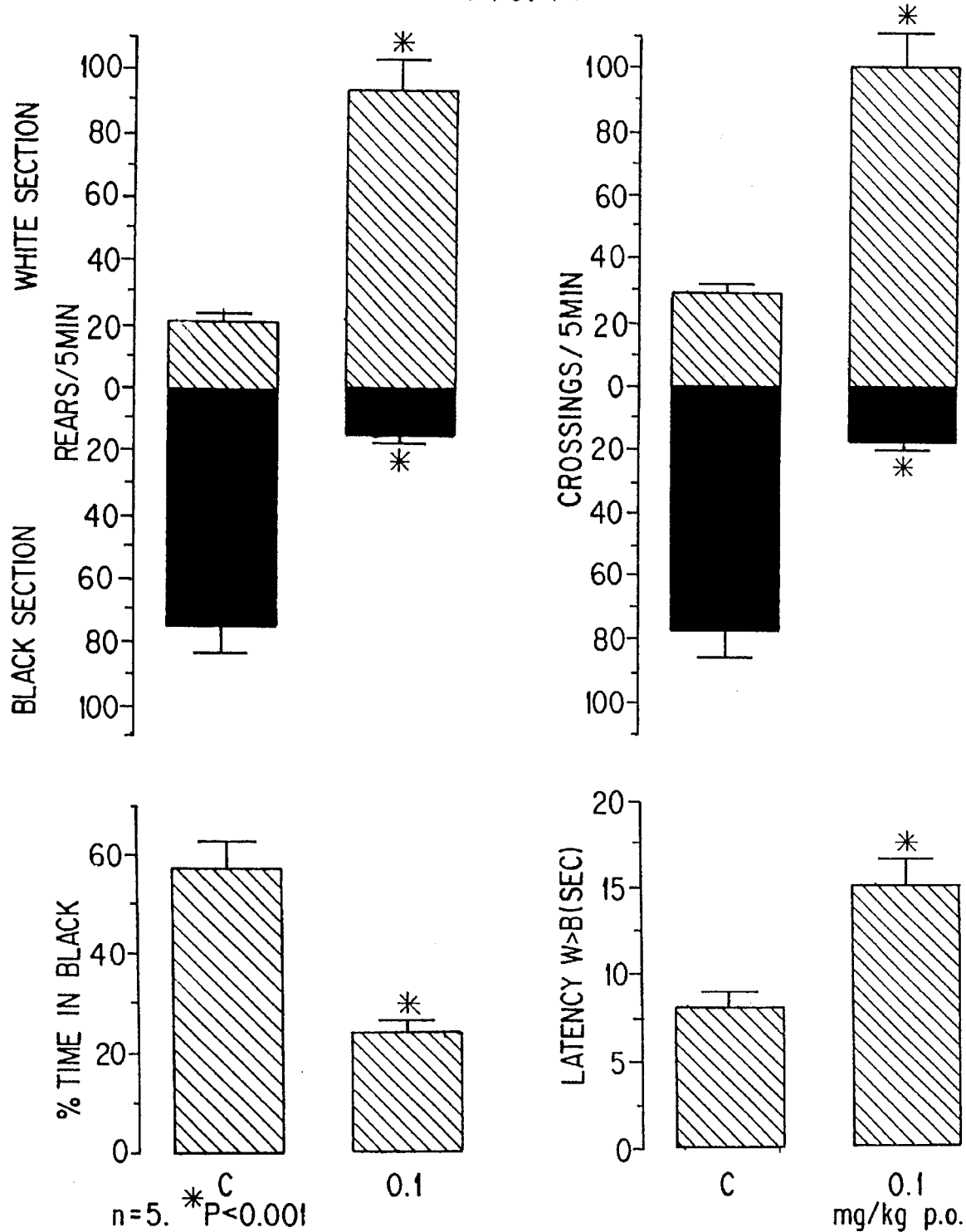
FIG. 14 is a graphical representation of the data resulting from the oral administration of N-((±)-endo-2-norbornyl-N'-(2-iodophenyl)guanidine, in comparison with controls, on mouse behavior in the black:white test box.

As shown in FIG. 14, N-((±)-endo-2-norbornyl)-N'-2-iodophenyl)guanidine, administered orally, caused an increase in the number of rears in the light compartment at the expense of those in the dark compartment. Compared with controls, the total number of rears and line crossings did not decrease significantly, showing that the drug was not sedative at the dosage level administered. The drug also caused an increase in the latency to entering the dark compartment in comparison to controls and a decrease in the percentage time spent in the black compartment.

Figure 15:
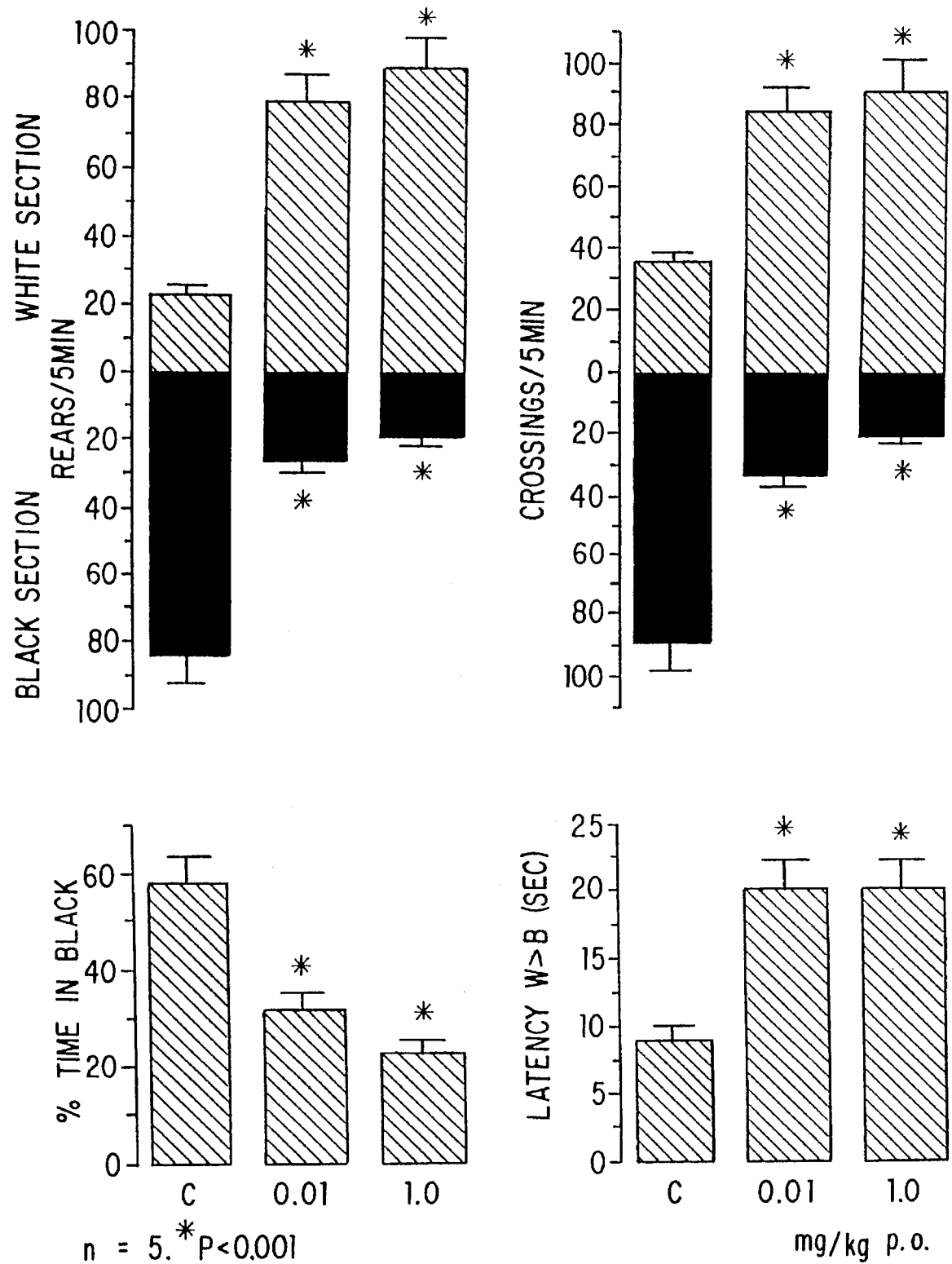
FIG. 15 is a graphical representation of the data resulting from the oral administration of N-(exo-2-norbornyl)-N'-(2-methylphenyl)guanidine, in comparison with controls, on mouse behavior in the black:white test box.

As shown in FIG. 15, N-(exo-2-norbornyl)-N'-(2-methylphenyl)guanidine, when administered orally, caused an increase in the number of rears in the light compartment at the expense of those in the dark compartment. Compared with controls, the total number of rears and line crossings did not decrease significantly, showing that the drug was not sedative at the dosage levels administered. The drug also caused an increase in the latency to entering the dark compartment in comparison with controls, and a decrease in the percentage time spent in the black compartment.

Figure 16:
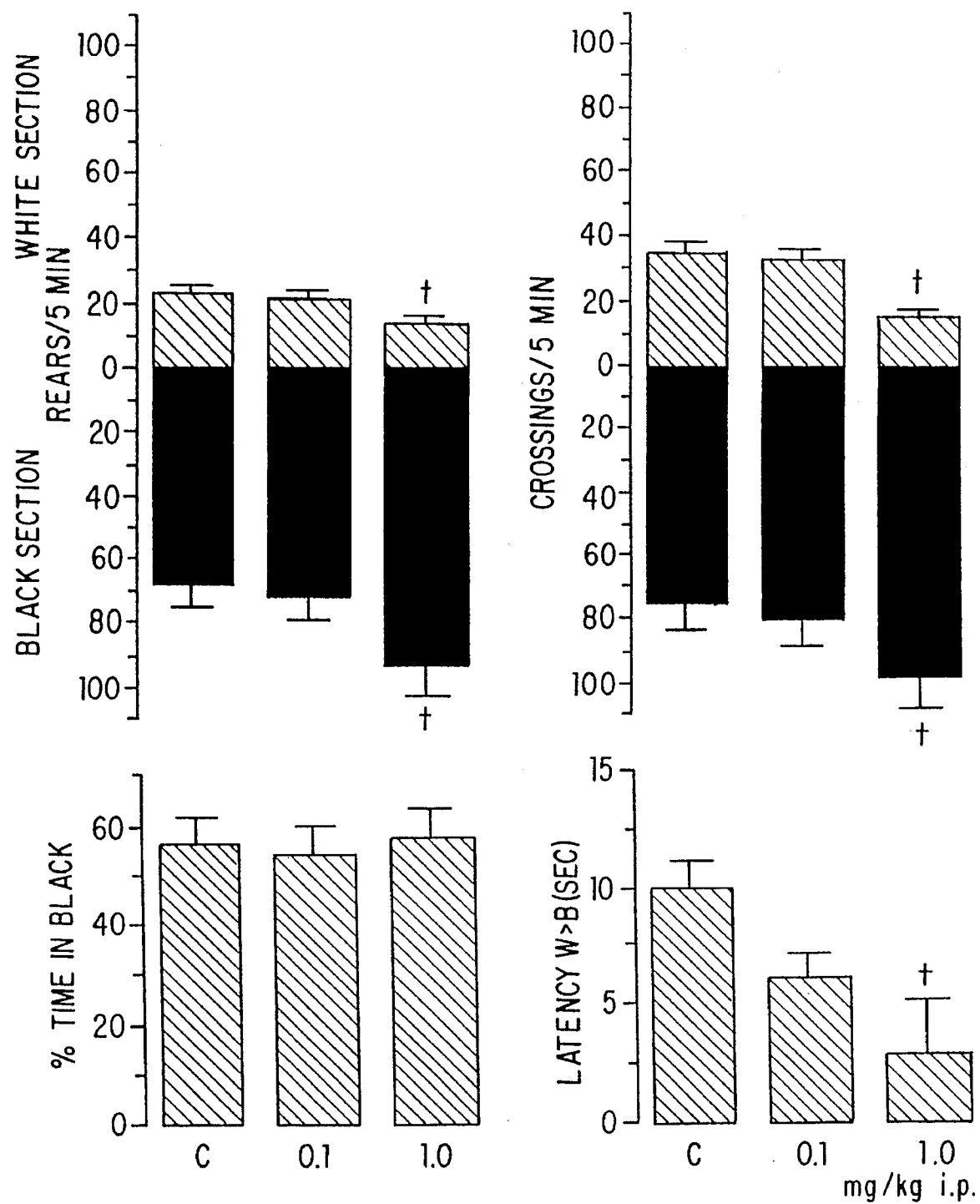
FIG. 16 is a graphical representation of the data resulting from the in vivo i.p. administration of N-(2-styrylphenyl)-N'-(2-iodophenyl)guanidine, in comparison with controls, on mouse behavior in the black:white test box.

As shown in FIG. 16, N-(2-styrylphenyl)-N'-(2-iodophenyl)guanidine, a non-active control compound, did not affect the numbers of line crossings or rears in the light compartment. Moreover, the drug actually decreased the latency to entering the dark compartment in comparison with controls. No significant change in the percentage time in the black compartment was observed.

Example 27

The Anxiolytic Potential of Diazepam and N-(adamantan-1-yl)-N'-(2-methylphenyl)guanidine in a Rat Social Interaction Test Male Hooded Lister rats (Glaxo bred, 200–250 g), were housed 5 to a cage and were kept in the laboratory environment for at least a week before testing. Rats paired in the test were taken from separate cages.

The compounds were screened for anxiolytic activity by Brenda Costall according to the disclosure of Jones, B. J. et al., *Br. J. Pharmacol.* 93:985–993 (1988) and File, S. E. et al., *Br. J. Pharmacol.* 62:19–24 (1978). The test arena consisted of an open-topped box, 62×62×33 cm with a 7×7 matrix of infra-red photocell beams in the walls, 2.5 cm from the floor. Diazepam and N-(adamantan-1-yl)-N'-(2-methylphenyl)-guanidine were tested by treating both members of a pair of rats with the same treatment 40 min. before testing (Rats were placed singly in small cages immediately after dosing until they were tested).

Testing involved placing each member of a pair of rats in opposite corners of the arena and then leaving them undisturbed for 10 min. while recording their behavior remotely on videotape. The behavioral assessments were made subsequently from the recordings. The time spent in social interaction was measured and expressed as a cumulative total for the 10 min session. The behaviors that comprised social interaction were: following with contact, sniffing (but not sniffing of the hindquarters), crawling over and under, tumbling, boxing and grooming.

Intraperitoneally administered diazepam was tested over the dose range of 0.125–1 mg/kg. N-(adamantan-1-yl)-N'-(2-methylphenyl)guanidine was tested over the range of 0.001–0.1 mg/kg. The results appear in FIG. 17 (n=6, P<0.001).

Figure 17:
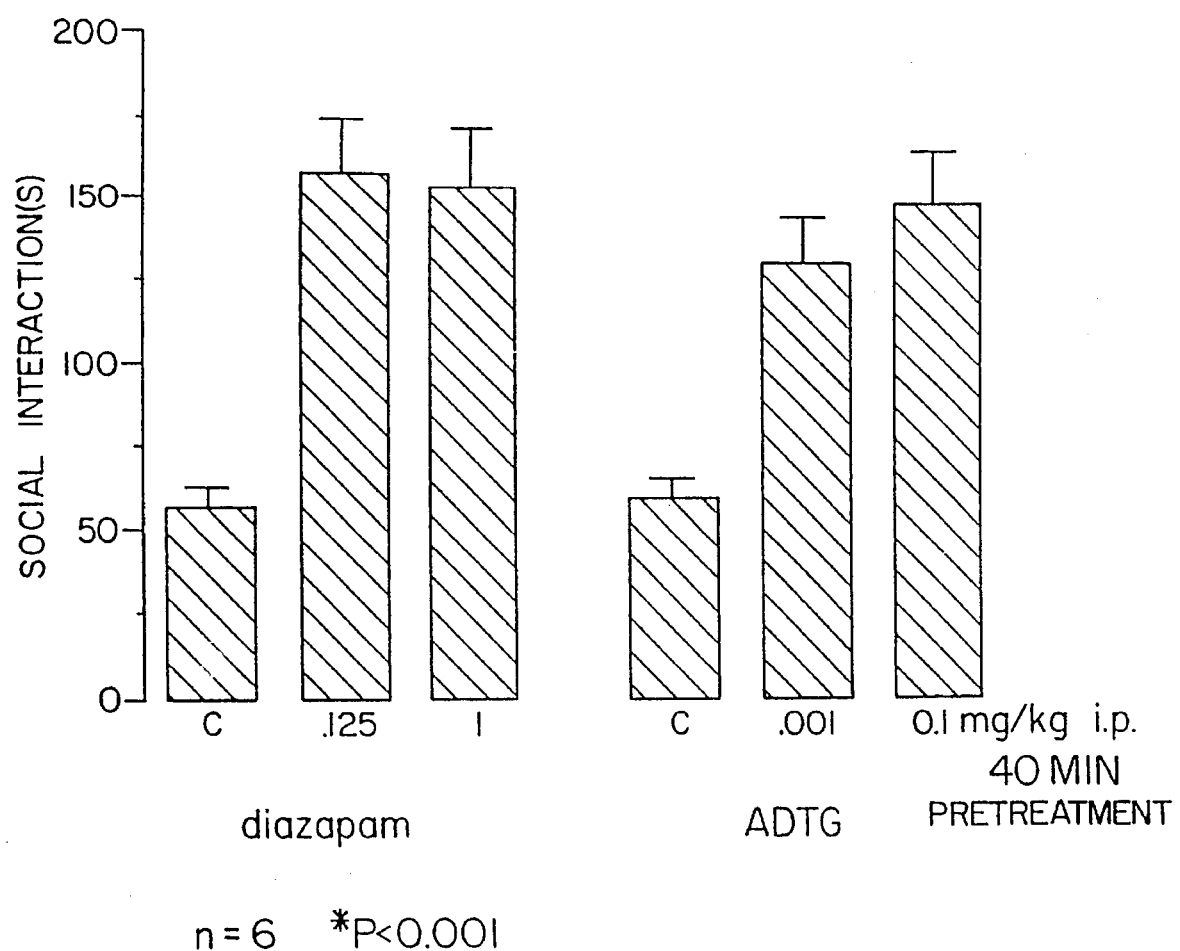
FIG. 17 is a graphical representation of the data resulting from the in vivo i.p. administration of diazepam and AdTG (for comparison) in the rat social interaction test.

As shown in FIG. 17, both diazepam and N-(adamantan-1-yl)-N'-(2-methylphenyl)guanidine significantly increased social interactions. However, N-(adamantan-1-yl)-N'-(2-methylphenyl)guanidine produced about the same result at one-tenth the dose of diazepam (1 mg/kg for diazepam and 0.1 mg/kg for N-(adamantan-1-yl)-N'-(2-methylphenyl)guanidine). These results provide strong indication that N-(adamantan-1-yl)-N'-(2-methylphenyl)guanidine will have anxiolytic activity in man, especially since the social interaction test in the rat is one of the most extensively validated tests (See File et al., supra).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition, in unit dosage form, which comprises, per unit dose, an amount effective to alter the sigma brain receptor modulated activity of a human being, of a water soluble N,N'-disubstituted guanidine which displaces in vitro N,N'-di-(4-[$^3$H]-2-methylphenyl)guanidine bound to isolated mammalian brain membrane, wherein said N,N'-disubstituted guanidine is selected from the group consisting of:

N-(adamantan-1-yl)-N'-(2-trifluoromethylphenyl)guanidine; and

N-(adamantan-1-yl)-N'-(2-trifluoromethyl-4-fluorophenyl)guanidine.

2. The pharmaceutical composition of claim 1, in a form suitable for oral administration.

3. The pharmaceutical composition of claim 1, in a form suitable for parenteral injection.

4. The pharmaceutical composition of claim 1, wherein the effective amount of the disubstituted guanidine ranges from about 0.1 mg to about 1 g per unit dose.

5. A method of treating a human being suffering from a psychotic mental illness associated with hallucinations, which comprising administering thereto, in an amount effective to ameliorate the hallucinations, an N,N'-disubstituted guanidine compound exhibiting high binding affinity to the sigma receptor and which is an antagonist to the sigma receptor binding affinity of a hallucinogenic benzomorphan, wherein said N,N'-disubstituted guanidine is selected from the group consisting of:

N-(adamant-1-yl)-N'-(p-iodophenyl)guanidine;

N-(adamantan-1-yl)-N'-(2-trifluoromethylphenyl)guanidine;

N-(adamantan-1-yl)-N'-(2,4-difluorophenyl)guanidine; and

N-(adamantan-1-yl)-N'-(2-trifluoromethyl-4-fluorophenyl)guanidine.

6. A pharmaceutical composition comprising a pharmaceutically acceptable carrier and an effective amount of a compound selected from the group consisting of:

N-(adamantan-1-yl)-N'-(2-trifluoromethylphenyl)guanidine; and

N-(adamantan-1-yl)-N'-(2-trifluoromethyl-4-fluorophenyl)guanidine.

7. The pharmaceutical composition of claim 6 in a form suitable for oral administration.

8. The pharmaceutical composition of claim 6 in a form suitable for parenteral administration.

9. The pharmaceutical composition of claim 6 wherein the effective amount of the compound is from about 0.1 mg to about 1 g per unit dose.

10. A pharmaceutical composition comprising a pharmaceutical carrier and an effective amount of N-(adamantan-1-yl)-N'-(2-trifluoromethyl-4-fluorophenyl)guanidine.

11. The pharmaceutical composition of claim 10 in a form suitable for oral administration.

12. The pharmaceutical composition of claim 10 in a form suitable for parenteral administration.

13. The pharmaceutical composition of claim 10 wherein the effective amount of the compound is from about 0.1 mg to about 1 g per unit dose.

14. A method of treating a human being suffering from a psychotic mental illness comprising administering to said human an effective amount of a compound selected from the group consisting of:

N-(adamant-1-yl)-N'-(p-iodophenyl)guanidine;

N-(adamantan-1-yl)-N'-(2-trifluoromethylphenyl)guanidine;

N-(adamantan-1-yl)-N'-(2,4-difluorophenyl)guanidine; and

N-(adamantan-1-yl)-N'-(2-trifluoromethyl-4-fluorophenyl)guanidine.

15. The method of claim 14 where the compound is administered orally.

16. The method of claim 14 where the compound is administered parenterally.

17. The method of claim 14 wherein an effective amount of N-(adamantan-1-yl)-N'-(2-trifluoromethyl-4-fluorophenyl)guanidine is administered to the human.

18. The method of claim 17 where the N-(adamantan-1-yl)-N'-(2-trifluoromethyl-4-fluorophenyl)guanidine is administered orally.

19. The method of claim 17 where the N-(adamantan-1-yl)-N'-(2-trifluoromethyl-4-fluorophenyl)guanidine is administered parenterally.

* * * * *